(12) United States Patent
Ali et al.

(10) Patent No.: US 7,662,846 B2
(45) Date of Patent: Feb. 16, 2010

(54) SELECTIVE SPIROCYCLIC GLUCOCORTICOID RECEPTOR MODULATORS

(75) Inventors: Amjad Ali, Piscataway, NJ (US); James M. Balkovec, Martinsville, NJ (US); Richard Beresis, Matawan, NJ (US); Steven L. Colletti, Princeton Junction, NJ (US); Donald W. Graham, Mountainside, NJ (US); Gool F. Patel, Califon, NJ (US); Cameron J. Smith, Lawrenceville, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 145 days.

(21) Appl. No.: 10/551,933
(22) PCT Filed: Apr. 19, 2004
(86) PCT No.: PCT/US2004/012102
§ 371 (c)(1), (2), (4) Date: Oct. 4, 2005
(87) PCT Pub. No.: WO2004/093805
PCT Pub. Date: Nov. 4, 2004

(65) Prior Publication Data
US 2006/0217563 A1 Sep. 28, 2006

Related U.S. Application Data
(60) Provisional application No. 60/464,784, filed on Apr. 23, 2003.

(51) Int. Cl.
C07D 487/00 (2006.01)
A01N 43/56 (2006.01)
(52) U.S. Cl. .................................. 514/403; 548/359.1
(58) Field of Classification Search .................. None
See application file for complete search history.

(56) References Cited

U.S. PATENT DOCUMENTS

| 4,412,995 A | 11/1983 | Bell et al. | |
|---|---|---|---|
| 2005/0054700 A1* | 3/2005 | Scanlan et al. | 514/373 |
| 2005/0256315 A1* | 11/2005 | Ali et al. | 548/257 |

FOREIGN PATENT DOCUMENTS

| WO | WO 03/061651 A | 7/2003 |
|---|---|---|
| WO | WO 03/086294 A | 10/2003 |
| WO | WO 2004/026248 A | 4/2004 |
| WO | WO 2004/075840 A | 9/2004 |

OTHER PUBLICATIONS

Smith et al., "Novel ketal ligands for the glucocorticoid receptor: in vitro and in vivo activity", Bioorganic&Medicinal chemistry Letters, 15 (2005) 2926-2931.*
Schacke et al.,, "Selective Glucocorticoid Receptor Agonists (SEGRAs): Novel ligands with an improved therapeutic index", Molecular and Cellular Endocrinology (2007), doi:10.1016/j.mce.2007.05.014, 9 pages.*
Zips et al., "In vitro and in vivo evaluation of new anticancer agents", in vivo, 19 (2005), 1-7 (8 pages).*
Barnes, P.J., "Mediators of Chronic Obstructive Pulmonary Disease", Pharmacological Reviews, vol. 56, No. 4, p. 515-548.*
http://en.wikipedia.org/wiki/Racemic_mixture (1 PAGE ONLY).*
McCulloch et al. "Signalling Platforms that Modulate the Inflammatory Response: New Targets for Drug Development", Nature Reviews Drug Discovery (2006), vol. 5, pp. 864-876.*
Shacter et al., "Chronic Inflammation and Cancer", Oncology (2002), vol. 16, p. 217-232.*
Hirschmann, et al., "Synthesis and Structure of Steroidal 4-Pregneno[3,2-c]Pyrazoles. A Novel Class of Potent Anti-Inflammatory Steroids", J. Am. Chem. Soc., vol. 85, pp. 120-122 (1963).
Hirschmann et al., "Methylated Steroids. IV. 6,16a-Dimethyl-Hydrocortisone and Related Compounds", J. Am. Chem. Soc., vol. 85, pp. 236-238, (1963).
Hirschmann, et al., "Synthesis and Structure of Steroidal Pregn-4-eno-and 5a-Pregnano[3,2-c]pyrazoles. A Novel Class of Potent Anti-Inflammatory Steroids", J. Am. Chem. Soc., vol. 86, pp. 1520-1527 (1964).
Hirschmann, et al., "Synthesis of Pregn-4-eno[3,2-c]pyrazoles Related to 9a-Fluoro-16a-methylcortisol", J. Med. Chem., vol. 7, pp. 352-355, (1964).
Robert Newton, "Molecular mechanisms of glucocorticoid action: what is important?", Thorax, vol. 55, pp. 603-613, (2000).
Schane, et al., "Glucocorticoid/Antiinflammatory activities of Nonsteroidal Phenylpyrazoles in the Rat", Steroids, vol. 45, No. 2, pp. 171-185, (1985).

* cited by examiner

*Primary Examiner*—Golam M. M. Shameem
*Assistant Examiner*—Sun Jae Y Loewe
(74) *Attorney, Agent, or Firm*—Yong Zhao; Valerie J. Camara

(57) ABSTRACT

The present invention encompasses compounds of Formula (I) and Formula (II) or pharmaceutically acceptable salts or hydrates thereof, which are useful as selective glucocorticoid receptor ligands for treating a variety of autoimmune and inflammatory diseases or conditions. Pharmaceutical compositions and methods of use are also included.

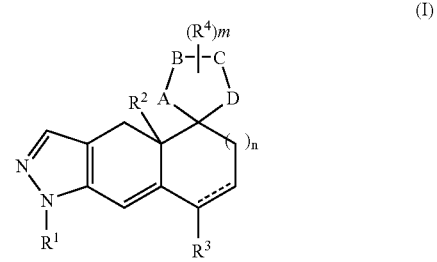

(I)

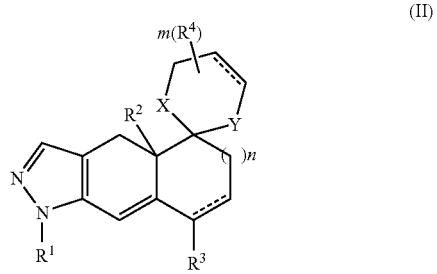

(II)

5 Claims, No Drawings

SELECTIVE SPIROCYCLIC GLUCOCORTICOID RECEPTOR MODULATORS

CROSS REFERENCE TO RELATED APPLICATIONS

This application is a U.S. national Phase application under 35.U.S.C. § 371 of PCT Application No. PCT/US2004/012102, filed Apr. 19, 2004, which claims priority under 35 U.S.C. 119 to U.S. No. 60/464,784, filed Apr. 23, 2003.

BACKGROUND OF THE INVENTION

Intracellular receptors (IR's) are a class of structurally related proteins involved in the regulation of gene expression. The steroid hormone receptors are a subset of this superfamily whose natural ligands are typically comprised of endogenous steroids such as estradiol, progesterone, and cortisol. Man-made ligands to these receptors play an important role in human health and, of these receptors, the glucocorticoid receptor has an essential role in regulating human physiology and immune response. Steroids that interact with the glucocorticoid receptor have been shown to be potent anti-response. Steroids that interact with the glucocorticoid receptor have been shown to be potent anti-inflammatory agents, although cross-reactivity with other steroid hormone receptors such as the The dissociation of transactivation from transrepression at the glucocorticoid receptor is believed to be an approach toward improving the side-effect profile related to steroid therapy. The beneficial anti-inflammatory activity of GR modulators, such as steroids, is believed to occur through the transrepression of genes encoding for proinflammatory cytokines, adhesion molecules and enzymes. Many of the undesireable side-effects associated with such agents are believed to occur through the transactivation, or induction, of gene transcription leading to the downstream perturbation of homeostatic endocrine function. Some of these affected metabolic processes include induced gluconeogenesis, induced amino acid degradation, osteoporosis, suppression of HPA axis, induction of secondary adrenal suppression, changes in electrolyte concentration, changes in lipid metabolism, growth retardation, impaired wound healing and skin thinning. Weak, partial and full agonism of GR related to transrepression and transactivation, including potential antagonism of the receptor regarding transactivation, may be applied to the treatment of inflammatory and autoimmune diseases such as rheumatoid arthritis and asthma. For recent reviews see: (a) *Recent Advances in Glucocorticoid Receptor Action*; Cato, A. C. B., Schacke, H., Asadullah, K., Eds.; Springer-Verlag: Berlin-Heidelberg, Germany, 2002. (b) Coghlan, M. J.; Elmore, S. W.; Kym, P. R.; Kort, M. E. In *Annual Reports in Medicinal Chemistry*; Doherty, A. M., Hagmann, W. K., Eds.; Academic Press: San Diego, Calif., USA, 2002; Vol. 37, Ch. 17, pp 167-176.

The present invention is directed to a novel class of compounds that are selective glucocorticoid receptor modulators that have potent anti-inflammatory and immunosuppressive activity and possess advantages over steroidal glucocorticoid ligands with respect to side effects, efficacy, toxicity and/or metabolism.

SUMMARY OF THE INVENTION

The present invention encompasses compounds of Formula I and Formula II:

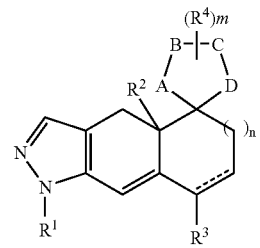

I

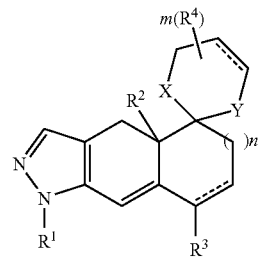

II or pharmaceutically acceptable salts or hydrates thereof, which are useful as selective glucocorticoid receptor ligands for treating a variety of autoimmune and inflammatory diseases or conditions.

DETAILED DESCRIPTION OF THE INVENTION

In one aspect, the present invention encompasses compounds of Formula I and Formula II:

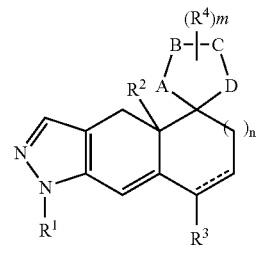

I

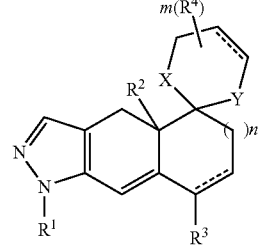

II or pharmaceutically acceptable salts or hydrates thereof, wherein
  dotted lines represent the presence of either a single or double bonds;
  m is 0, 1, 2 or 3,
  n is 0, 1 or 2;
  -A-B—C-D- is selected from the group consisting of:
  (1) —$CH_2$—$CH_2$—$CH_2$—O—,
  (2) —$CH_2$—$CH_2$—C(O)—O—, (3) —CH=CH—C(O)—O—,
(4) —O—CH$_2$—CH$_2$—CH$_2$—,
(5) —O—C(O)—CH$_2$—CH$_2$—,
(6) —HC=CH—CH$_2$—O—,
(7) —CH$_2$—HC=CH—O—,
(8) —CH$_2$—CH$_2$—C(O)—NH—,
(9) —CH$_2$—NH—CH$_2$—CH$_2$—,
(10) —CH$_2$—NH—C(O)—O—,
(11) —NH—C(O)—NH—C(O)—,
(12) —C(O)—NH—C(O)—NH—,
(13) —NH—C(O)—NH—CH$_2$—,
(14) —NH—C(O)—NH—C(=S)—,
(15) —O—CH$_2$—CH$_2$—O—,
(16) —S—CH$_2$—CH$_2$—S—;

provided that when the atoms at positions B and C of -A-B—C-D- are both carbon atoms, said atoms may be joined together to form a ring selected from

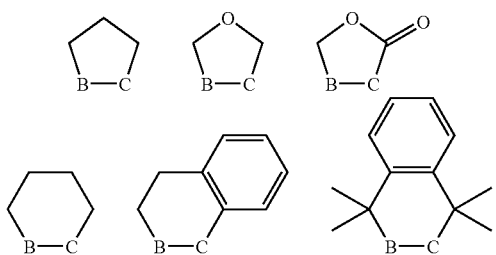

X and Y are each independently selected from CH$_2$, S and O;
R$^1$ is selected from the group consisting of:
(1) C$_{1-6}$alkyl,
(2) C$_{2-6}$alkenyl,
(3) C$_{2-6}$akynyl,
(4) C$_{3-6}$cycloalkyl,
(5) aryl,
(6) —CH$_2$-phenyl,
(7) HET, wherein items (1) to (3) above are optionally substituted from one to three substituents independently selected from the group consisting of: halo, OR$^5$, and NHR$^6$, and items (4) to (7) are optionally substituted with from one to three substituents selected from the group consisting of: halo, IR$^5$, NHR$^6$, C$_{1-3}$alkyl, C$_{2-6}$alkenyl, C$_{2-6}$akynyl;

R$^2$ and R$^3$ are each independently selected from the group consisting of:
(1) hydrogen,
(2) halo,
(3) C$_{1-6}$alkyl,
(4) C$_{2-6}$alkenyl,
(5) C$_{2-6}$akynyl,
(6) OR$^7$,
(7) NHR$_8$,
(8) aryl,
(9) —CH$_2$-phenyl;

R$^5$, R$^6$, R$^7$ and R$^8$ are each independently selected from the group consisting of:
(1) hydrogen,
(2) methyl;

each R$^4$ is independently selected from the group consisting of (1) —OH,
(2) —C$_{1-6}$alkyl optionally substituted with 1, 2 or 3 substituents selected independently from hydroxy, oxo, —COOH, amino, methylamino, dimethylamino, =S, and halo,
(3) C$_{2-6}$alkenyl optionally substituted with 1, 2 or 3 substituents selected independently from hydroxy, halo and —C(O)—O—C$_{1-2}$alkyl,
(4) C$_{2-6}$alkynyl optionally substituted with 1, 2 or 3 substituents selected independently from hydroxy and halo,
(5) phenyl optionally substituted with 1, 2 or 3 substituents selected independently from hydroxy, C$_{1-2}$alkyl, —COOH, —C(O)—O—CH$_3$ and halo,
(6) —C$_{1-2}$alkyl-phenyl optionally substituted with 1, 2 or 3 substituents independently selected from hydroxy, C$_{1-2}$alkyl and halo,
(7) —CO$_2$H,
(8) —CO$_2$C$_{1-3}$alkyl,
(9) —OC$_{1-3}$alkyl,
(10) —SO$_2$-C$_{1-3}$alkyl,
(11) —SO$_2$-phenyl optionally substituted with 1, 2 or 3 substituents independently selected from hydroxy, C$_{1-2}$alkyl and halo
(12) —C$_{1-2}$alkyl-O—C$_{1-2}$alkyl,
(13) —C$_{1-2}$alkyl-O—C$_{2-4}$alkenyl,
(14) —C$_{1-2}$alkyl-O-phenyl optionally substituted with with 1, 2 or 3 substituents independently selected from hydroxy, C$_{1-2}$alkyl and halo,
(15) —C$_{1-2}$alkyl-C(O)O—C$_{1-2}$alkyl,
(16) 2-(1,3-dioxan)ethyl,
(17) —C$_{1-2}$alkyl-C(O)—NH-phenyl,
(18) —C$_{1-2}$alkyl-C(O)—NHN.

Within this aspect there is a genus of compounds wherein m is 0, 1 or 2.

Within this aspect, there is another genus of compounds wherein n is 0 or 1.

Within this aspect, there is another genus of compounds wherein R$^2$ and R$^3$ are each individually hydrogen or methyl.

Within this apsect, there is another genus of compounds wherein each R$^4$ is independently selected from the group consisting of
(1) —OH,
(2) —C$_{1-6}$alkyl optionally substituted with 1, 2 or 3 substituents selected independently from hydroxy, oxo, —COOH, amino, methylamino, dimethylamino, thio, and halo,
(3) C$_{2-6}$alkenyl optionally substituted with 1, 2 or 3 substituents selected independently from hydroxy, halo and —C(O)—O—C$_{1-2}$alkyl,
(4) phenyl optionally substituted with 1, 2 or 3 substituents selected independently from hydroxy, C$_{1-2}$alkyl, —COOH, —C(O)—O—CH$_3$ and halo,
(5) —C$_{1-2}$alkyl-phenyl optionally substituted with 1, 2 or 3 substituents independently selected from hydroxy, C$_{1-2}$alkyl and halo,
(6) —SO$_2$—C$_{1-3}$alkyl, and
(7) —C$_{1-2}$alkyl-OC$_{1-2}$alkyl.

Within this aspect, there is another genus of compounds wherein R$^1$ is phenyl or pyridyl said phenyl or pyridyl or optionally mono or di-substituted with a substituent independently selected from the group consisting of:
(a) halo,
(b) OCH$_3$,
(d) CH$_3$,
(e) CN.

Within this genus, there is a subgenus of compounds wherein $R^1$ is phenyl, optionally mono or di-substituted with halo.

Within this aspect there is a genus of compounds of Formula I wherein

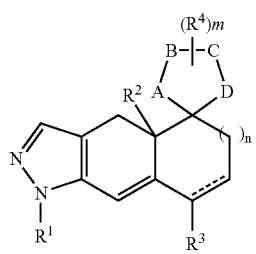

I m is 0, 1, 2 or 3;
n is 0 or 1;
$R^1$ is phenyl or pyridyl, said phenyl or pyridyl or optionally mono or di-substituted with a substituent independently selected from the group consisting of:
 (a) halo,
 (b) $OCH_3$,
 (d) $CH_3$,
 (e) CN; and $R^2$ and $R^3$ are each individually hydrogen or methyl.

Within this genus, there is a sub-genus of compounds wherein each $R^4$ is independently selected from the group consisting of
 (1) —OH,
 (2) —$C_{1-6}$alkyl optionally substituted with 1, 2 or 3 substituents selected independently from hydroxy, oxo, —COOH, amino, methylamino, dimethylamino, thio, and halo,
 (3) $C_{2-6}$alkenyl optionally substituted with 1, 2 or 3 substituents selected independently from hydroxy, halo and —C(O)—O—$C_{1-2}$alkyl,
 (4) phenyl optionally substituted with 1, 2 or 3 substituents selected independently from hydroxy, $C_{1-2}$alkyl, —COOH, —C(O)—O—$CH_3$ and halo,
 (5) —$C_{1-2}$alkyl-phenyl optionally substituted with 1, 2 or 3 substituents independently selected from hydroxy, $C_{1-2}$alkyl and halo,
 (6) —$SO_2$—$C_{1-3}$alkyl, and
 (7) —$C_{1-2}$alkyl-O$C_{1-2}$alkyl.

Within this sub-genus, there is a class of compounds wherein -A-B—C-D- is selected from the group consisting of:
 (1) —$CH_2$—$CH_2$—$CH_2$—O—,
 (2) —CH=CH—$CH_2$—O—,
 (3) —$CH_2$—CH=CH—O—,
 (4) —O—$CH_2$—$CH_2$—$CH_2$—,
 (5) —O—$CH_2$—$CH_2$—O—,
 (6) —S—$CH_2$—$CH_2$—S—,
 (7) —$CH_2$—NH—$CH_2$—$CH_2$—, and
 (8) —$CH_2$—NH—C(O)—O—;

$R^1$ is phenyl optionally mono or di-substituted with halo.

Within this aspect, there is a genus of compounds of Formula II

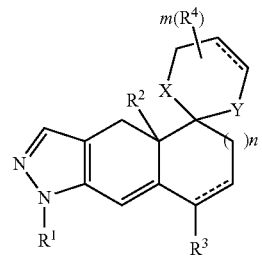

II

Wherein
m is 0, 1 or 2;
n is 0 or 1;
$R^1$ is phenyl or pyridyl said phenyl or pyridyl or optionally mono or di-substituted with a substituent independently selected from the group consisting of:
 (a) halo,
 (b) $OCH_3$,
 (d) $CH_3$,
 (e) CN; and $R^2$ and $R^3$ are each individually hydrogen or methyl.

Within this genus, there is a sub-genus of compounds wherein each $R^4$ is independently selected from the group consisting of —$C_{1-6}$alkyl or hydrogen;

Within this genus, there is a subgenus of compounds wherein X and Y are both O or are both S or X is O and Y is $CH_2$;
$R^1$ is phenyl optionally mono or di-substituted with halo.

Another aspect of the invention encompasses a pharmaceutical composition comprising a compound of Formula I or Formula II in combination with a pharmaceutically acceptable carrier.

Another aspect of the invention encompasses a method for treating a glucocorticoid receptor mediated disease or condition in a mammalian patient in need of such treatment comprising administering the patient a compound of Formula I in an amount that is effective for treating the glucocorticoid receptor mediated disease or condition.

Within this aspect is encompassed the above method wherein the glucocorticoid receptor mediated disease or condition is selected from the group consisting of: tissue rejection, leukemias, lymphomas, Cushing's syndrome, acute adrenal insufficiency, congenital adrenal hyperplasia, rheumatic fever, polyarteritis nodosa, granulomatous polyarteritis, inhibition of myeloid cell lines, immune proliferation/apoptosis, HPA axis suppression and regulation, hypercortisolemia, stroke and spinal cord injury, hypercalcemia, hypergylcemia, acute adrenal insufficiency, chronic primary adrenal insufficiency, secondary adrenal insufficiency, congenital adrenal hyperplasia, cerebral edema, thrombocytopenia, Little's syndrome, obesity, metabolic syndrome, inflammatory bowel disease, systemic lupus erythematosus, polyartitis nodosa, Wegener's granulomatosis, giant cell arteritis, rheumatoid arthritis, juvenile rheumatoid arthritis, uveitis, hay fever, allergic rhinitis, urticaria, angioneurotic edema, chronic obstructive pulmonary disease, asthma, tendonitis, bursitis, Crohn's disease, ulcerative colitis, autoimmune chronic active hepatitis, organ transplantation, hepatitis, cirrhosis, inflammatory scalp alopecia, panniculitis, psoriasis, discoid lupus erythematosus, inflamed cysts, atopic dermatitis, pyoderma gangrenosum, pemphigus vulgaris, buflous pemphigoid, systemic lupus erythematosus, dermatomyositis, herpes gestationis, eosinophilic fasciitis, relapsing polychondritis, inflammatory vasculitis, sarcoidosis, Sweet's disease, type I reactive leprosy, capillary hemangiomas, contact dermatitis, atopic dermatitis, lichen planus, exfoliative dermatitis, erythema nodosum, acne, hirsutism, toxic epidermal necrolysis, erythema multiform, cutaneous T-cell lymphoma, Human Immunodeficiency Virus (HIV), cell apoptosis, cancer, Kaposi's sarcoma, retinitis pigmentosa, cognitive performance, memory and learning enhancement, depression, addiction, mood disorders, chronic fatigue syndrome, schizophrenia, sleep disorders, and anxiety.

Another aspect of the invention encompasses a method of selectively modulating the activation, repression, agonism and antagonism effects of the glucocorticoid receptor in a mammal comprising administering to the mammal a compound of Formula I or Formula II in an amount that is effective to modulate the glucocorticoid receptor and minimizes side effects.

Exemplifying the invention are the compounds of the Examples disclosed hereunder.

The invention is described using the following definitions unless otherwise indicated.

The term "halogen" or "halo" includes F, Cl, Br, and I.

The term "alkyl" means linear or branched structures and combinations thereof, having the indicated number of carbon atoms. Thus, for example, $C_{1-6}$alkyl includes methyl, ethyl, propyl, 2-propyl, s- and t-butyl, butyl, pentyl, hexyl, 1,1-dimethylethyl, cyclopropyl, cyclobutyl, cyclopentyl and cyclohexyl.

The term "alkoxy" means alkoxy groups of a straight, branched or cyclic configuration having the indicated number of carbon atoms. $C_{1-6}$alkoxy, for example, includes methoxy, ethoxy, propoxy, isopropoxy, and the like.

The term "alkylthio" means alkylthio groups having the indicated number of carbon atoms of a straight, branched or cyclic configuration. $C_{1-6}$alkylthio, for example, includes methylthio, propylthio, isopropylthio, and the like.

The term "alkenyl" means linear or branched structures and combinations thereof, of the indicated number of carbon atoms, having at least one carbon-to-carbon double bond, wherein hydrogen may be replaced by an additional carbon-to-carbon double bond. $C_{2-6}$alkenyl, for example, includes ethenyl, propenyl, 1-methylethenyl, butenyl and the like.

The term "alkynyl" means linear or branched structures and combinations thereof, of the indicated number of carbon atoms, having at least one carbon-to-carbon triple bond. $C_{3-6}$alkynyl, for example, includes propenyl, 1-methylethenyl, butenyl and the like.

The term "cycloalkyl" means mono-, bi- or tricyclic structures, optionally combined with linear or branched structures, the indicated number of carbon atoms. Examples of cycloalkyl groups include cyclopropyl, cyclopentyl, cycloheptyl, adamantyl, cyclododecylmethyl, 2-ethyl-1-bicyclo[4.4.0]decyl, and the like.

The term "aryl" is defined as a mono- or bi-cyclic aromatic ring system and includes, for example, phenyl, naphthyl, and the like.

The term "aralkyl" means an alkyl group as defined above of 1 to 6 carbon atoms with an aryl group as defined above substituted for one of the alkyl hydrogen atoms, for example, benzyl and the like.

The term "aryloxy" means an aryl group as defined above attached to a molecule by an oxygen atom (aryl-O) and includes, for example, phenoxy, naphthoxy and the like.

The term "aralkoxy" means an aralkyl group as defined above attached to a molecule by an oxygen atom (aralkyl-O) and includes, for example, benzyloxy, and the like.

The term "arylthio" is defined as an aryl group as defined above attached to a molecule by an sulfur atom (aryl-S) and includes, for example, thiophenyoxy, thionaphthoxy and the like.

The term "aroyl" means an aryl group as defined above attached to a molecule by an carbonyl group (aryl-C(O)—) and includes, for example, benzoyl, naphthoyl and the like.

The term "aroyloxy" means an aroyl group as defined above attached to a molecule by an oxygen atom (aroyl-O) and includes, for example, benzoyloxy or benzoxy, naphthoyloxy and the like.

The term "HET" is defined as a 5- to 10-membered aromatic, partially aromatic or non-aromatic mono- or bicyclic ring, containing 14 heteroatoms selected from O, S and N, and optionally substituted with 1-2 oxo groups. Preferably, "HET" is a 5- or 6-membered aromatic or non-aromatic monocyclic ring containing 1-3 heteroatoms selected from O, S and N, for example, pyridine, pyrimidine, pyridazine, furan, thiophene, thiazole, oxazole, isooxazole and the like, or HET is a 9- or 10-membered aromatic or partially aromatic bicyclic ring containing 1-3 heteroatoms selected from O, S, and N, for example, benzofuran, benzothiophene, indole, pyranopyrrole, benzopyran, quionoline, benzocyclohexyl, naphtyridine and the like. "HET" also includes the following: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrinidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl.

The term "treating" encompasses not only treating a patient to relieve the patient of the signs and symptoms of the disease or condition but also prophylactically treating an asymptomatic patient to prevent the onset of the disease or condition or preventing, slowing or reversing the progression of the disease or condition. The term "amount effective for treating" is intended to mean that amount of a drug or pharmaceutical agent that will elicit the biological or medical response of a tissue, a system, animal or human that is being sought by a researcher, veterinarian, medical doctor or other clinician. The term also encompasses the amount of a pharmaceutical drug that will prevent or reduce the risk of occurrence of the biological or medical event that is sought to be prevented in a tissue, a system, animal or human by a researcher, veterinarian, medical doctor or other clinician.

The following abbreviations have the indicated meanings:

| | |
|---|---|
| AIBN = | 2.2'-azobisisobutyronitrile |
| 9-BBN = | 9-borabicyclo[3.3.1]nonane |
| B.P. = | benzoyl peroxide |
| Bn = | benzyl |
| CCl$_4$= | carbon tetrachloride |

-continued

| | |
|---|---|
| DAST = | diethylamine sulfur trifluoride |
| DCC = | dicyclohexyl carbodiimide |
| DCI = | 1-(3-dimethylaminopropyl)-3-ethyl carbodiimide |
| DEAD = | diethyl azodicarboxylate |
| Dess-Martin periodinane = | [1,1,1-tris(acetyloxy)-1,1-dihydro-1,2-benziodoxol-3-(1H)-one] |
| DIBAL = | diisobutyl aluminum hydride |
| DME = | ethylene glycol dimethylether |
| DMAP = | 4-(dimethylamino)pyridine |
| DMF = | N,N-dimethylformamide |
| DMSO = | dimethyl sulfoxide |
| $Et_3N$ = | triethylamine |
| HMPA = | hexamethylphosphoramide |
| HPLC = | high performance liquid chromatography |
| LCMS = | tandem HPLC followed by MS |
| MS = | mass spectrum (or mass spectroscopy) |
| LDA = | lithium diisopropylamide |
| m-CPBA = | metachloroperbenzoic acid |
| NBS = | N-bromosuccinimide |
| NMR = | nuclear magnetic resonance |
| NSAID = | non-steroidal anti-inflammatory drug |
| PCC = | pyridinium chlorochromate |
| PDC = | pyridinium dichromate |
| Ph = | phenyl |
| 1,2-Ph = | 1,2-benzenediyl |
| Pyr = | pyridine |
| Qn = | 7-chloroquinolin-2-yl |
| $R^S$= | —$CH_2SCH_2CH_2Ph$ |
| r.t. = | room temperature |
| rac. = | racemic |
| THF = | tetrahydrofuran |
| THP = | tetrahydropyran-2-yl |
| TLC = | thin layer chromatography |

Alkyl Group Abbreviations

| | |
|---|---|
| Me = | methyl |
| Et = | ethyl |
| n-Pr = | normal propyl |
| i-Pr = | isopropyl |
| n-Bu = | normal butyl |
| i-Bu = | isobutyl |
| s-Bu = | secondary butyl |
| t-Bu = | tertiary butyl |
| c-Pr = | cyclopropyl |
| c-Bu = | cyclobutyl |
| c-Pen = | cyclopentyl |
| c-Hex = | cyclohexyl |

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

The pharmaceutical compositions of the present invention comprise a compound of Formula I or Formula II as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylarninoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic,-benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that in the discussion of methods of treatment which follows, references to the compounds of Formula I or Formula II are meant to also include the pharmaceutically acceptable salts.

The magnitude of prophylactic or therapeutic dose of a compound of Formula I or Formula II will, of course, vary with the nature and the severity of the condition to be treated and with the particular compound of Formula I or Formula II and its route of administration. It will also vary according to a variety of factors including the age, weight, general health, sex, diet, time of administration, rate of excretion, drug combination and response of the individual patient. In general, the daily dose from about 0.001 mg to about 100 mg per kg body weight of a mammal, preferably 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for oral administration to humans may contain from about 0.5 mg to about 5 g of active agent compounded with an appropriate and convenient amount of carrier material which may vary from about 5 to about 95 percent of the total composition. Dosage unit forms will generally contain from about 1 mg to about 2 g of an active ingredient, typically 25 mg, 50 mg, 100 mg, 200 mg, 300 mg, 400 mg, 500 mg, 600 mg, 800 mg, or 1000 mg.

For the treatment of glucocorticoid receptor mediated diseases the compound of Formula I and Formula II may be administered orally, topically, parenterally, by inhalation spray or rectally in dosage unit formulations containing conventional non-toxic pharmaceutically acceptable carriers, adjuvants and vehicles. The term parenteral as used herein includes subcutaneous, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, solutions, aqueous or oily suspensions, dispersible powders or granules, emulsions, hard or soft capsules, syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative, and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of Formula I or Formula II may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing a compound of Formula I or Formula II are employed. (For purposes of this application, topical application shall include mouth washes and gargles.) Topical formulations may generally be comprised of a pharmaceutical carrier, cosolvent, emulsifier, penetration enhancer, preservative system, and emollient.

The ability of the compounds of Formula I or Formula II to selectively modulate glucocorticoid receptors makes them useful for treating, preventing or reversing the progression of a variety of inflammatory-and autoimmune diseases and conditions. Thus, the compounds of the present invention are useful to treat, prevent or ameliorate the following diseases or conditions: inflammation, tissue rejection, auto-immunity, various malianancies, such as leukemias and lymphomas, Cushing's syndrome, acute adrenal insufficiency, congenital adrenal hyperplasia, rheumatic fever, polyarteritis nodosa, granulomatous polyarteritis, inhibition of myeloid cell lines, immune proliferation/apoptosis, HPA axis suppression and regulation, hypercortisolemia, stroke and spinal cord injury, hypercalcemia, hypergylcemia, acute adrenal insufficiency, chronic primary adrenal insufficiency, secondary adrenal insufficiency, congenital adrenal hyperplasia, cerebral edema, thrombocytopenia, Little's syndrome, obesity and metabolic syndrome.

The compounds of the present invention are also useful for treating, preventing or reversing the progression of disease states involving systemic inflammation such as inflammatory bowel disease, systemic lupus erythematosus, polyartitis nodosa, Wegener's granulomatosis, giant cell arteritis, rheumatoid arthritis, juvenile rheumatoid arthritis, uveitis, hay fever, allergic rhinitis, urticaria, angioneurotic edema, chronic obstructive pulmonary disease, asthma, tendonitis, bursitis, Crohn's disease, ulcerative colitis, autoimmune chronic active hepatitis, organ transplantation, hepatitis, and cirrhosis.

The compounds of the present invention are useful for treating, preventing or reversing the progression of a variety of topical diseases such as inflammatory scalp alopecia, panniculitis, psoriasis, discoid lupus erythematosus, inflamed cysts, atopic dermatitis, pyoderma gangrenosum, pemphigus vulgaris, buflous pernphigoid, systemic lupus erythematosus, dermatomyositis, herpes gestationis, eosinophilic fasciitis, relapsing polychondritis, inflammatory vasculitis, sarcoidosis, Sweet's disease, type I reactive leprosy, capillary hemangiomas, contact dermatitis, atopic dermatitis, lichen planus, exfoliative dermatitus, erythema nodosum, acne, hirsutism, toxic epidermal necrolysis, erythema multiform, cutaneous T-cell lymphoma.

The compounds of the present invention are also useful in treating, preventing or reversing the progression of disease states associated with Human Immunodeficiency Virus (HIV), cell apoptosis, and cancer including, but not limited to, Kaposi's sarcoma, immune system activation and modulation, desensitization of inflammatory responses, IIL-I expression, natural killer cell development, lymphocytic leukemia, and treatment of retinitis pigmentosa. Cogitive and behavioral processes are also susceptible to glucocorticoid therapy where antagonists would potentially be useful in the treatment of processes such as cognitive performance, memory and learning enhancement, depression, addiction, mood disorders, chronic fatigue syndrome, schizophrenia, stroke, sleep disorders, and anxiety.

The invention also encompasses a method for treating a glucocorticoid receptor mediated disease comprising concomitantly administering to a patient in need of such treatment a compound of Formula I or Formula II and one or additional more agents. For treating or preventing asthma or chronic obstructive pulmonary disease, the compounds of Formula I or Formula 1 may be combined with one or more agents selected from the group consisting of: θ-agonists (e.g., salmeterol), theophylline, anticholinergics (e.g., atropine and ipratropium bromide), cromolyn, nedocromil and leukotriene modifiers (e.g., montelukast). For treating or preventing inflammation, the compounds of Formula I or Formula II may be combined with one or the following: a salicylate, including acetylsalicylic acid, a non-steroidal antiinflammatory drug, including indomethacin, sulindac, mefenamic, meclofenamic, tolfenamic, tolmetin, ketorolac, dicofenac, ibuprofen, naproxen, fenoprofen, ketoprofen, flurbiprofin and oxaprozin, a TNF inhibitor, including etanercept and infliximab, an IL-1 receptor antagonist, including anakinra, a cytotoxic or immunosuppressive drug, including methotrexate, leflunomide, azathioprine and cyclosporine, a gold compound, hydroxychloroquine or sulfasalazine, penicillamine, darbufelone, and a ρ38 kinase inhibitor. The compound of Formula I or Formula II may also be used in combination with bisphonates such as alendronate to treat a glucocorticoid mediated disease and simultaneously inhibit osteoclast-mediated bone resorption.

Methods of Synthesis

The compounds of the invention are prepared by the following reaction schemes. All substituents are as defined above unless indicated otherwise.

Scheme 1

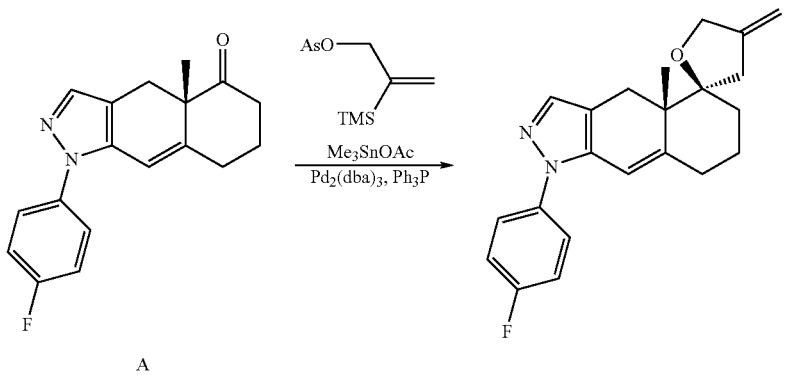

A

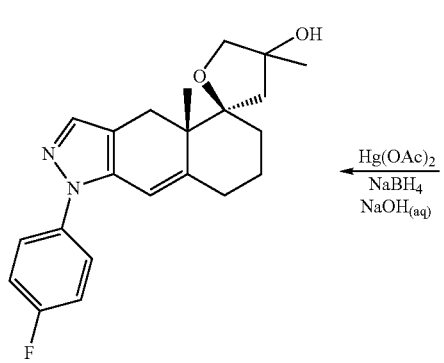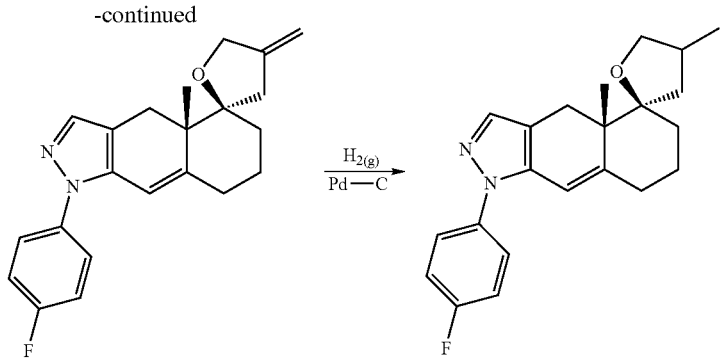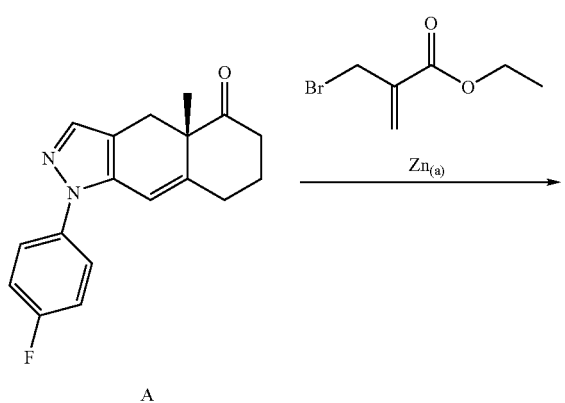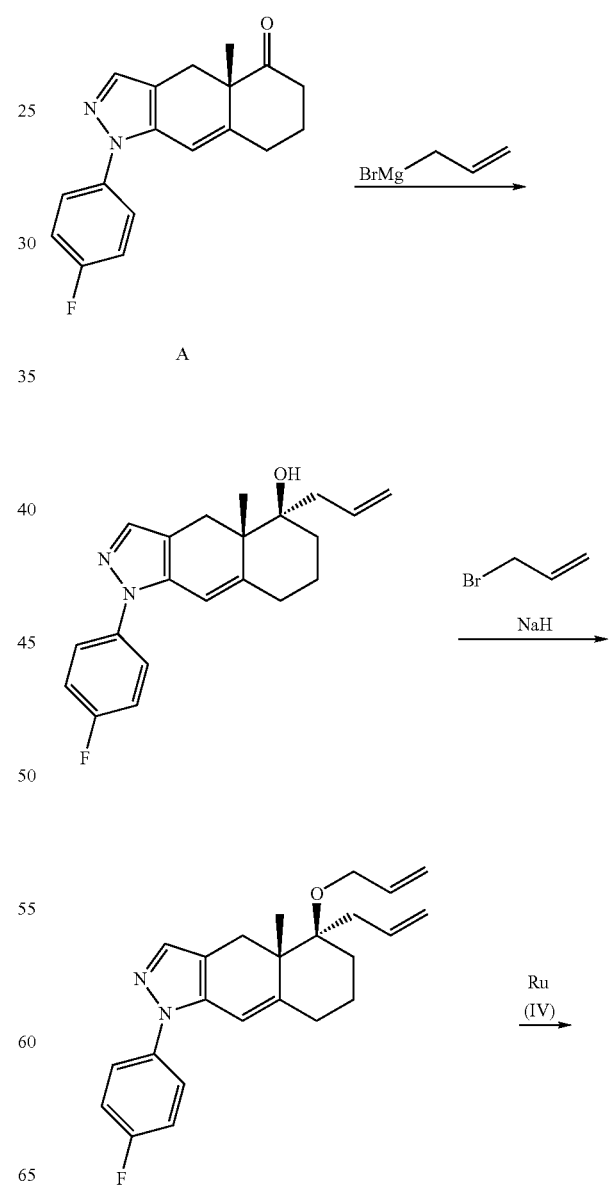

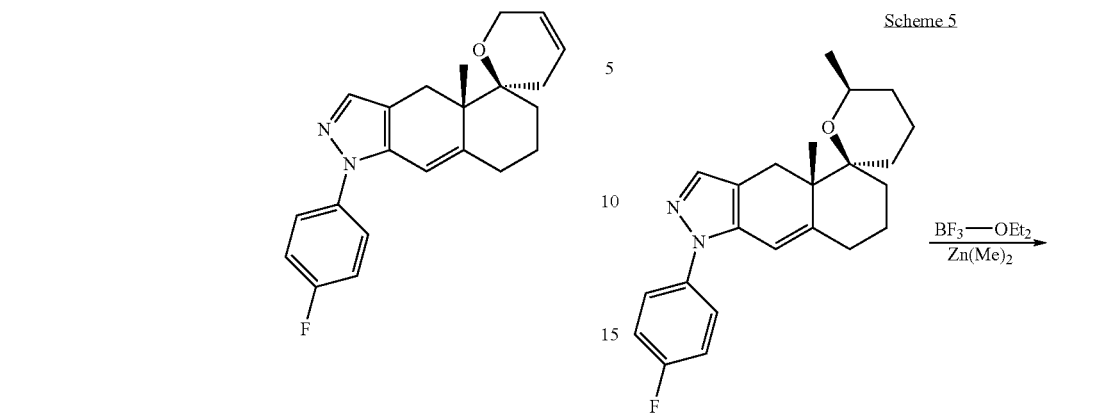
Scheme 4
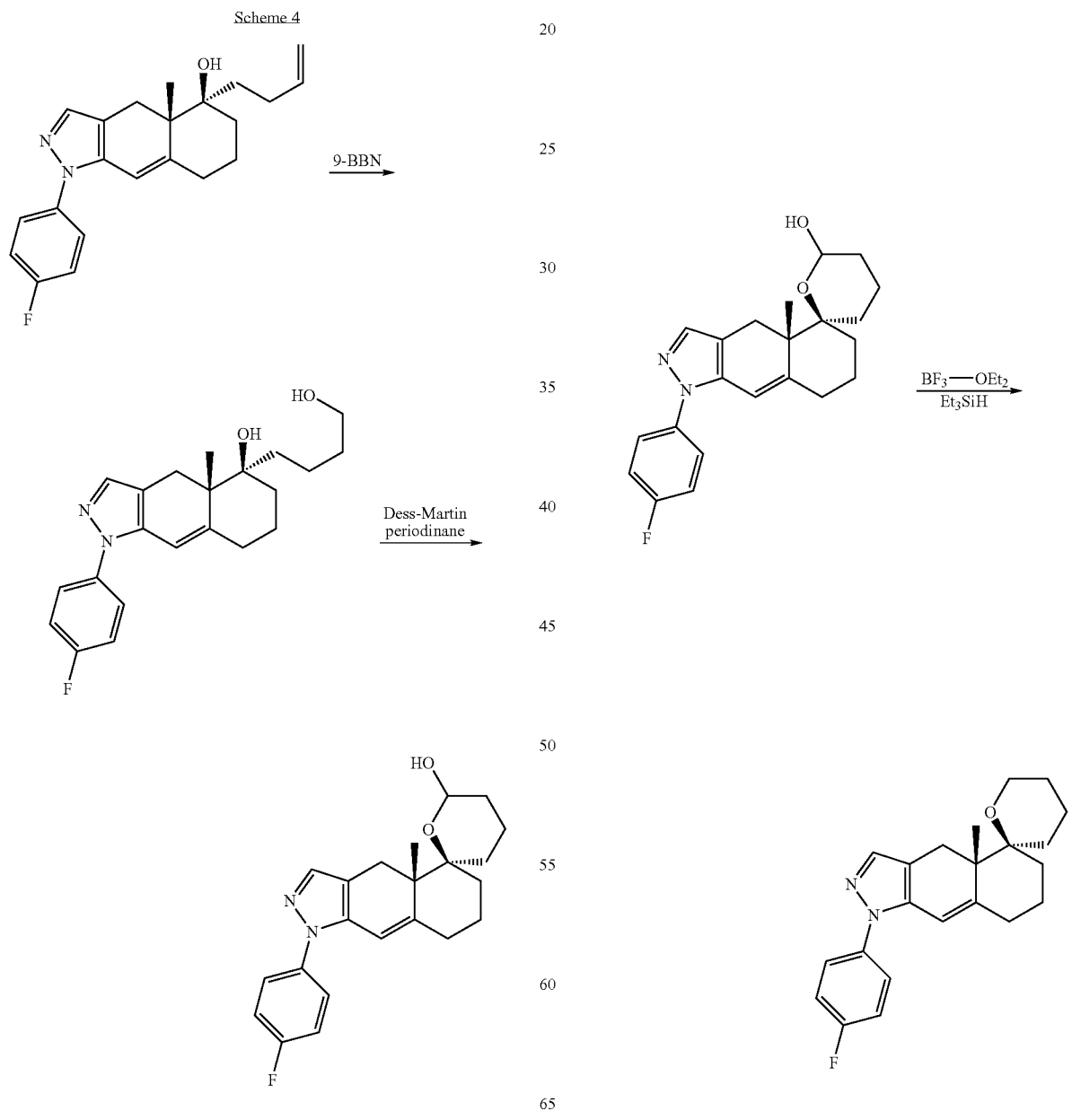
Scheme 5

Scheme 6
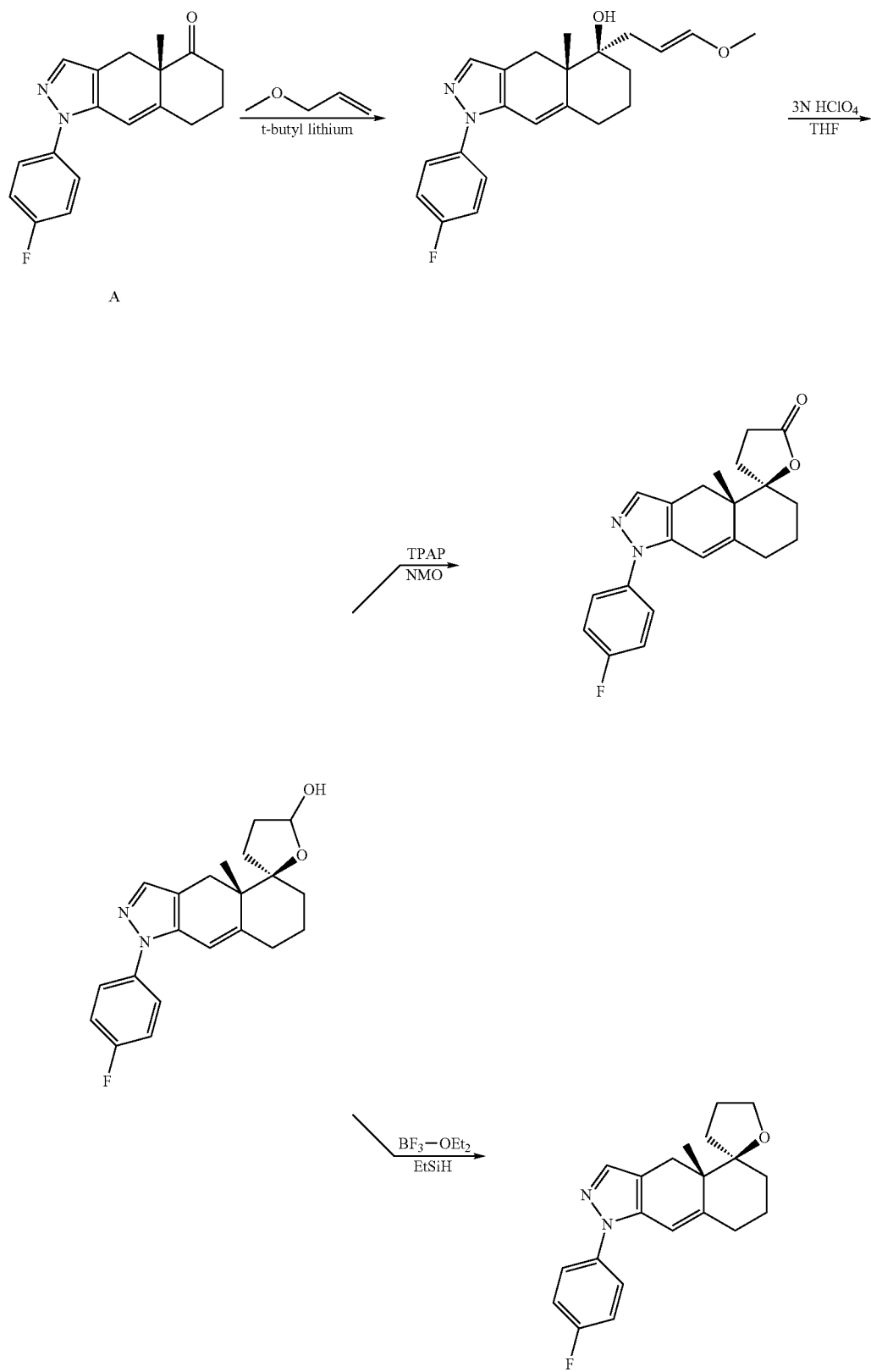

Scheme 7
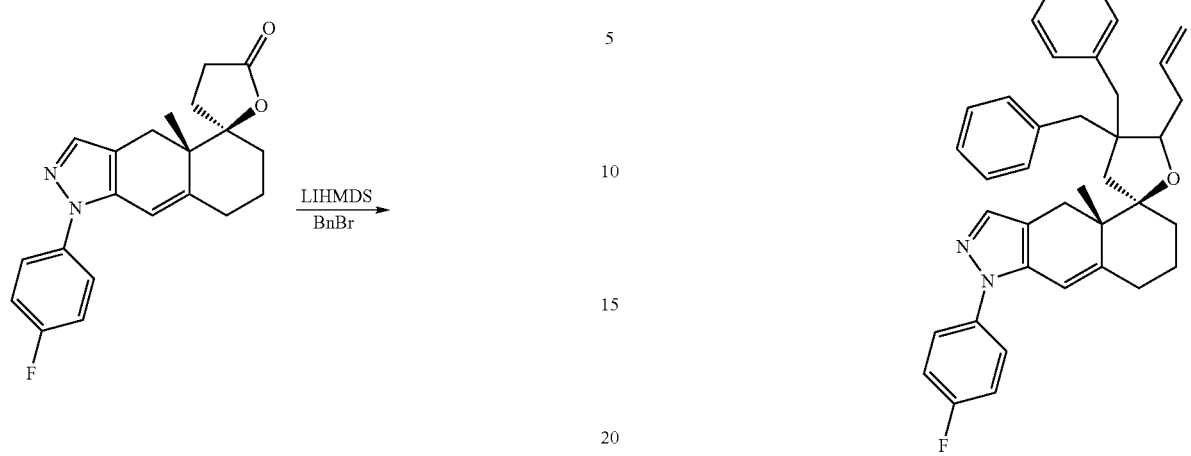
Scheme 8
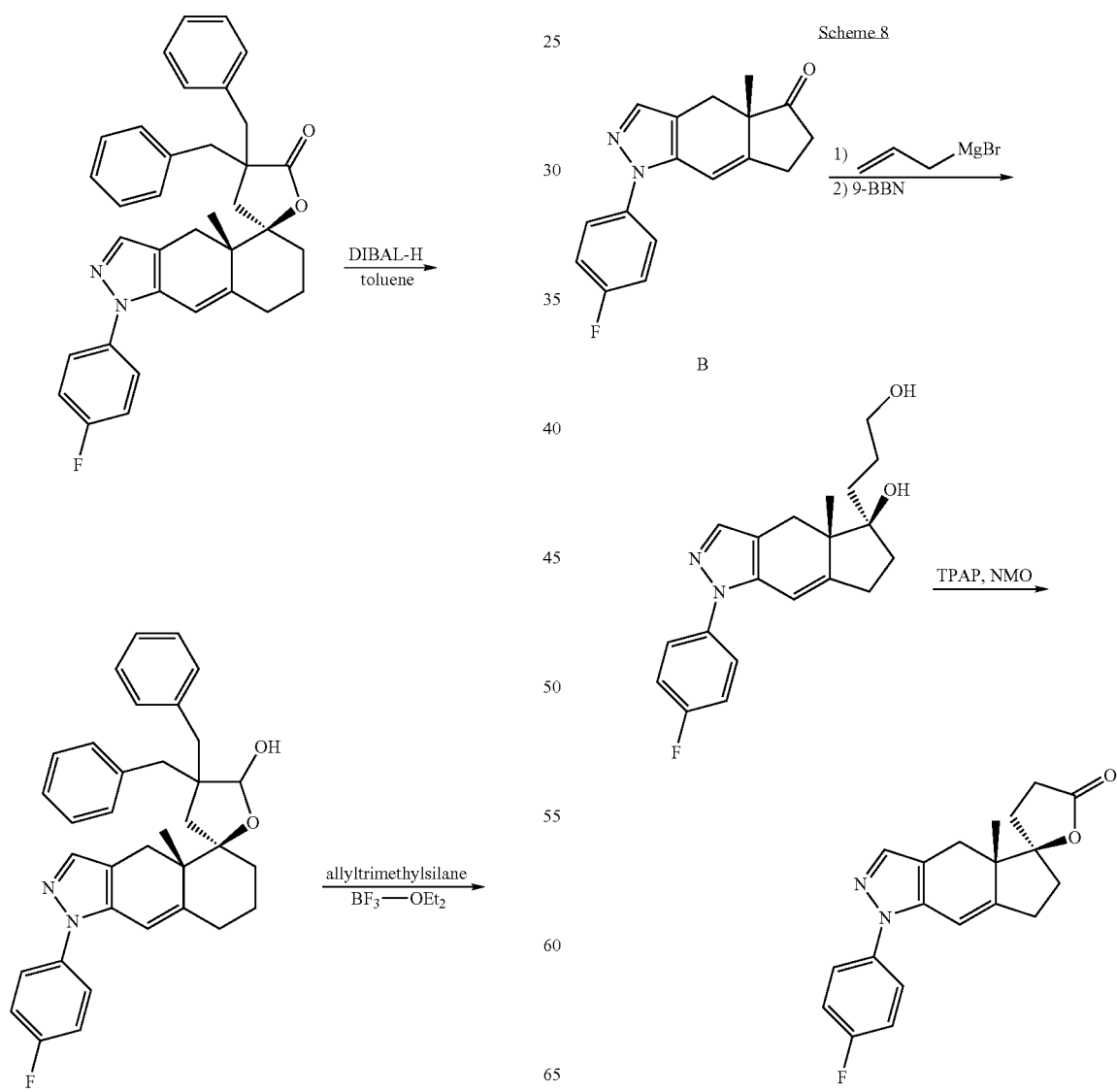

Scheme 9
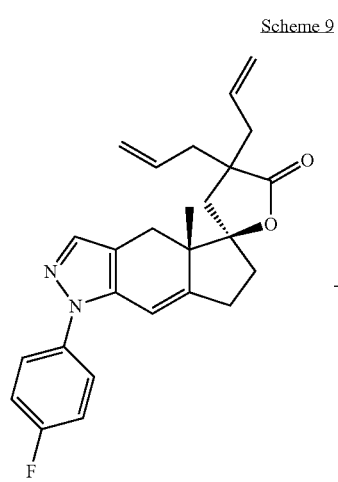
H<sub>2(g)</sub>, Pd—C
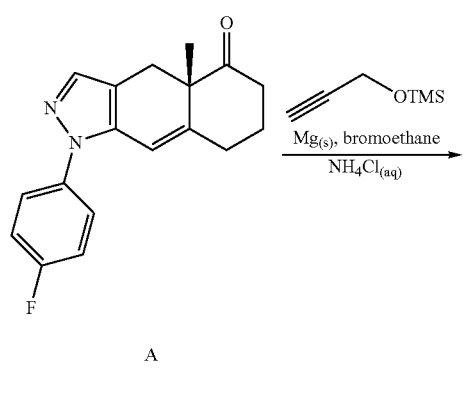
Scheme 10
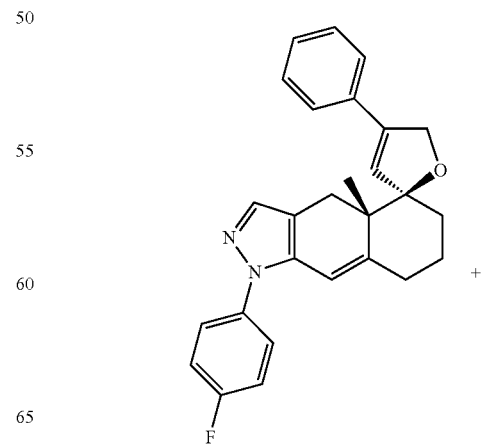
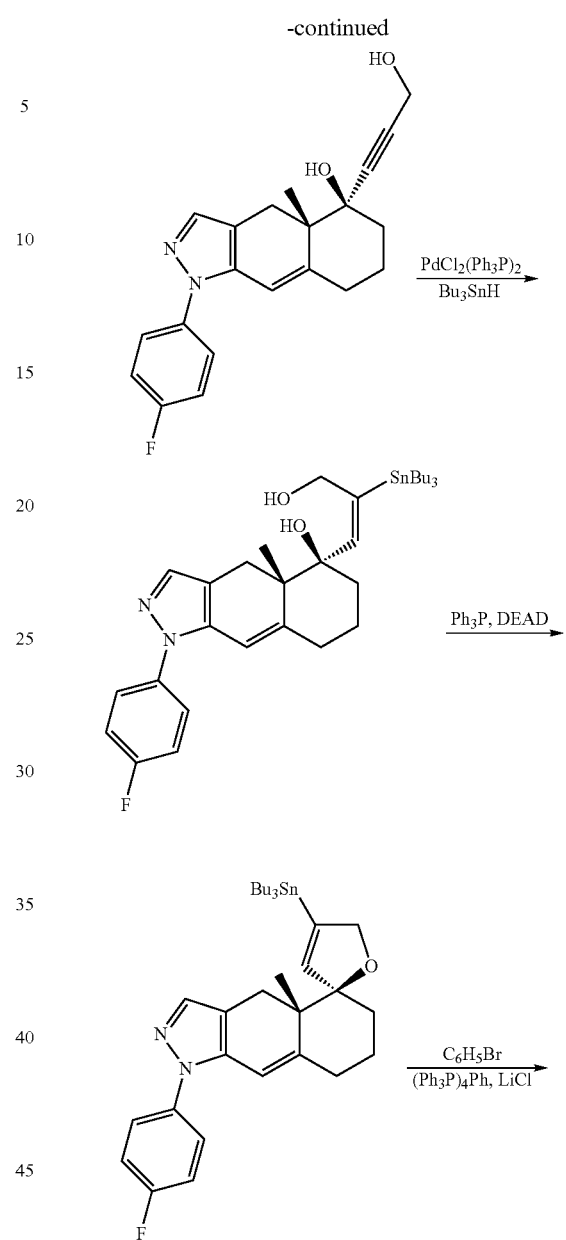

-continued
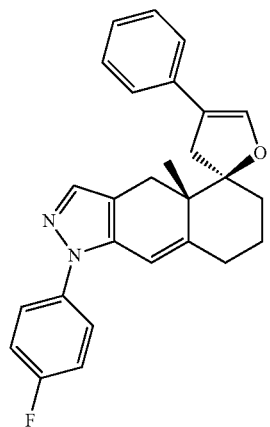
Scheme 11
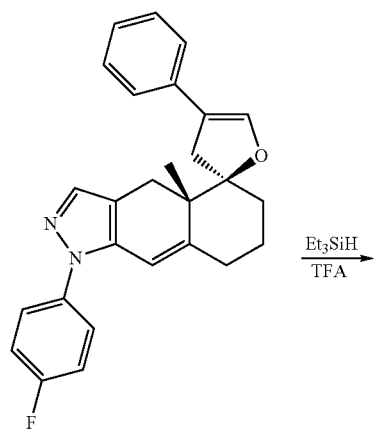
Et₃SiH
TFA
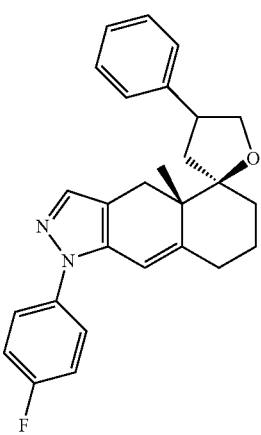
Scheme 12
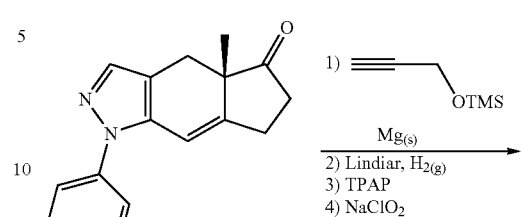
B
1) ≡—OTMS
   Mg(s)
2) Lindlar, H₂(g)
3) TPAP
4) NaClO₂
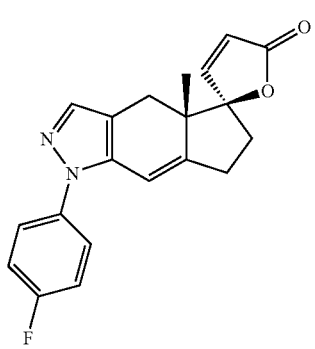
Scheme 13
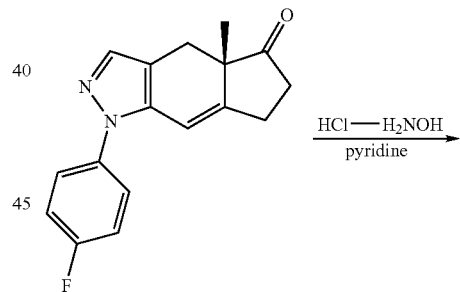
B
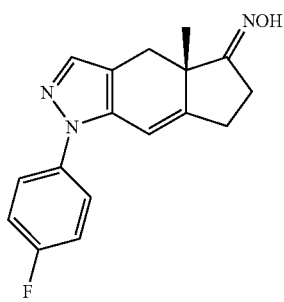
1) NBS, KHCO₃
   dioxane/H₂O
2) NaBH₄
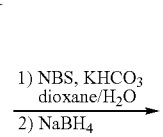

-continued
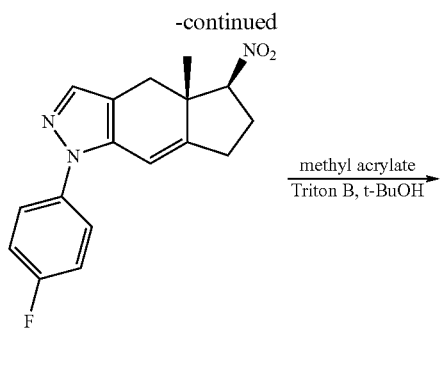
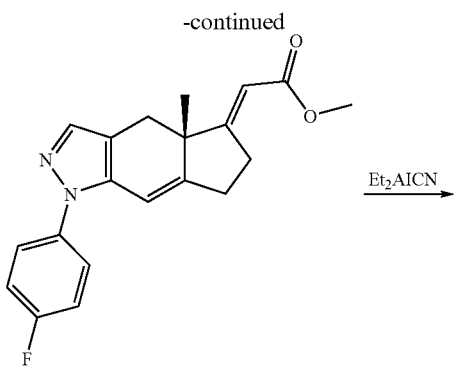
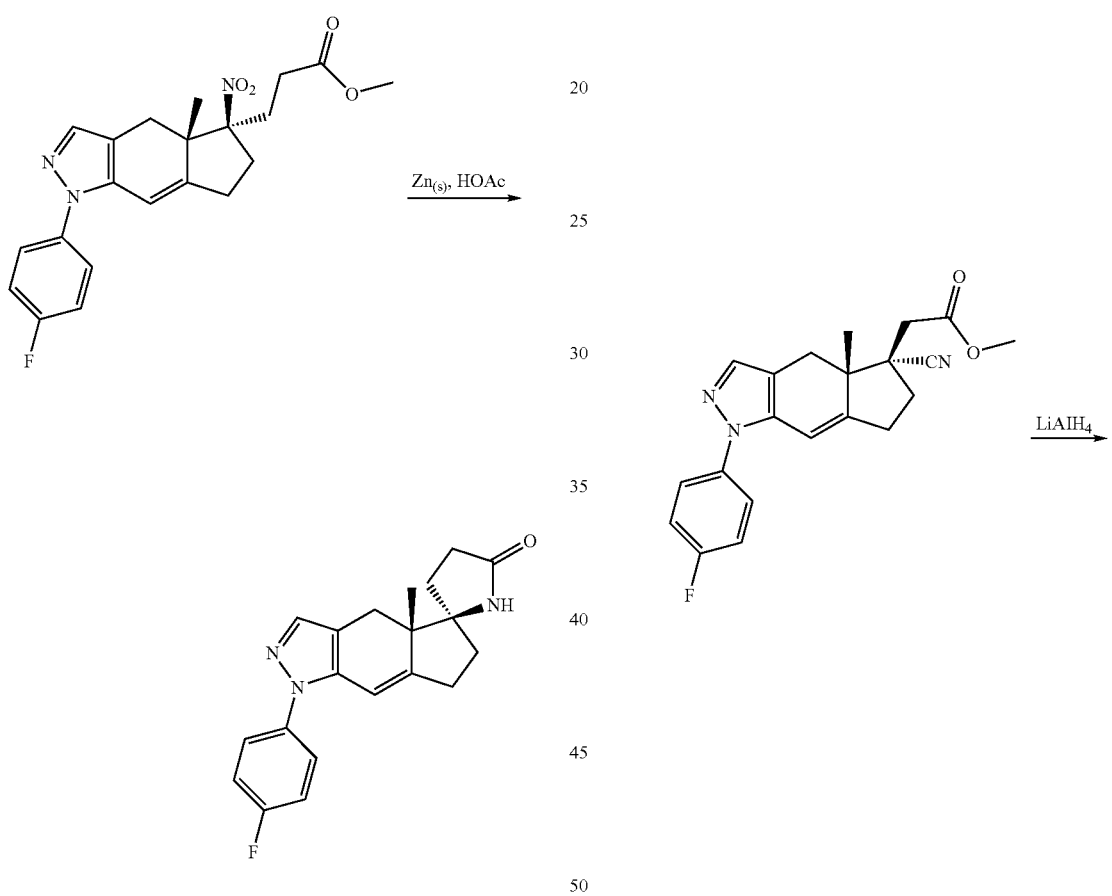
Scheme 14
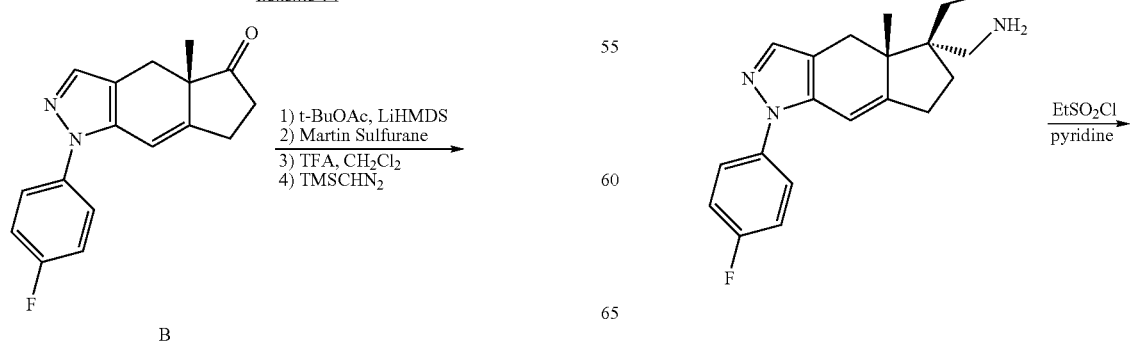

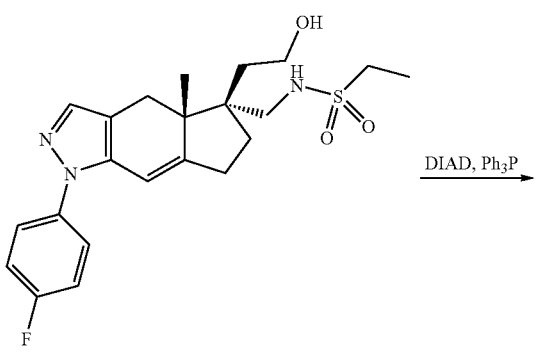 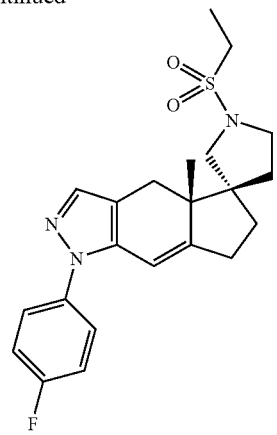
Scheme 15
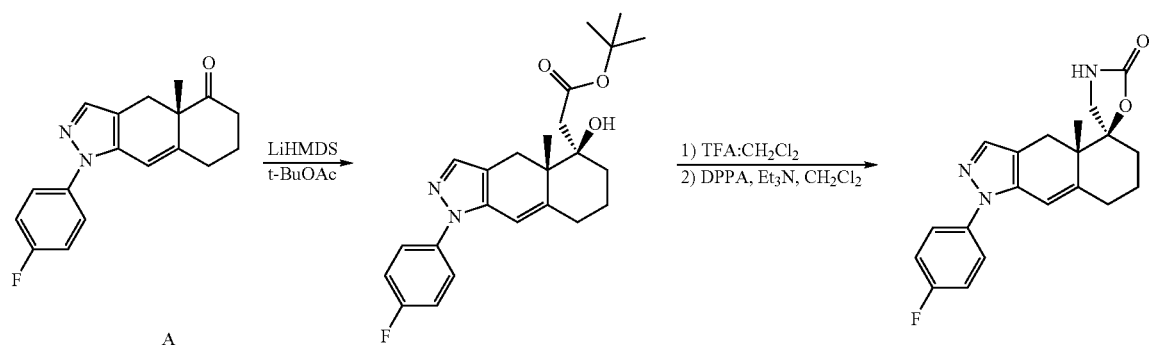
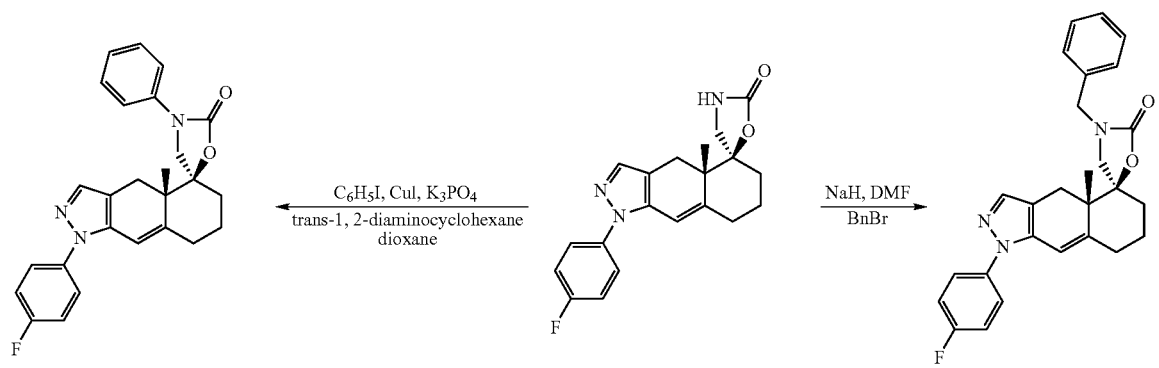

Scheme 16
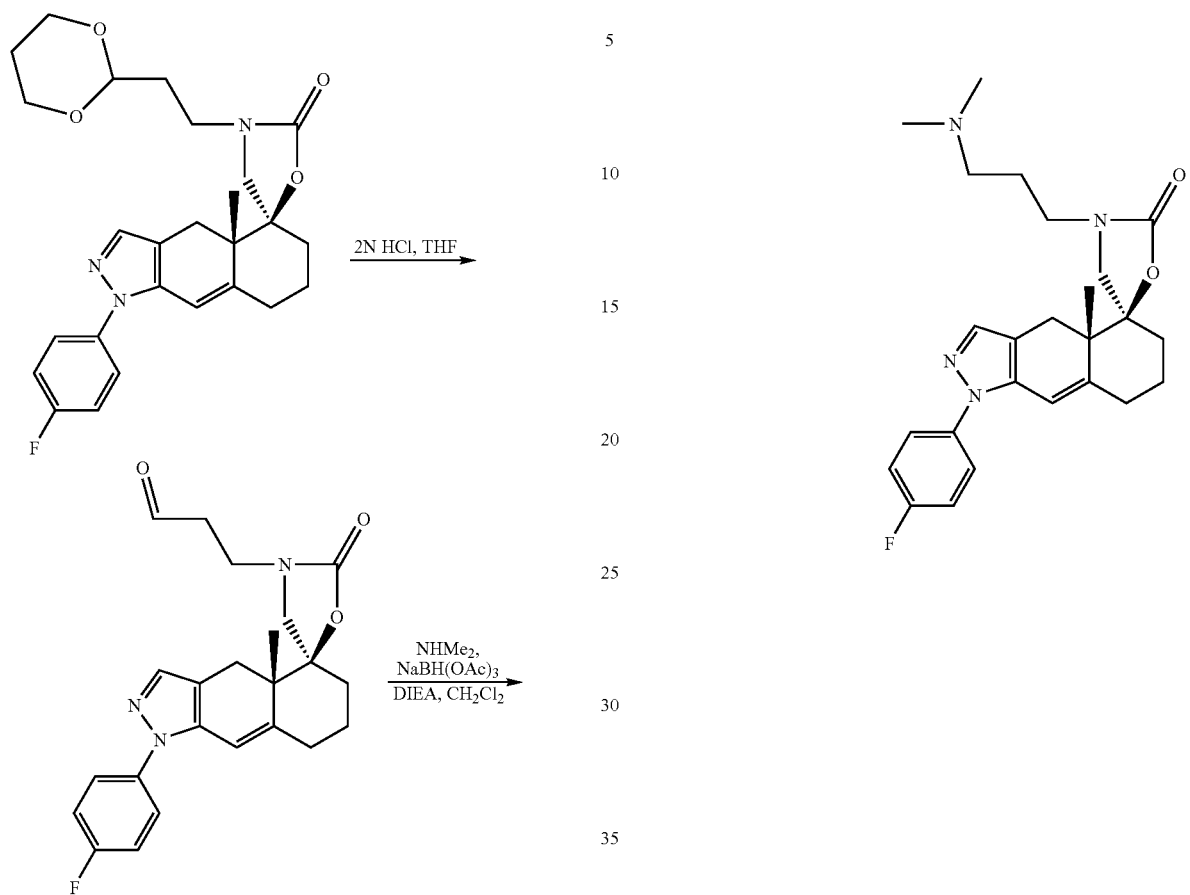
Scheme 17
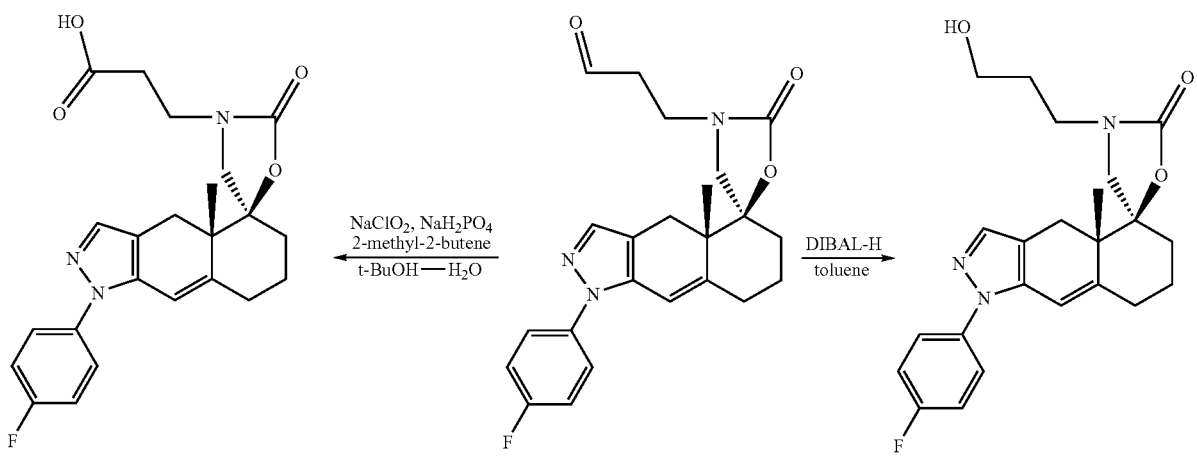

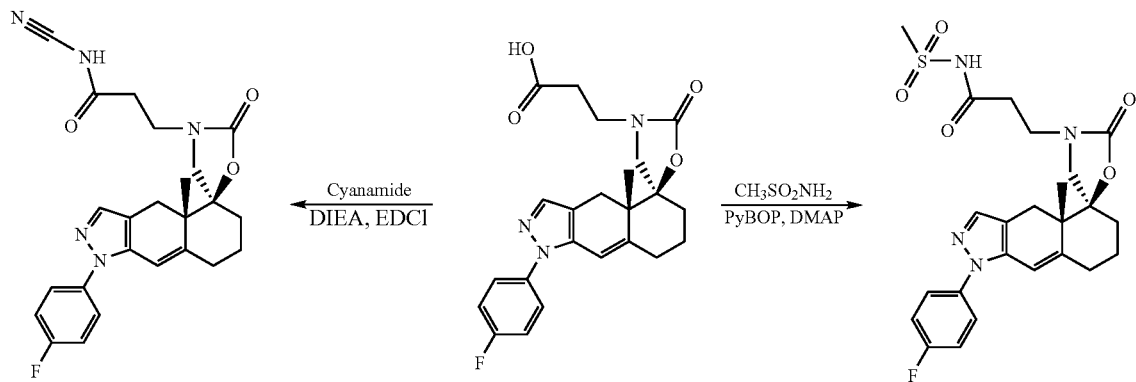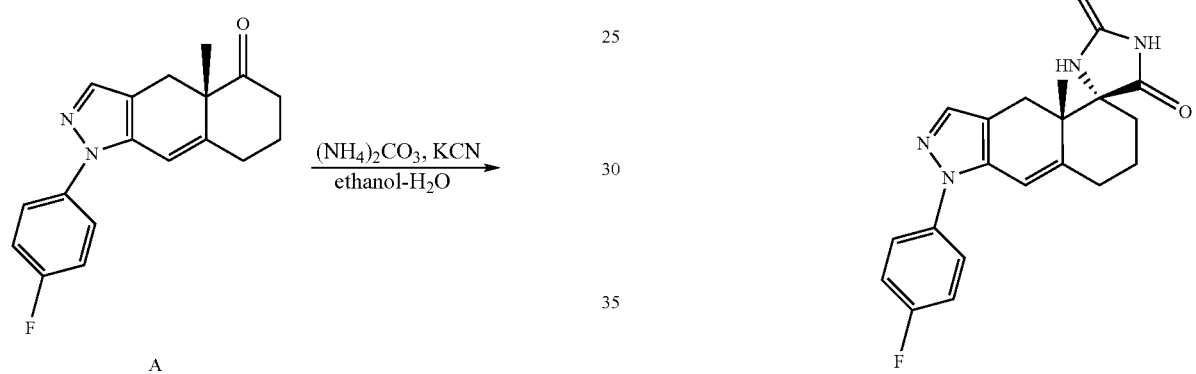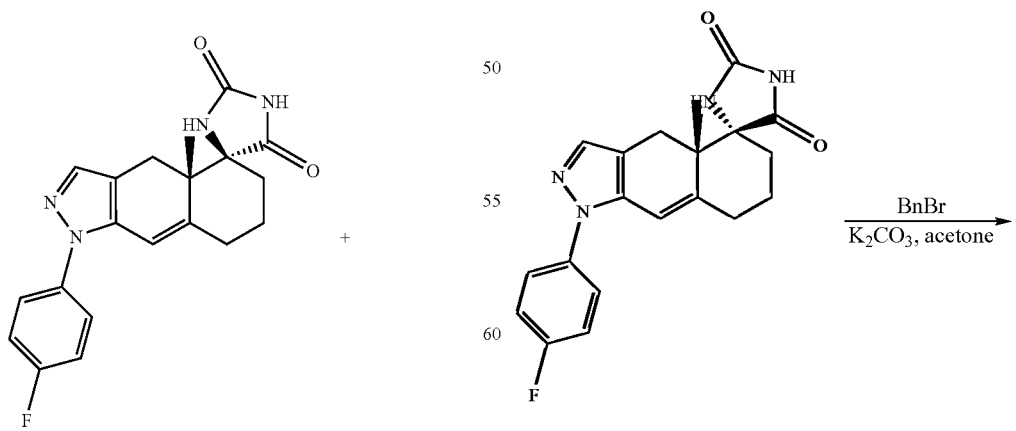

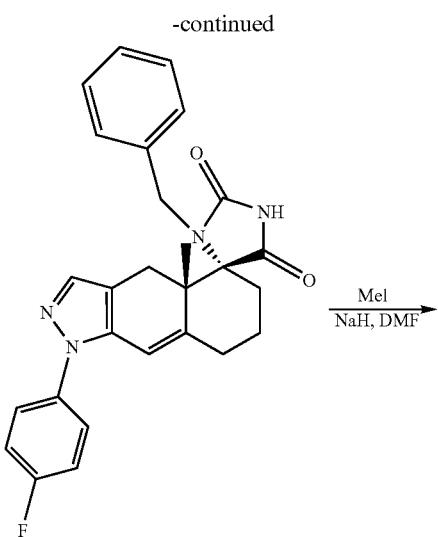
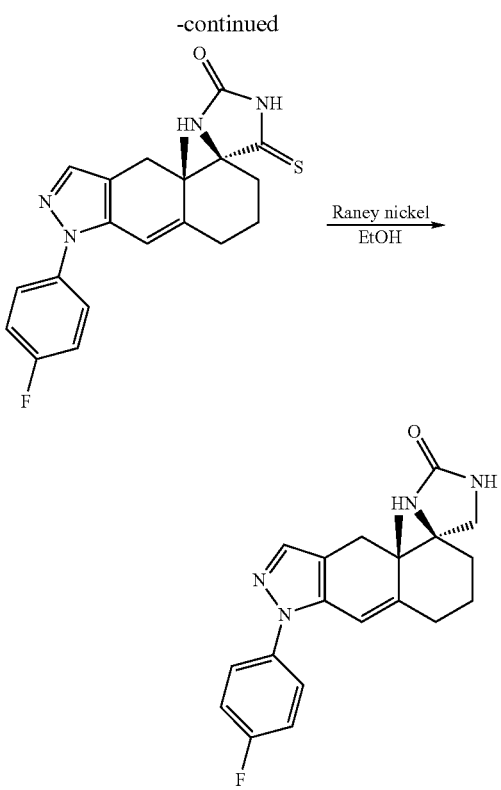
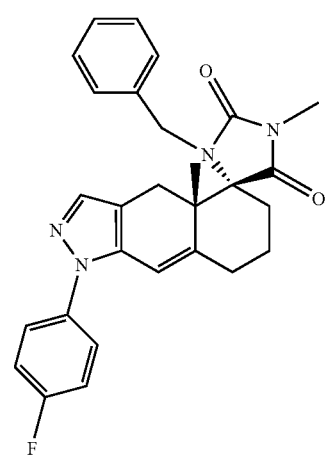
Scheme 21
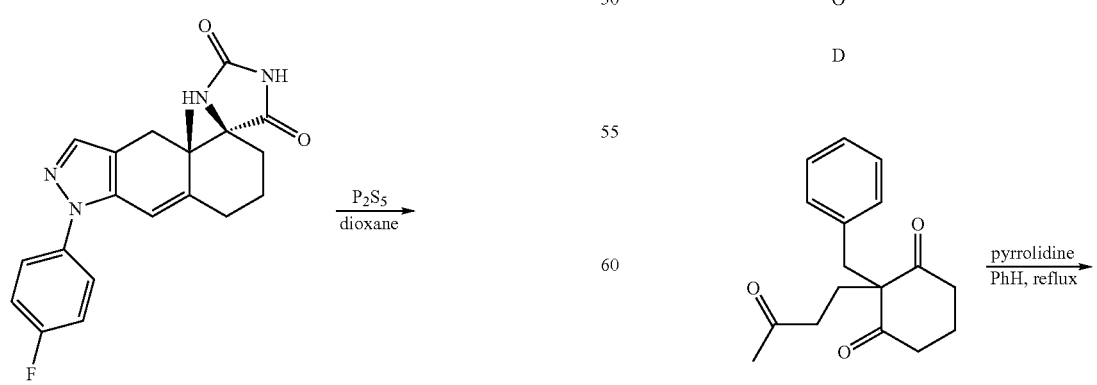

-continued
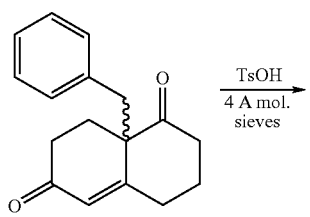
F
TsOH
4 A mol.
sieves
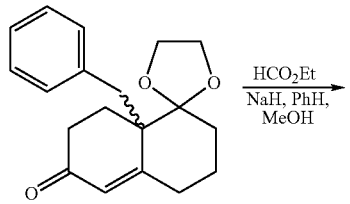
G
HCO₂Et
NaH, PhH,
MeOH
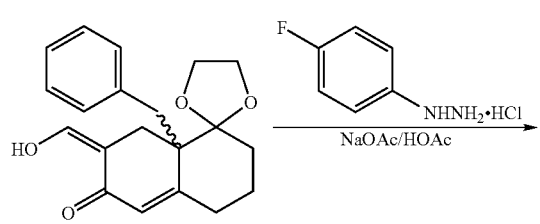
H
4-F-C₆H₄-NHNH₂·HCl
NaOAc/HOAc
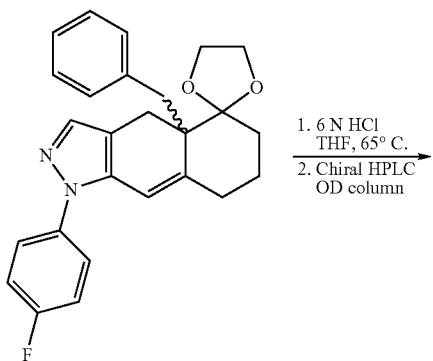
Example 137
1. 6 N HCl
   THF, 65° C.
2. Chiral HPLC
   OD column
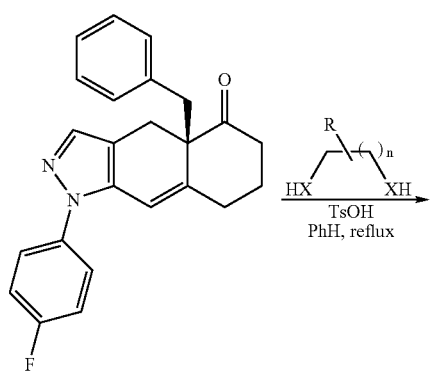
C
R
HX⁀(⁀)ₙ⁀XH
TsOH
PhH, reflux
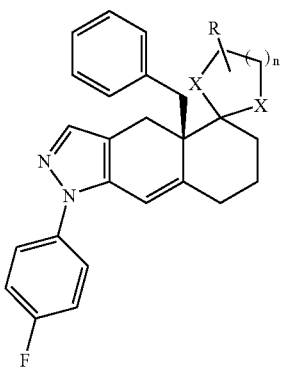
n = 1, 2
X = O, S
Scheme 23
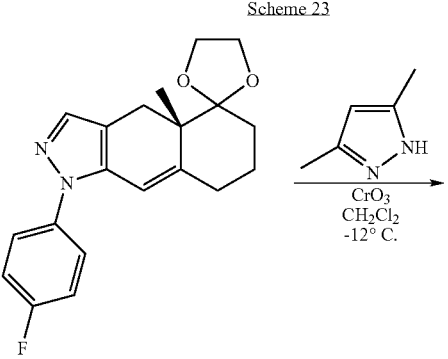
Example 138
3,5-dimethylpyrazole
CrO₃
CH₂Cl₂
−12° C.
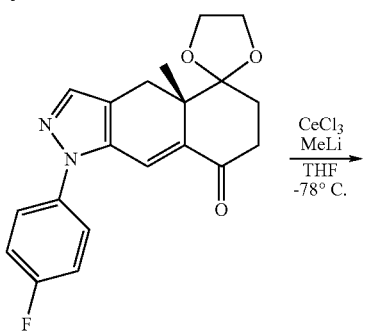
Example 140
CeCl₃
MeLi
THF
−78° C.
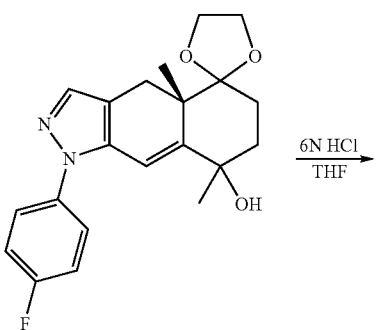
Example 141
6N HCl
THF

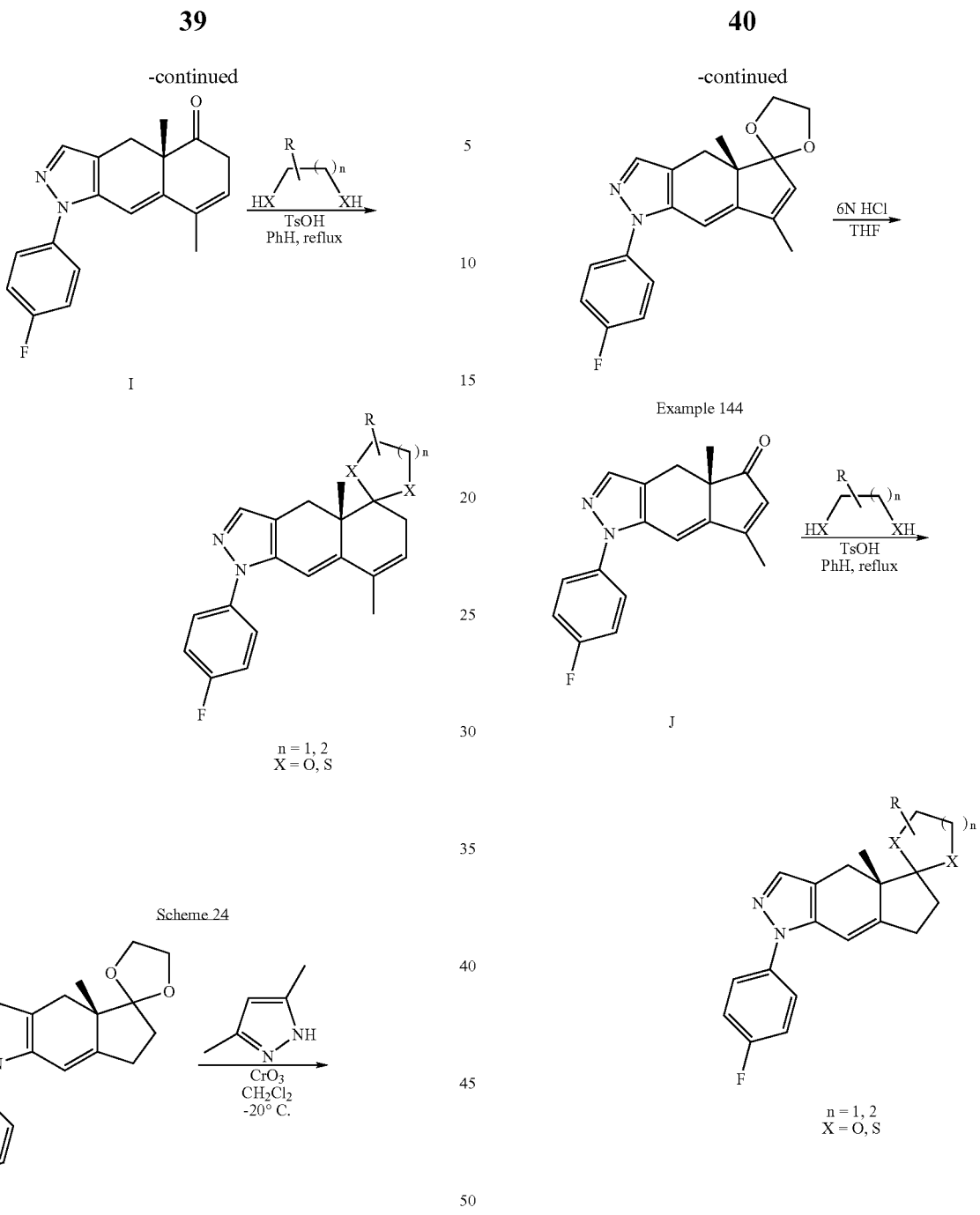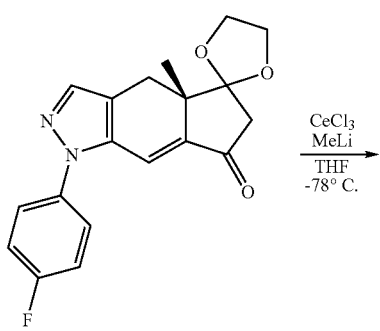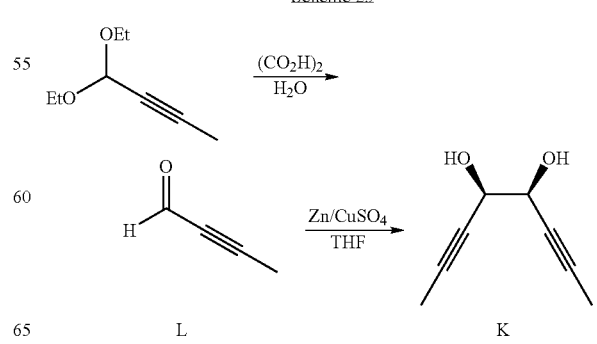

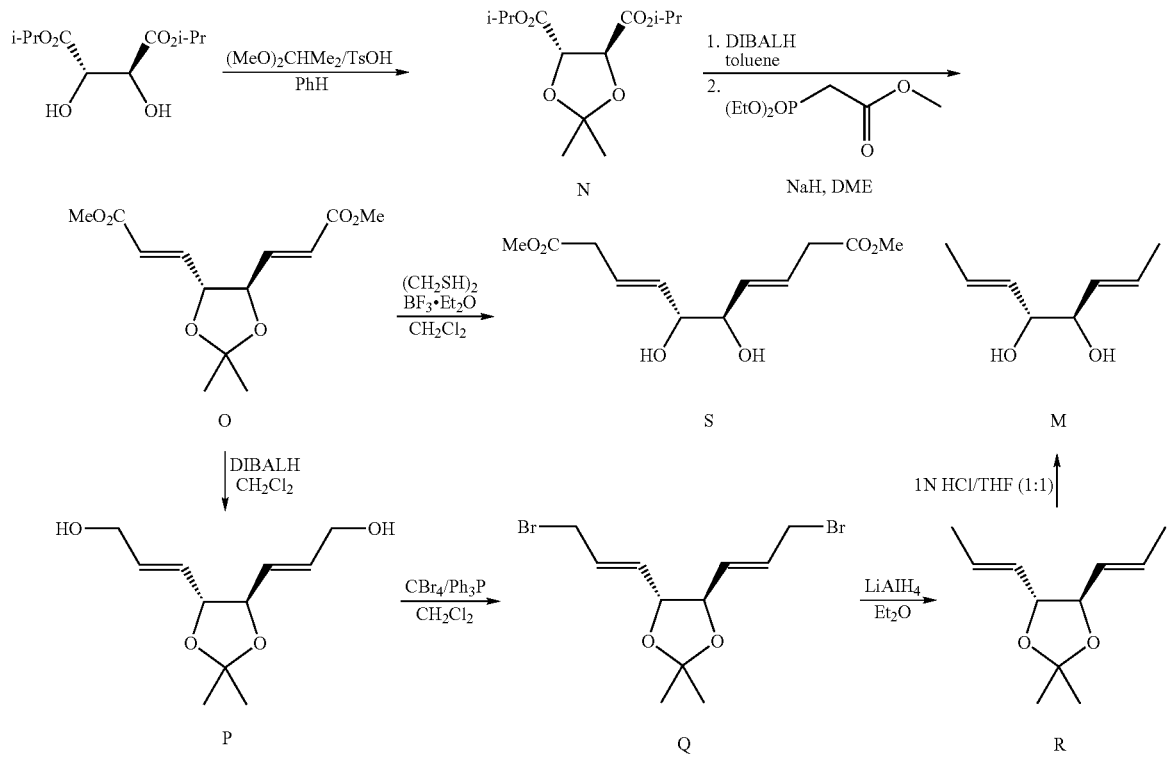
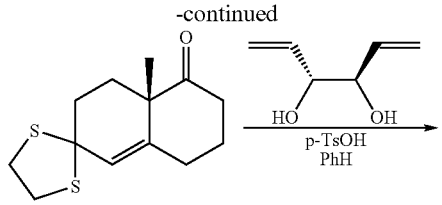
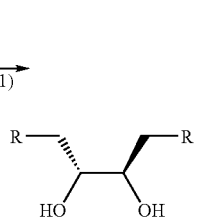
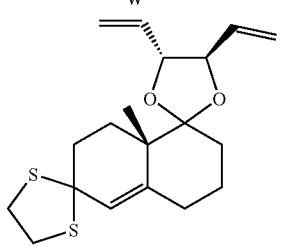
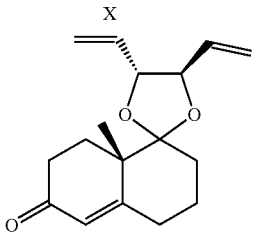
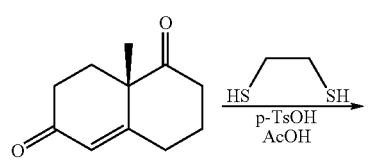

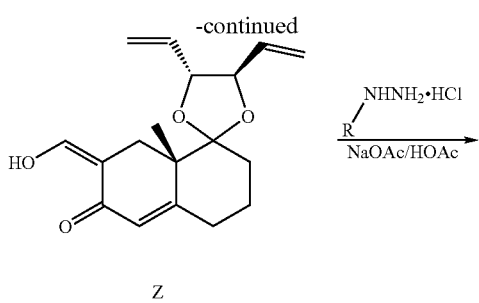

Z

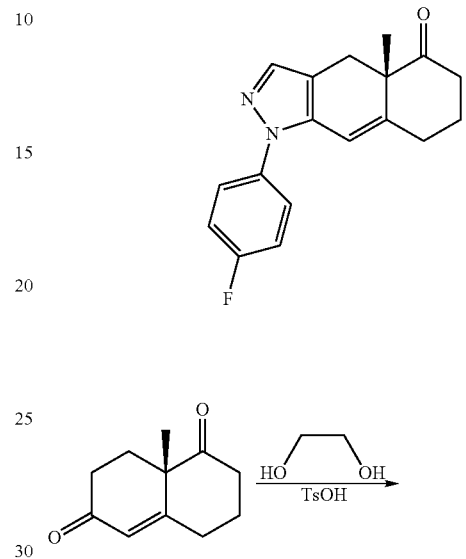

R

REPRESENTATIVE EXAMPLES

The invention will now be illustrated by the following non-limiting examples in which, unless stated otherwise:

(i) all operations were carried out at room or ambient temperature, that is, at a temperature in the range 18-25° C.;

(ii) evaporation of solvent was carried out using a rotary evaporator under reduced pressure (600-4000 pascals: 4.5-30 mm. Hg) with a bath temperature of up to 60° C.;

(iii) the course of reactions was followed by TLC and/or LCMS and reaction times are given for illustration only;

(iv) the structure and purity of all final products were assured by at least one of the following techniques: TLC, HPLC, MS or NMR spectrometry;

(v) yields, when given, are for illustration only;

(vi) when line-listed, NMR data is in the form of delta (δ) values for major diagnostic protons, given in parts per million (ppm) relative to tetramethylsilane (TMS) as internal standard, determined at 500 MHz or 600 MHz using the indicated solvent; conventional abbreviations used for signal shape are: s. singlet; d. doublet; t. triplet; m. multiplet; br. broad; etc.: in addition "Ar" signifies an aromatic signal;

(vii) chemical symbols have their usual meanings; the following abbreviations have also been used v (volume), w (weight), b.p. (boiling point), m.p. (melting point), L (litre(s)), ML (millilitres), g (gram(s)), mg (milligrams(s)), mol (moles), mmol (millimoles), eq or equiv (equivalent(s)), IC$_{50}$ (molar concentration which results in 50% of maximum possible inhibition), uM (micromolar), nM (nanomolar).

PREPARATIVE EXAMPLES

COMPOUND A

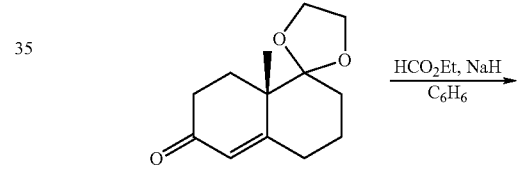

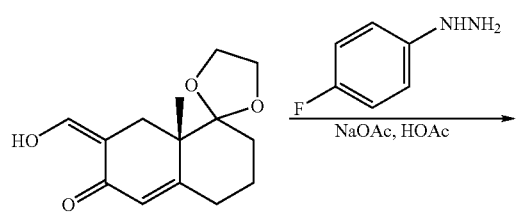

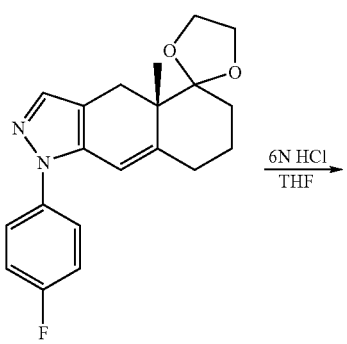

-continued

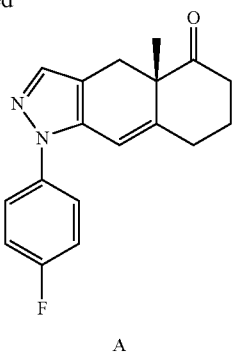

A

Step 1:

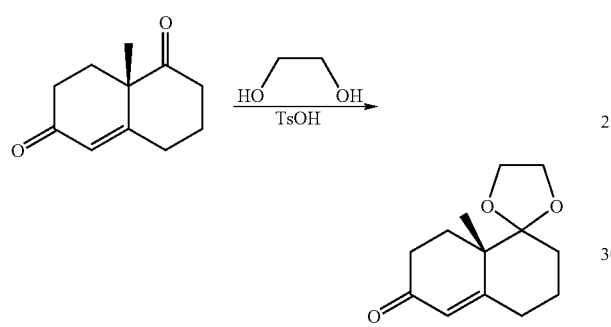

4 Å molecular sieves (~5 g) and p-toluenesulfonic acid (5.34 g, 28.05 mmol) were added to a solution of the Wieland-Miescher ketone (5 g, 28.05 mmol) in ethylene glycol (140 mL). After stirring at room temperature for 23 min., the reaction was poured slowly into a 2:1 mixture of ice water/sat. aqeuous $NaHCO_3$ (150 mL). The reaction was extracted with EtOAc (4×100 mL) and the combined organic layers were washed with brine (100 mL), dried ($MgSO_4$), filtered and concentrated ill vacuo. The residue was purified by flash chromatography (0 to 40% EtOAc/hexanes) on silica gel to afford the ketal (5.77 g, 93%) as a white solid. LCMS=223; $(M+1)^+$. $^1$H NMR ($CDCl_3$, 500 MHz): δ 5.83 (br d, J=1.8 Hz, 1H), 4.43-3.94 (m, 4H), 2.49-2.40 (m, 3H), 2.39-2.27 (m, 2H), 1.95-1.88 (m, 1H), 1.84-1.78 (m, 1H), 1.76-1.64 (m, 3H), 1.37 (s, 3H).

Step 2:

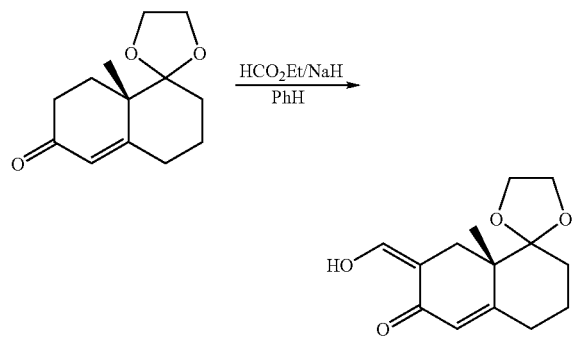

Ethyl formate (7.36 mL, 86.48 mmol) and sodium hydride (60% suspension in mineral oil; 3.46 g, 86.48 mmol) were added to a cooled solution (−40° C.) the ketal in anhydrous benzene (200 mL). MeOH (450 TL) was added dropwise over 15 min. and the reaction allowed to warm to room temperature. After stirring for 3 h, the reaction was cooled to 0° C. and water (50 mL) was added. The biphasic system was shaken and the organic layer was washed with water (3×50 mL). The combined aqueous layers were washed with diethyl ether (100 mL) and then acidified to pH 5.5-6 with sat. aqueous $KH_2PO_4$. The aqueous layer was extracted with EtOAc (5×200 mL). The combined extracts were dried ($Na_2SO_4$) and concentrated in vacuo to afford the hydroxyketone (5.04 g, 93%) as an orange oil. LCMS=251; $(M+1)^+$.

Step 3:

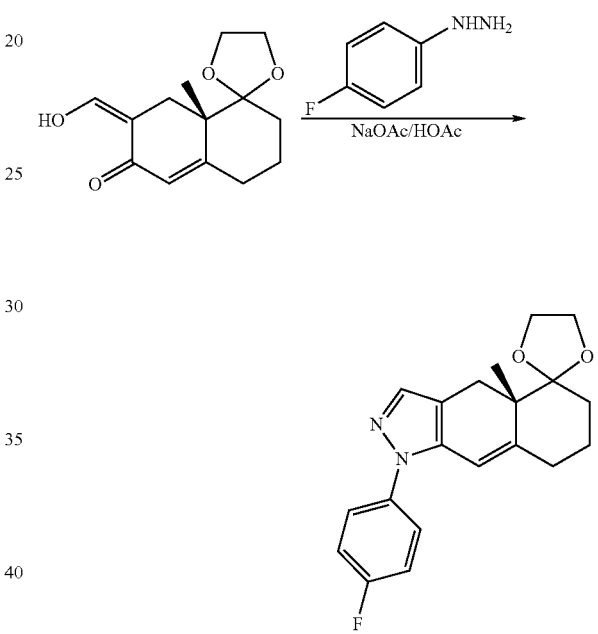

Example 138

The hydroxyketone (4.1 g, 16.4 mmol) was dissolved in glacial acetic acid (40 mL) and p-fluorophenylhyradzine hydrochloride (2.8 g, 17.22 mmol) and sodium acetate (1.41 g, 17.22 mmol) were added. After stirring at room temperature for 2 h, the reaction was poured slowly into 10% $NaHCO_3$ (1 L) and extracted with EtOAc (6×500 mL). The combined extracts were washed with brine (500 mL), dried ($MgSO_4$) and concentrated in vacuo. The crude material was purified by flash chromatography (10% EtOAc/hexanes) on silica gel to afford Example 138 (2.26 g, 41%) as an orange solid. LCMS=421; $(M+1)^+$. $^1$H NMR ($CDCl_3$, 500 MHz): δ 7.47-7.44 (m, 2H), 7.43 (s, 1H), 7.18-7.16 (d, J=8.5 Hz, 1H), 7.16-7.14 (d, J=8.7 Hz, 1H), 6.22 (br d, J=2.2 Hz, 1H), 4.11-4.01 (m, 4H), 3.20-3.16 (d, J=15.7 Hz, 1H), 2.54-2.51 (d, J=16 Hz, 1H), 2.51-2.40 (m, 1H), 2.34-2.28 (m, 1H), 1.88-1.64 (m, 4H), 1.23 (s, 3H).

Step 4:

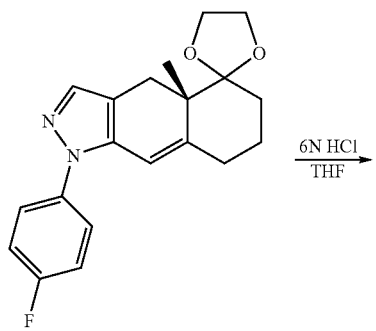

Example 138

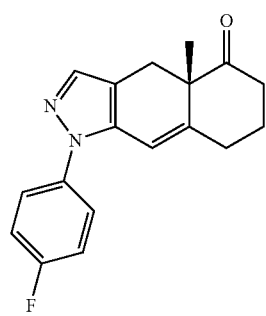

A

Example 138 (2.26 g; 6.65 mmol) was dissolved in THF (65 mL) and 6N HCl (4.43 mL, 26.6 mL) was added. The reaction was heated at 65° C. for 3.5 h and then poured slowly into 10% NaHCO₃ (150 mL). The mixture was extracted with EtOAc (4×250 mL) and the combined extracts washed with brine (2×200 mL), dried (MgSO₄) and concentrated in vacuo to afford COMPOUND A (1.97 g, 100%) as a brown oil. LCMS=297; (M+1)⁺. ¹H NMR (CDCl₃, 500 MHz): δ 7.50 (s, 1H), 7.49-7.45 (m, 2H), 7.20-7.16 (m, 2H), 6.31 (br d, J=2 Hz, 1H), 2.96-2.88 (m, 2H), 2.72-2.62 (m, 2H), 2.59-2.53 (m, 2H), 2.14-2.80 (m, 1H), 1.75-1,64 (qt, J=13.1 Hz, J=4.3 Hz, 1H), 1.27 (s, 3H).

COMPOUND B

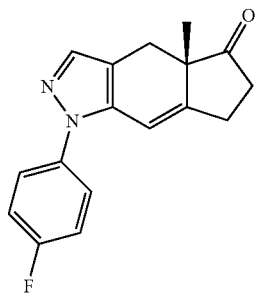

COMPOUND B was prepared from the known Hajos-Parrish ketone (*J. Org. Chem.* 1974, 39(12), 1612-1621.) following the same reaction sequence and procedure described above for the preparation of COMPOUND A.

EXAMPLES

The following examples illustrate the preparation of some of the compounds of the invention and are not to be construed as limiting the invention disclosed herein.

Example 1

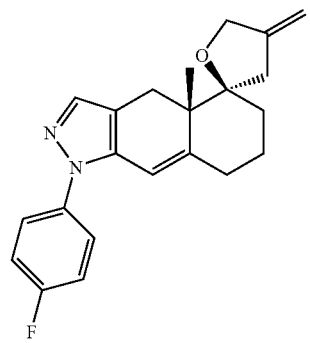

In 2 mL of anhydrous degassed tetrahydrofuran under an argon atmosphere were added tris(dibenzylideneacetone) dipalladium (0) (10 mg), triphenyl phosphine (30 mg) and trimethyl tin acetate (20 mg). To this was added COMPOUND A (110 mg, 0.374 mmol) in 1.0 mL degassed THF followed by trimethylsilyl acetoxy propene. The resulting reaction mixture was heated to 100° C. for 15 h in a sealed tube before being filtered through celite, washed with ethyl acetate (50 mL) and evaporated under reduced pressure. The crude reaction mixture was purified by column chromatography (SiO₂, acetone/hexanes) to give recovered starting material (58 mg) and desired product as a white foam. The product was characterized by ¹H NMR, HPLC and mass spectroscopy (m/z: 351 (M⁺+1)).

Example 2

Example 1 (10 mg, 0.029 mmol) was diluted into ethyl acetate (1 mL), treated with a catalytic amount of palladium on carbon, and exposed to an atmosphere of hydrogen gas via a double-walled balloon; vacuum-purged thrice. The reaction mixture was stirred at room temperature for 1 h, filtered over celite and concentrated in vacuo. The residue was purified by preparative thin layer chromatography (SiO₂, 250 micron, Example 3

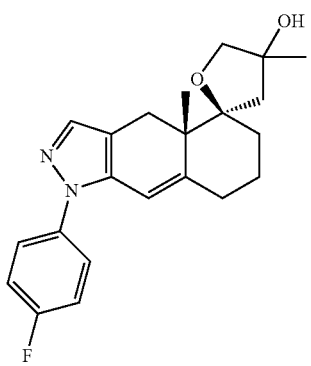

Example 1 (10 mg, 0.029 mmol) was diluted into (1:1) TBF-H$_2$0 (1 mL), treated with mercury(II) acetate (14 mg, 0.043 mmol), and the reaction mixture stirred at 23° C. for 14 h. The reaction mixture was then treated slowly with 0.50 mL of a solution of sodium borohydride (56 mg, 1.5 mmol) in aqueous 3M NaOH at room temperature. The reaction mixture was maintained for 2 h at 23° C., partitioned between water and diethyl ether, the organic phase dried over anhydrous sodium sulfate and concentrated in vacuo. The residue was purified by preparative thin layer chromatography (SiO$_2$, 250 micron, 20×20 cm, 50% EtOAc-hexanes) to give the separated isomeric products, each of which were characterized by $^1$H NMR, HPLC and mass spectroscopy (m/z: 369 (M$^+$+1)).

Examples 4 and 5

EXAMPLE 4

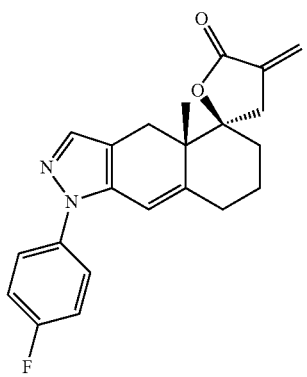

EXAMPLE 5

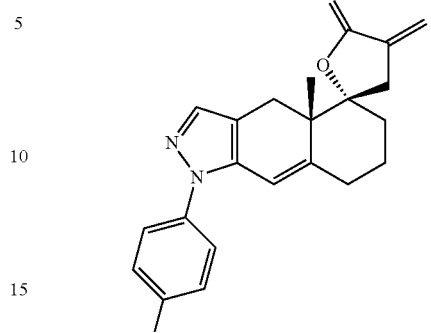

COMPOUND A (50 mg, 0.168 mmol) was dissolved in 1.0 mL of THF under argon atmosphere. Activated zinc (0.336 mmol, 22 mg), ethyl ac-bromomethyl acrylate (0.336 mmol, 0.040 mL), and catalytic hydroquinone (0.005 mL) were added and the reaction mixture was heated to 110° C. for 15 hours before it was cooled to room temperature. The reaction was quenched with 25 mL of 1 N aqueous HCl, extracted with methylene chloride (3×25 mL) and the resulting organic layers were dried over sodium sulfate and evaporated under reduced pressure. The crude reaction mixture was purified by column chromatography (SiO$_2$, ethyl ether/hexanes) to give the desired isomeric products as white foams. The product isomers were each characterized by $^1$H NMR, HPLC and mass spectroscopy (m/z: 365 (M$^+$+1)).

Example 6

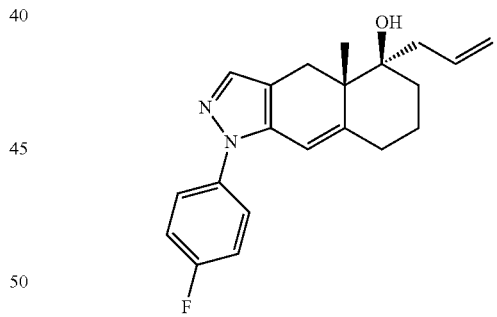

COMPOUND A (300 mg, 1.0 mmol) was dissolved in 4 mL of anhydrous THF under argon atmosphere and cooled to −50° C. Then 3.0 equiv of allyl magnesium bromide (1M in THF, 3.00 mmol, 3.0 mL) was added dropwise. The resulting reaction mixture was then allowed to slowly warm to 23° C. over 6 h. The reaction was quenched with 50 mL of saturated aqueous NH$_4$Cl, extracted with methylene chloride (3×35 mL) and the organic layers were dried over sodium sulfate and evaporated under reduced pressure. The crude reaction mixture was purified by flash column chromatography (SiO$_2$, EtOAc/hexanes) to give the desired product as an off-white foam. The product was characterized by ¹H NMR, HPLC and mass spectroscopy (m/z: 339 (M⁺+1)).

Example 7

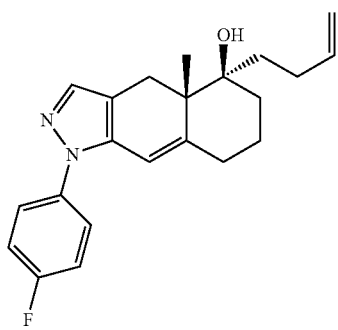

Example 7 was prepared from COMPOUND A according to the above procedure described in Example 6. The product was characterized by ¹H NMR, HPLC and mass spectroscopy (m/z: 353 (M⁺+1)).

Example 8

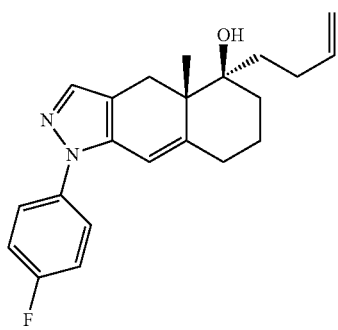

Example 8 was prepared from COMPOUND B according to the above procedure described in Example 6. The product was characterized by ¹H NMR, HPLC and mass spectroscopy (m/z: 339 (M⁺+1)).

Example 9

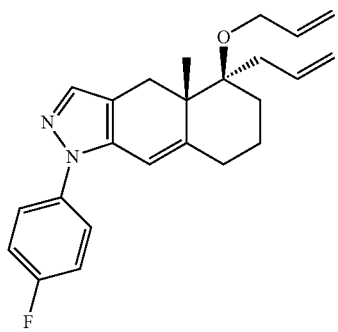

Example 6 (50 mg, 0.148 mmol) was dissolved in 1.0 mL of 5:1 THF/HMPA under argon atmosphere and sodium hydride (60% in mineral oil, 0.290 mmol, 12 mg) was added and the reaction mixture was allowed to stir for 10 min at room temperature. Allyl bromide (0.592 mmol, 0.051 mL) was then added and the reaction was heated to 80° C. for 2 hours before cooling to room temperature. The reaction was then quenched by the addition of 25 mL of saturated aqueous NH₄Cl, extracted with methylene chloride (3×25 mL) and the resulting organic layers were dried over sodium sulfate and evaporated under reduced pressure. The crude reaction mixture was purified by column chromatography (SiO₂, acetone/hexanes) to give the desired product as a pale yellow foam. The product was characterized by ¹H NMR, HPLC and mass spectroscopy (m/z: 379 (M⁺+1)).

Example 10

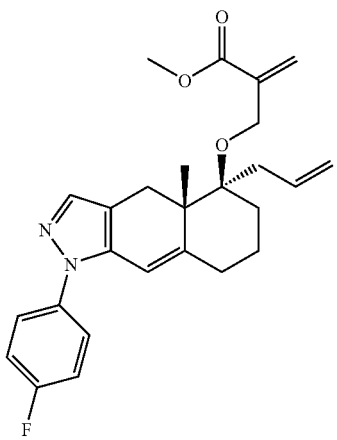

Example 10 was prepared from Example 6 according to the above procedure described in Example 9. The product was characterized by ¹H NMR, HPLC and mass spectroscopy (m/z: 437 (M⁺+1)).

Example 11

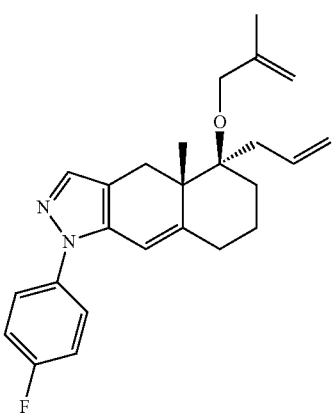

Example 11 was prepared from Example 6 according to the above procedure described in Example 9. The product was characterized by $^1$H NMR, HPLC and mass spectroscopy (m/z: 393 (M$^+$+1)).

Example 12

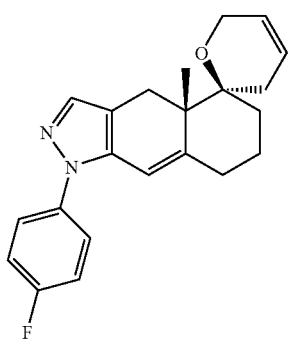

Example 9 (8 mg, 0.021 mmol) was dissolved in 1.0 mL of degassed benzene under argon atmosphere and to this was added catalytic bis(tricyclohexylphosphine)-benzylidine ruthenium (IV) dichloride (2 mg) and the resulting reaction mixture was heated to 100° C. for 4 hours before it was cooled to room temperature, filtered through celite, washed with ethyl acetate (25 mL) and evaporated under reduced pressure. The crude reaction mixture was purified by column chromatography (SiO$_2$, acetone/hexanes) to give the desired product as a clear film. The product was characterized by $^1$H NMR, HPLC and mass spectroscopy (m/z: 351 (M$^+$+1)).

Example 13

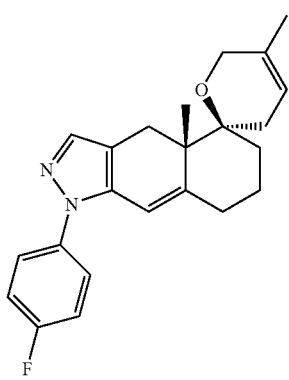

Example 13 was prepared from Example 11 according to the above procedure described in Example 12. The product was characterized by $^1$H NMR, HPLC and mass spectroscopy (m/z: 365 (M$^+$+1)).

Example 14

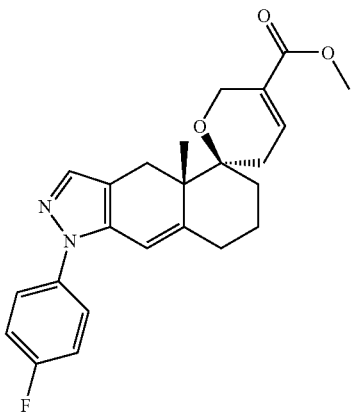

Example 14 was prepared from Example 10 according to the above procedure described in Example 12. The product was characterized by $^1$H NMR, HPLC and mass spectroscopy (m/z: 409 (M$^+$+1)).

Example 15

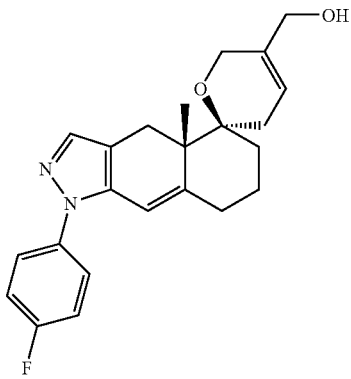

Example 15 was prepared via a lithium aluminum hydride reduction of Example 14 according to the procedure described below in Example 78. The product was characterized by $^1$H NMR, HPLC and mass spectroscopy (m/z: 381 (M$^+$+1)).

Example 16

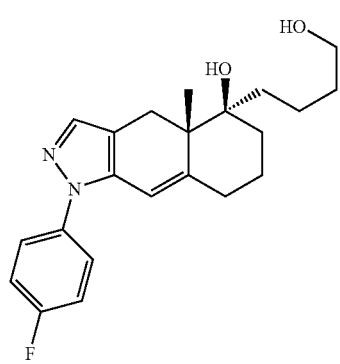

Example 7 (14 mg, 0.039 mmol) was dissolved in 1.0 mL TBF under argon atmosphere and cooled to 0° C. and 9-borabicyclo[3.3.1]nonane (0.5M in THF, 0.156 mmol, 0.312 mL) was added. The reaction mixture was allowed to warm to room temperature and stir for 15 h before being quenched by the addition of 1 mL of ethanol, 0.052 mL of 6N aqueous NaOH, and 0.1 mL of 30% aqueous hydrogen peroxide. The reaction mixture was then diluted with 5.0 mL of water, extracted with methylene chloride (3×4 mL) and the organic layers were dried over sodium sulfate and evaporated under reduced pressure. The crude reaction product was purified by preparative thin layer chromatography (SiO$_2$, EtOAc/hexanes) and characterized by $^1$H NMR, HPLC and mass spectroscopy (m/z: 371 (M$^+$+1)).

Example 17

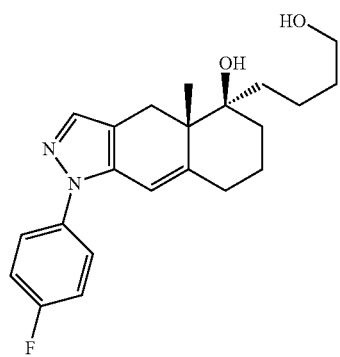

Example 17 was prepared from Example 8 according to the above procedure described in Example 16. The product was characterized by $^1$H NMR, HPLC and mass spectroscopy (m/z: 357 (M$^+$+1)).

Example 18

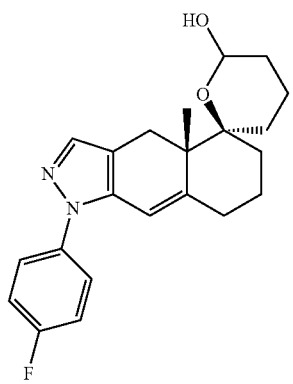

Example 16 (15 mg, 0.041. mmol) was dissolved in 1.0 mL methylene chloride under argon atmosphere and cooled to 0° C. before 20 equiv of pyridine (0.82 mmol, 0.066 mL) and 3.0 equiv of Dess-Martin periodinane (0.122 mmol, 52 mg) were added, and the reaction mixture was then warmed to room temperature over 15 h. The reaction mixture was quenched with 20 mL of saturated aqueous NH$_4$Cl, extracted with methylene chloride (3×15 mL), and the organic layers were dried over sodium sulfate and evaporated under reduced pressure. The crude reaction product was purified by column chromatography (SiO$_2$, EtOAc/hexanes) and characterized by $^1$H NMR, HPLC and mass spectroscopy (m/z: 367 (M$^+$+1)).

Example 19

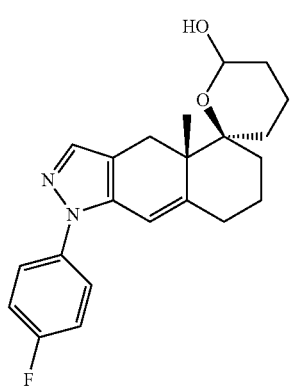

Example 19 was prepared from Example 17 according to the above procedure described in Example 18. The product was characterized by ¹H NMR, HPLC and mass spectroscopy (m/z: 355 (M⁺+1)).

Example 20

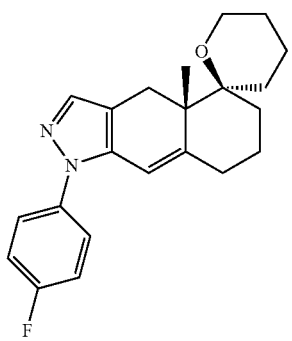

Example 18 (6 mg, 0.016 mmol) was dissolved in 0.5 mi methylene chloride under argon atmosphere and cooled to −80° C. before triethyl silane (0.163 mmol, 0.027 mL) and boron trifluoride etherate (0.049 mmol, 0.007 mg) were added and the reaction mixture was then allowed to slowly warm to 0° C. The reaction was quenched with 20 ml of saturated aqueous sodium bicarbonate, extracted with methylene chloride (3×15 mL) and the organic layers were dried over sodium sulfate and evaporated under reduced pressure. The residue was purified by column chromatography (SiO₂, acetone/hexanes) to give the desired product as a clear film. The product was characterized by ¹H NMR, HPLC and mass spectroscopy (m/z: 353 (M⁺+1)).

Example 21

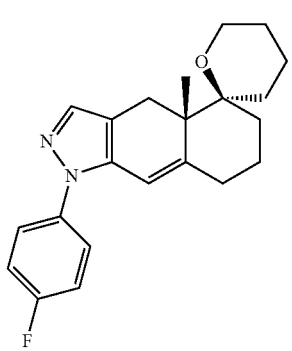

Example 21 was prepared from Example 19 according to the above procedure described in Example 20. The product was characterized by ¹H NMR, HPLC and mass spectroscopy (m/z: 339 (M⁺+1)).

Example 22

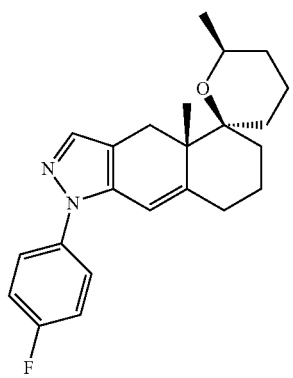

Example 18 was dissolved in 0.5 mL of methylene chloride under argon atmosphere and cooled to −80° C. To this was added boron trifluoride etherate (0.105 mmol, 0.013 mL) and dimethyl zinc [1M heptane] (0.21 mmol, 0.21 mL) and the reaction mixture was allowed to warm to room temperature and stir for 15 h. The reaction was quenched with 10 mL of saturated aqueous ammonium chloride, extracted with methylene chloride (3×10 mL), and the organic layers were dried over sodium sulfate and evaporated under reduced pressure. The residue was purified by column chromatography (SiO₂, acetone/hexanes) to give the desired product as a clear film. The product was characterized by ¹H NMR, HPLC and mass spectroscopy (m/z: 367 (M⁺+1)).

Example 23

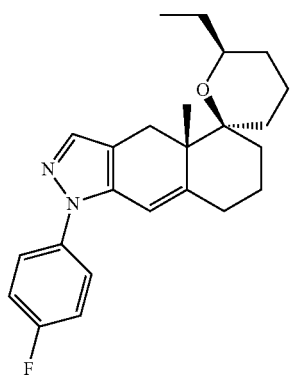

Example 23 was prepared from Example 18 according to the above procedure described in Example 22. The product was characterized by ¹H NMR, HPLC and mass spectroscopy (m/z: 381 (M⁺+1)).

Example 24

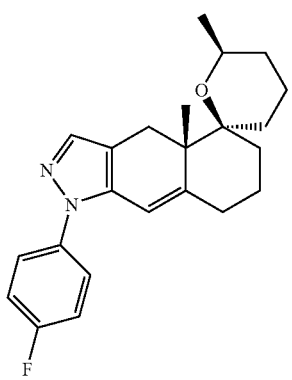

Example 24 was prepared from Example 19 according to the above procedure described in Example 22. The product was characterized by ¹H NMR, HPLC and mass spectroscopy (m/z: 353 (M⁺+1)).

Example 25

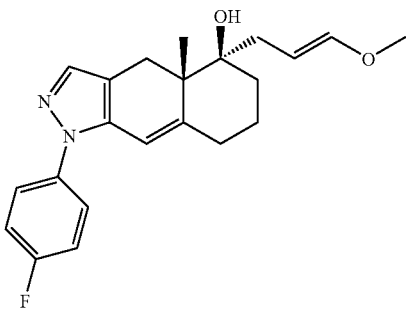

COMPOUND A (300 mg, 1.01 mmol) was diluted into THF (10 mL), treated with allyl methyl ether (0.318 mL, 3.4 mmol), and t-butyl lithium (1.8 mL, 3 mmol) at −78° C. and maintained for 1 h. The reaction mixture was then partitioned between NH₄Cl$_{(aq)}$ and CH₂Cl₂. The organic phase was dried over anhydrous sodium sulfate and concentrated in vacuo. The crude product was either used directly in subsequent reactions or purified by flash chromatography (Biotage 40S, SiO₂, 30% EtOAc-hexane) to provide the product which was characterized by ¹H NMR, HPLC and mass spectrometry (m/z: 369 (M⁺+1)).

Example 26

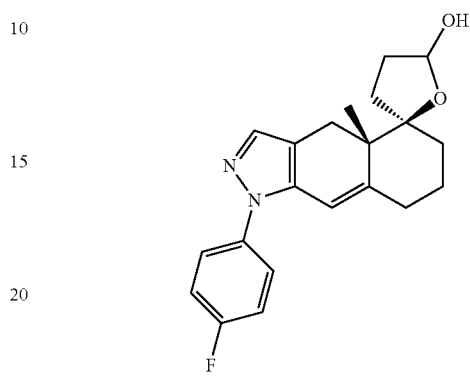

Example 25 (372 mg, 1.01 mmol) was diluted into a solution of tetrahydrofuran (20 mL) and 3N perchloric acid (3 mL). The mixture was maintained at room temperature for 15 h. The reaction mixture was concentrated in vacuo and purified by preparative thin layer chromatography (4×1500 micron SiO₂, 20×20 cm, 30% acetone-hexane) to provide the product which was characterized by ¹H NMR, HPLC and mass spectrometry (m/z: 355 (M⁺+1)).

Example 27

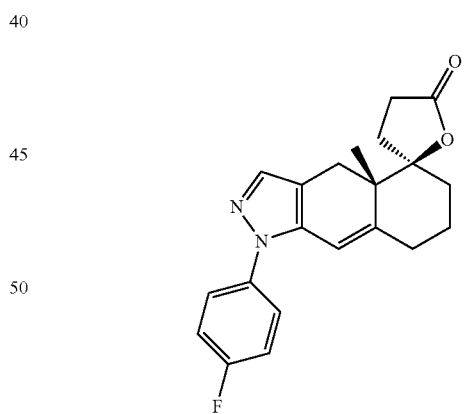

Example 26 (45 mg, 0.13 mmol) was diluted into CH₂Cl₂ (6.5 mL) and treated with 4-methylmorpholine N-oxide (45.6 mg, 0.39 mmol) and activated 4 Å sieves. The reaction mixture was then cooled to 0° C. and treated with tetrapropylammonium perruthenate (4.6 mg, 0.013 mmol), maintained at 23° C. for 1 h, filtered over celite and partitioned between 10% NaHSO₃$_{(aq)}$ and CH₂Cl₂. The organic phase was dried over anhydrous sodium sulfate, concentrated in vacuo, and purified by preparative thin layer chromatography (1500 micron SiO₂, 20×20 cm, 50% EtOAc-hexane) to provide the product which was characterized by $^1$H NMR, HPLC and mass spectrometry (m/z: 353 (M$^+$+1)).

Example 28

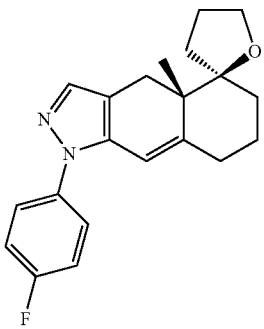

Example 26 (47 mg, 0.12 mmol) was diluted into CH$_2$Cl$_2$ (6.5 mL), cooled to −78° C., and treated with triethylsilane (0.198 mL, 1.2 mmol) and boron trifluoride diethyl etherate (0.031 mL, 0.24 mmol). The reaction mixture was maintained at −78° C. for 0.5 h and then warmed to 23° C. for 1 h. The mixture was partitioned between NaHCO$_{3(a, g)}$ and CH$_2$Cl$_2$, the organic phase was dried over anhydrous sodium sulfate, concentrated in vacuo, and purified by preparative thin layer chromatography (1500 micron SiO$_2$, 20×20 cm, 50% EtOAc-hexane) to provide the product which was characterized by $^1$H NMR, HPLC and mass spectrometry (m/z: 339 (M$^+$+1)).

Example 29

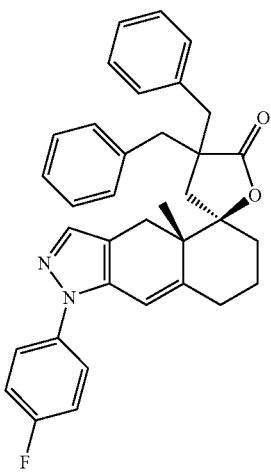

Example 27 (47 mg, 0.12 mmol) was diluted into tetrahydrofuran (0.355 mL), cooled to −78° C., treated with lithium bis(trimethylsilyl)amide (0.146 mL, 0.146 mmol, 1M THF), and maintained at −78° C. for 0.5 h. The reaction mixture was treated with benzyl bromide (0.042 mL, 0.35 mmol) and maintained at 0° C. for 3 h. The mixture was partitioned between NaHCO$_{3(aq)}$ and EtOAc, the organic phase was dried over anhydrous sodium sulfate, concentrated in vacuo, and purified by preparative thin layer chromatography (500 micron SiO$_2$, 20×20 cm, 30% acetone-hexane) to provide the product which was characterized by $^1$H NMR, HPLC and mass spectrometry (m/z: 533 (M$^+$+1)).

Example 30

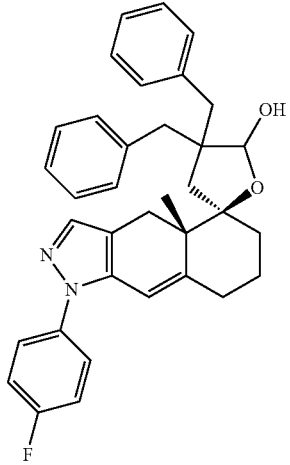

Example 29 (60 mg, 0.11 mmol) was diluted into toluene (0.550 mL), then cooled to −78° C., treated with diisobutylaluminum hydride (0.230 mL, 0.23 mmol, 1M toluene), and maintained at −78° C. for 1 h. The reaction mixture was quenched with Rochelle's salt (2.75 mL) and filtered over celite. The mixture was partitioned between NaHCO$_{3(aq)}$ and CH$_2$Cl$_2$, the organic phase was dried over anhydrous sodium sulfate, concentrated in vacuo, and purified by preparative thin layer chromatography (500 micron SiO$_2$, 20×20 cm, 30% acetone-hexane) to provide the product which was characterized by $^1$H NMR, HPLC and mass spectrometry (m/z: 535 (M$^+$+1)).

Example 31

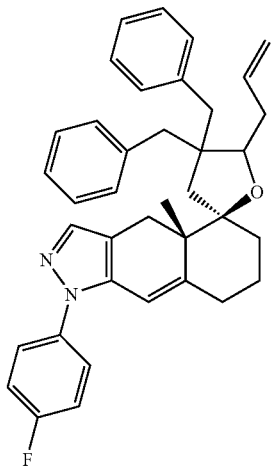

Example 30 (20 mg, 0.037 mmol) was diluted into CH$_2$Cl$_2$ (0.748 mL), cooled to −78° C. and treated with allyltrimethylsilane (0.059 mL, 0.374 mmol) and boron trifluoride diethyl etherate (0.009 mL, 0.075 mmol). The reaction mixture was maintained at −78° C. for 0.5 h and warmed to 23° C. for 3 h.

The mixture was partitioned between NaHCO$_{3(aq)}$ and CH$_2$Cl$_2$, the organic phase was dried over anhydrous sodium sulfate, concentrated in vacuo, and purified by preparative thin layer chromatography (500 micron SiO$_2$, 20×20 cm, 30% acetone-hexane) to provide the product which was characterized by $^1$H NMR, HPLC and mass spectrometry (m/z: 559 (M$^+$+1)).

Example 32

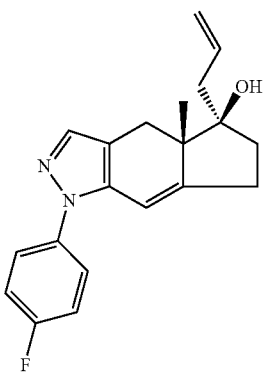

COMPOUND B (330 mg, 1.06 mmol) in THF (10 mL) was added dropwise to a solution of allyl magnesium bromide (6.21 mL, 6.21 mmol) in THF (10 mL). The reaction mixture was maintained at 23° C. for 1 h, partitioned between NH$_4$Cl$_{(aq)}$ and CHCl$_3$, the organic phase dried over anhydrous sodium sulfate, and concentrated in vacuo. The crude product was used in the subsequent reaction to generate Example 33. The product was characterized by $^1$H NMR, HPLC and mass spectrometry (m/z: 325 (M$^+$+1)).

Example 33

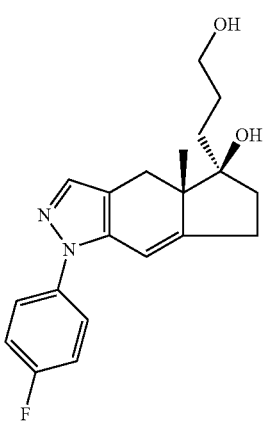

Example 32 (131 mg, 0.404 mmol) was diluted into tetrahydrofuran (4 mL) and treated with 9-BBN (4.04 mL, 2.02 mmol). The reaction mixture was maintained at 23° C. for 1 h, quenched with ethanol (4.04 mL), 30% sodium hydroxide (1.21 mL), and 60% hydrogen peroxide (2.42 mL) respectively. The quenched reaction mixture was maintained at 50° C. for 1 h. The mixture was then partitioned between H$_2$O and CH$_2$Cl$_2$. The organic phase was dried over anhydrous sodium sulfate, concentrated in vacuo, and purified by preparative centrifugal thin layer chromatography (Chromatotron, 4 mm SiO$_2$, 1:9:90 NH$_4$OH-MeOH—CHCl$_3$) to provide the product which was characterized by $^1$H NMR, HPLC and mass spectrometry (m/z: 343 (M$^+$+1)).

Example 34

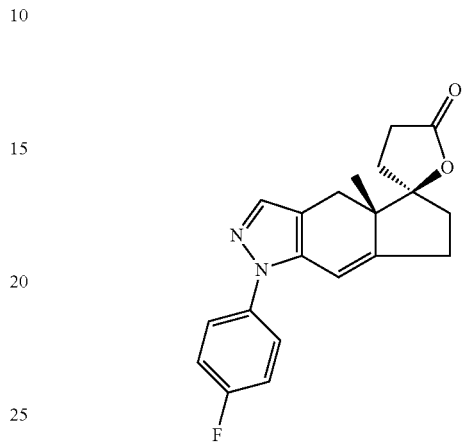

Example 33 (113 mg, 0.343 mmol) was diluted into CH$_2$Cl$_2$ (8 mL) and treated with 4-methylmorpholine N-oxide (91.44 mg, 0.78 mmol) and activated 4A sieves. The reaction mixture was then cooled to 0° C. and treated with tetrapropylammonium perruthenate (10.98 mg, 0.031 mmol). The reaction mixture was maintained at 23° C. for 1 h, filtered over celite, and partitioned between 10% NaHSO$_{3(aq)}$ and CH$_2$Cl$_2$. The organic phase was dried over anhydrous sodium sulfate, concentrated in vacuo, and purified by preparative reversed phase HPLC (C18 SiO$_2$, 0-100% acetonitrile gradient in water with 0.1% TFA eluent) to provide the product which was characterized by $^1$H NMR, HPLC and mass spectrometry (m/z: 339 (M$^+$+1)).

Example 35

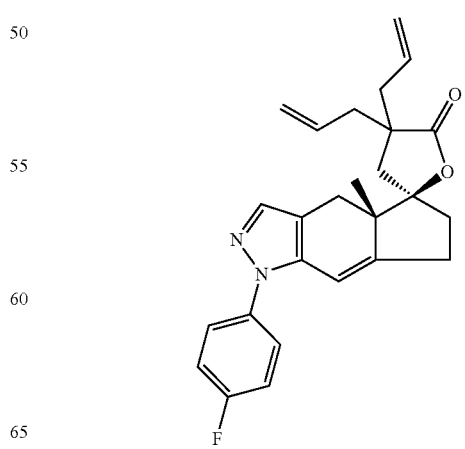

Example 35 was Prepared from Example 34 According to the Above Procedure Describes in Example 29. The Product was Characterized by $^1$H NMR, HPLC and Mass Spectroscopy (M/Z: 419 (M$^+$+1)).

Example 36

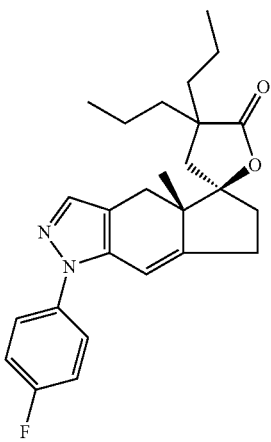

Example 35 (33 mg, 0.079 mmol) was diluted into EtOAc (3 mL) and treated with palladium on carbon under one atmosphere of H$_{2(g)}$ (double-walled balloon). The reaction mixture was maintained at 23° C. for 0.5 h, filtered over celite, concentrated in vacuo, and purified by preparative centrifugal thin layer chromatography (Chromatotron, 2 mm SiO$_2$, 10% to 50% ethyl acetate-hexane gradient elution) to provide the product which was characterized by $^1$H NMR, HPLC and mass spectrometry (m/z: 423 (M$^+$+1)).

Example 37

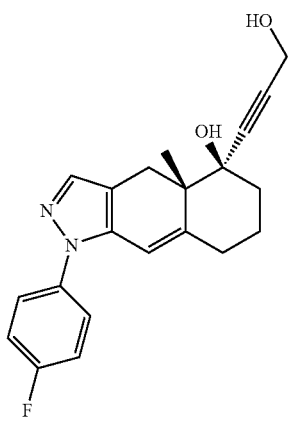

Magnesium turnings (10 mg, 0.42 mmol) were crushed and dissolved in THF (1 mL). Bromoethane (0.031 mL, 0.42 mmol) was added dropwise to the solution and allowed to stir at 23° C. for 0.5 h. The mixture was cooled to 0° C., treated with propargyloxytrimethylsilane (0.064 mL, 0.42 mmol), and warmed to 23° C. for 0.5 h. COMPOUND A (100 mg, 0.34 mmol) in THF (0.5 mL) was diluted into the above described solution at 0° C. and maintained at 23° C. for 1.5 h.

The reaction mixture was partitioned between NH$_4$Cl$_{(aq)}$ and EtOAc. The organic phase was dried over anhydrous sodium sulfate, concentrated in vacuo, and the crude diol was used directly in the subsequent reaction to generate Example 38. The product was characterized by $^1$H NMR, HPLC and mass spectrometry (m/z: 353 (M$^+$+1)).

Example 38

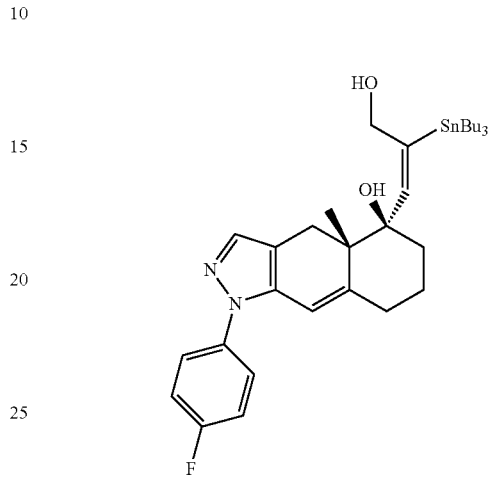

Example 37 (20 mg, 0.056 mmol) was diluted into dioxane (0.2 mL), and the mixture was treated with bis(triphenylphosphine)palladium dichloride (40 mg, 0.056 mmol) and tributyltin hydride (0.450 mL, 2.24 mmol). The mixture was maintained at 0° C. for 3 h, filtered over celite, concentrated in vacuo, and purified by preparative centrifugal thin layer chromatography (Chromatotron, 4 mm SiO$_2$, 1% triethylamine-ethyl acetate) to provide the product which was characterized by $^1$H NMR, HPLC and mass spectrometry (m/z: 645 (M$^+$+1)).

Example 39

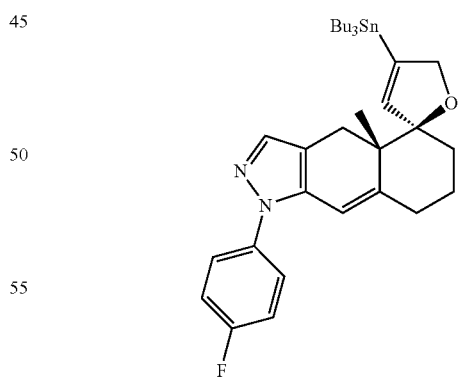

Example 38 (11 mg, 0.017 mmol) was diluted into tetrahydrofuran (0.010 mL), treated with triphenylphosphine (9.12 mg, 0.030 mmol), cooled to 0° C., and then treated with diethyl azodicarboxylate (0.005 mL, 0.030 mmol). The mixture was maintained at 0° C. for 1 h, concentrated in vacuo, and purified by preparative centrifugal thin layer chromatography (Chromatotron, 4 mm SiO$_2$, 1% triethylamine-hexane)

to provide the product which was characterized by $^1$H NMR, HPLC and mass spectrometry (m/z: 627 (M$^+$+1)).

Examples 40 and 41

EXAMPLE 40

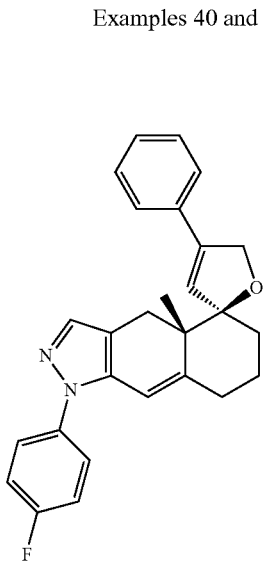

EXAMPLE 41

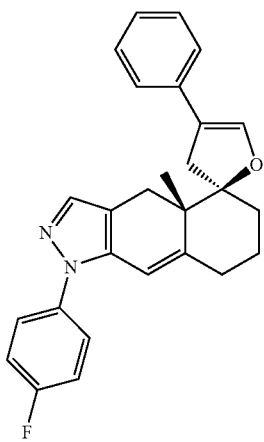

Examples 40 and 41 were prepared by diluting Example 39 (13 mg, 0.020 mmol) in toluene (1 mL) and treating the solution with lithium chloride (2.5 mg, 0.059 mmol), bromobenzene (0.003 mL, 0.029 mmol), and tetrakis-(triphenylphosphine)-palladium (1 mg, 0.0004 mmol). The reaction mixture was heated at 100° C. for 15 h, cooled to room temperature, filtered over celite, concentrated in vacuo, and purified by preparative thin layer chromatography (250 micron SiO$_2$, 20×20 cm, 20% acetone-hexane) to provide the resolution of both products which were each characterized by $^1$H NMR, HPLC and mass spectrometry (m/z: 413 (M$^+$+1)).

Examples 42-47

The following compounds were prepared under conditions similar to those described in the examples above and illustrated in Scheme 10. Other bromides known to those skilled in the art were used in place of bromobenzene to generate the analogs shown in the table below. Hydrogenation of Example 46 as described in Example 36 was used to generate Example 47. The following examples were characterized by $^1$H NMR, HPLC and mass spectrometry.

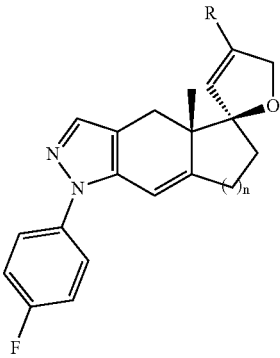

| EXAMPLE | n | R-Group | MS (m/z) (M$^+$ + 1) |
|---|---|---|---|
| 42 | 1 | vinyl | 349 |
| 43 | 1 | phenyl | 399 |
| 44 | 1 | 4-fluorophenyl | 417 |
| 45 | 2 | benzyl | 427 |
| 46 | 2 | vinyl | 363 |
| 47 | 2 | ethyl | 365 |

Example 48

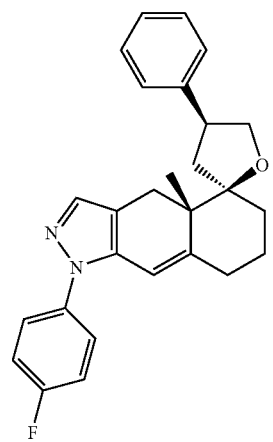

Example 41 (113 mg, 0.343 mmol) was diluted into dichloroethane (0.436 mL) and treated with triethylsilane (0.072 mL, 0.436 mmol) and trifluoroacetic acid (0.010 mL, 0.1309 mmol). The reaction mixture was maintained at 60° C. for 15 h, concentrated in vacuo, purified by preparative thin layer chromatography (250 micron SiO$_2$, 20×20 cm, 30% EtOAc-hexane) and then preparative HPLC (CHIRALPAK AD column, 4% ethanol-heptane) to provide the product which was characterized. by ¹H NMR, HPLC and mass spectrometry (m/z: 415 (M⁺+1)).

Example 49

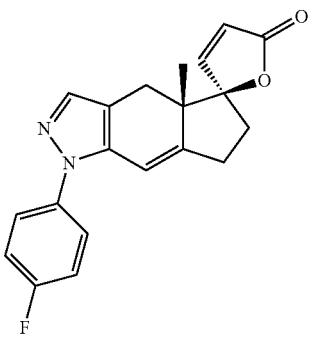

COMPOUND B was converted into a propargylic diol according to the above procedure described in Example 37. This intermediate (50 mg, 0.148 mmol) was diluted into acetone (2 mL), treated with quinoline (0.010 mL, 0.093 mmol), Lindlar catalyst (15 mg), and the reaction mixture vacuum-purged with hydrogen gas via a double-walled balloon. The reaction mixture was maintained under a hydrogen atmosphere for 15 h at 23° C., filtered over celite and concentrated in vacuo. The crude allylic diol (50 mg, 0.148 mmol) was diluted into methylene chloride (1 mL), treated with activated 4A powdered sieves, NMO (86 mg, 0.74 mmol) and catalytic TPAP (10 mg, 0.029 mmol). The reaction mixture was stirred at room temperature for 14 h, filtered over celite, partitioned between 10% aqueous $NaHSO_3$ and $CH_2Cl_2$, the organic phase washed with water, dried over anhydrous sodium sulfate and concentrated in vacuo. The residue was purified by preparative reversed phase HPLC (C18 $SiO_2$, 0-100% acetonitrile gradient in water with 0.1% TFA eluent) to provide the product hydroxyenal. This intermediate (10 mg, 0.030 mmol) was diluted into tert-butanol (0.50 mL), and 2-methyl-2-butene (0.74 mmol, 0.10 mL) was added. The reaction mixture was allowed to stir for 5 min at 23° C., and then a solution of sodium chlorite (0.089 mmol, 8 mg) and mono-basic sodium phosphate (0.074 mmol, 11 mg) in 0.20 mL of $H_2O$ was added. The reaction mixture was allowed to stir for 13 h at 23° C., and then quenched with saturated aqueous $NH_4Cl$, extracted with methylene chloride, and the organic phase dried over anhydrous sodium sulfate and concentrated in vacuo. The residue was purified by preparative thin layer chromatography (250 micron $SiO_2$, 20×20 cm, 30% EtOAc-hexane) to provide the product which was characterized by ¹H NMR, HPLC and mass spectrometry (m/z: 337 (M⁺+1)).

Examples 50-70

The following compounds were prepared under conditions similar to those described in the examples above and illustrated in Schemes 5-9. The following examples were characterized by ¹H NMR, HPLC and mass spectrometry.

| EX. | n | X | Y | Z | $R_1$ | $R_2$ | MS (m/z) (M⁺ + 1) |
|---|---|---|---|---|---|---|---|
| 50 | 1 | O | $CH_2$ | $CH_2$ | propyl | propyl | 409 |
| 51 | 1 | O | $CH_2$ | CHOH | propyl | propyl | 425 |
| 52 | 1 | O | $CH_2$ | $CH_2$ | allyl | allyl | 405 |
| 53 | 1 | O | $CH_2$ | CHOH | allyl | allyl | 421 |
| 54 | 1 | O | $CH_2$ | $CH_2$ | methyl | methyl | 353 |
| 55 | 1 | O | $CH_2$ | OHCH | methyl | methyl | 369 |
| 56 | 1 | O | $CH_2$ | C(O) | methyl | methyl | 367 |
| 57 | 1 | O | $CH_2$ | $CH_2$ | H | H | 325 |
| 58 | 1 | O | $CH_2$ | CHOH | H | H | 341 |
| 59 | 2 | $CH_2$ | O | $CH_2$ | ethyl | H | 367 |
| 60 | 2 | $CH_2$ | O | $CH_2$ | H | ethyl | 367 |
| 61 | 2 | $CH_2$ | O | $CH_2$ | H | phenyl | 415 |
| 62 | 2 | O | $CH_2$ | CH(allyl) | allyl | allyl | 459 |
| 63 | 2 | O | $CH_2$ | $CH_2$ | methyl | methyl | 367 |
| 64 | 2 | O | $CH_2$ | $CH_2$ | benzyl | benzyl | 519 |
| 65 | 2 | O | $CH_2$ | $CH_2$ | allyl | allyl | 419 |
| 66 | 2 | O | $CH_2$ | CHOH | methyl | methyl | 383 |
| 67 | 2 | O | $CH_2$ | CHOH | allyl | allyl | 435 |
| 68 | 2 | O | $CH_2$ | CH(allyl) | H | H | 379 |
| 69 | 2 | O | $CH_2$ | C(O) | methyl | methyl | 381 |
| 70 | 2 | O | $CH_2$ | C(O) | allyl | allyl | 433 |

Example 71

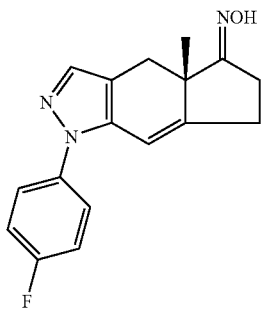

COMPOUND B (100 mg, 0.35 mmol) was diluted into pyridine (1 mL) and treated with hydroxylamine hydrochloride (28.06 mg, 0.40 mmol). The reaction mixture was maintained at 90° C. for 2 h, then partitioned between 0.1N HCl and $CH_2Cl_2$. The organic phase was dried over anhydrous sodium sulfate and concentrated in vacuo. The crude product was used directly in the subsequent reaction to generate Example 72. The product which was characterized by HPLC and mass spectrometry (m/z: 298 (M$^+$+1)).

Example 72

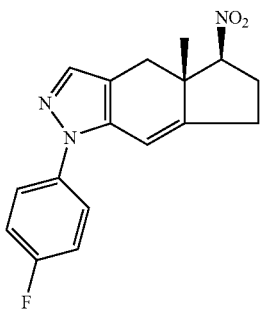

In an ice bath, Example 71 (526 mg, 1.77 mmol) was diluted into a 0° C. solution of N-bromosuccinimide (1 g, 5.62 mmol), potassium bicarbonate (556.45 mg, 5.55 mmol), H$_2$O (1 mL), and dioxane (6.33 mL). The reaction mixture was maintained at 0° C. for 48 h. After 48 h, the reaction mixture was treated with sodium borohydride (207.57 mg, 5.49 mmol). The reaction mixture was maintained at 23° C. for 0.5 h. The mixture was then partitioned between NH$_4$Cl$_{(aq)}$ and CH$_2$Cl$_2$, and the organic phase was dried over anhydrous sodium sulfate, concentrated in vacuo, and purified by preparative centrifugal thin layer chromatography (Chromatotron, 4 mm SiO$_2$, 10% to 60% ethyl acetate-hexane gradient elution) to provide the product which was characterized by $^1$H NMR, HPLC and mass spectrometry (m/z: 314 (M$^+$+1)).

Example 73

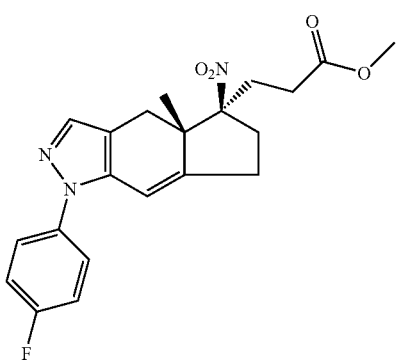

Example 72 (4 mg, 0.013 mmol) was diluted into tert-butyl alcohol (0.036 mL), treated with methyl acrylate (0.69 mL, 0.77 mmol) and then Triton B (0.018 mL, 0.040 mmol). The reaction mixture was maintained at 23° C. for 15 h and then concentrated in vacuo. The crude reaction product, which was characterized by $^1$H NMR, HPLC and mass spectrometry (m/z: 400 (M$^+$+1)), was used directly in the subsequent reaction to generate Example 74.

Example 74

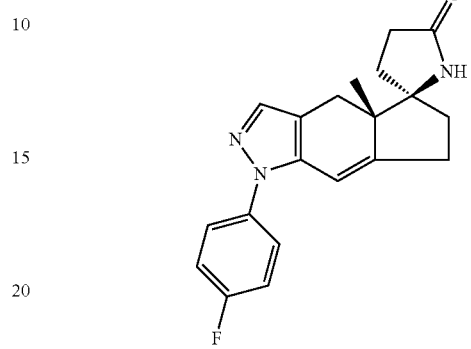

Example 73 (6 mg, 0.021 mmol) was diluted into glacial acetic acid (0.5 mL) and treated with zinc dust (22 mg, 6.8 mmol). The mixture was maintained at 25° C. for 15 h, filtered over celite and washed with CH$_2$Cl$_2$ The filtrate was concentrated in vacuo and purified by preparative reversed phase HPLC (C18 SiO$_2$, 0-100% acetonitrile gradient in water with 0.1% TFA eluent) to provide the product which was characterized by $^1$H NMR, HPLC and mass spectrometry (m/z: 338 (M$^+$+1)).

Example 75

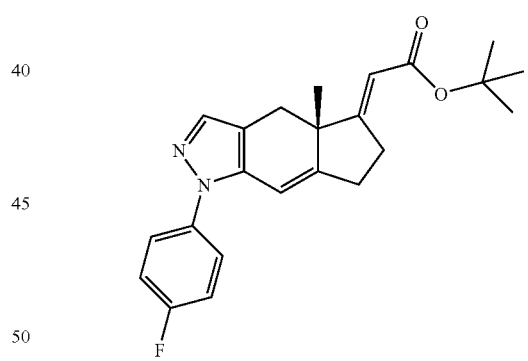

A THF (9 mL) solution of tert-butyl acetate (0.72 mL, 5.32 mmol) was treated with lithium hexamethyldisilazane (6.2 mL, 6.21 mmol, 1M THF) at −78° C. and the mixture aged for 15 min. The ester enolate was then treated with a THF (9 mL) solution of COMPOUND B (500 mg, 1.77 mmol), the mixture aged 30 min at −78° C., maintained 11 h at room temperature, and then quenched with water, partitioned with ethyl acetate, the organic phase dried over anhydrous sodium sulfate, and concentrated in vacuo. This beta-hydroxy ester intermediate was vacuum pumped dry, and the crude residue diluted into CHCl$_3$ (18 mL), cooled to 0° C., treated with Martin Sulfurane reagent (3.6 g, 5.32 mmol), and the reaction mixture was stirred at 0° C. for 3 h. The reaction mixture was warmed to 23° C., partitioned between NaHCO$_{3(aq)}$ and CHCl$_3$, the organic phase dried over anhydrous sodium sulfate, and concentrated in vacuo. The crude product was purified by preparative centrifugal thin layer chromatography (Chromatotron, 4 mm SiO$_2$, 0% to 20% ethyl acetate-hexane gradient elution) to provide the product as a (3:2) mixture of double bond isomers which was characterized by $^1$H NMR, HPLC and mass spectrometry (m/z: 381 (M$^+$+1)).

Example 76

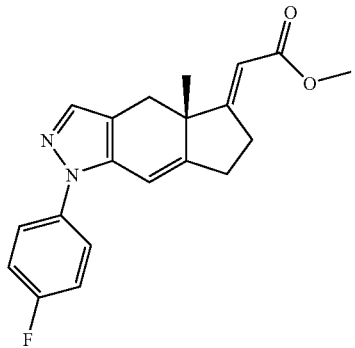

Example 75 (670 mg, 1.77 mmol) was diluted into methylene chloride (8 mL), cooled to 0° C., and treated with trifluoroacetic acid (8 mL). The reaction mixture was warmed to 23° C. for 1 h, concentrated in vacuo and vacuum pumped dry. The crude oil was diluted into diethyl ether (5 mL) and methanol (11 mL), treated at 23° C. with trimethylsilyl diazomethane (9 mL, 18 mmol, 2 M hexanes), maintained 5 min, quenched with dilute acetic acid in diethyl ether, the quench monitored by a positive TLC bromocresol green stain for excess HOAc, and the reaction mixture concentrated in vacuo. The crude product was purified by preparative centrifugal thin layer chromatography (Chromatotron, 4mm SiO$_2$, 0% to 20% ethyl acetate-hexane gradient elution) to provide the product as a (3:2) mixture of double bond isomers which was characterized by $^1$H NMR, HPLC and mass spectrometry (m/z: 339 (M$^+$+1)).

Example 77

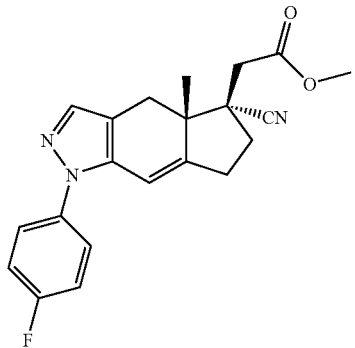

Example 76 (150 mg, 0.44 mmol) was treated with Et$_2$AlCN in toluene (13 mL, 13.3 mmol, 1M toluene) at room temperature. The reaction mixture was aged at 23° C. for 72 h, cooled to −78° C., and slowly quenched with methanol resulting in an extremely exothermic reaction. The reaction mixture was then filtered over celite, washed excessively with (1:1) MeOH-acetonitrile, and concentrated in vacuo. The crude product was purified by preparative centrifugal thin layer chromatography (Chromatotron, 2 mm SiO$_2$, 20% to 70% ethyl acetate-hexane gradient elution) to provide the product as a single diastereomer which was characterized by $^1$H NMR, HPLC and mass spectrometry (m/z: 366 (M$^+$+1)).

Example 78

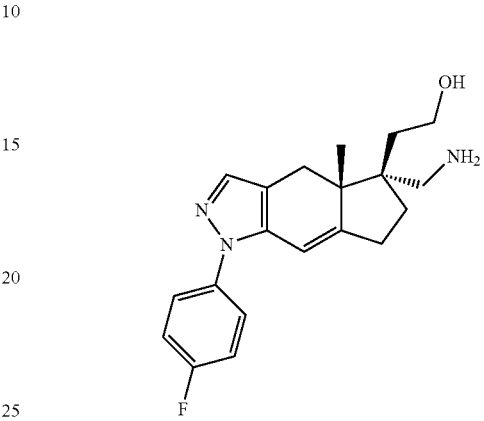

Example 77 (20 mg, 0.055 mmol) was dissolved in THF (2 mL), treated with lithium aluminum hydride (21 mg, 0.55 mmol), and the reaction mixture stirred at 23° C. for 3 h. The mixture was then quenched with a saturated solution of Rochelle's salt, solid NaCl added to aid the extraction, and excessively partitioned with methylene chloride. The organic phase was then dried over anhydrous sodium sulfate, and concentrated in vacuo to provide the product which was characterized by $^1$H NMR, HPLC and mass spectrometry (m/z: 342 (M$^+$+1)), and used directly in the next reaction to generate Example 79.

Example 79

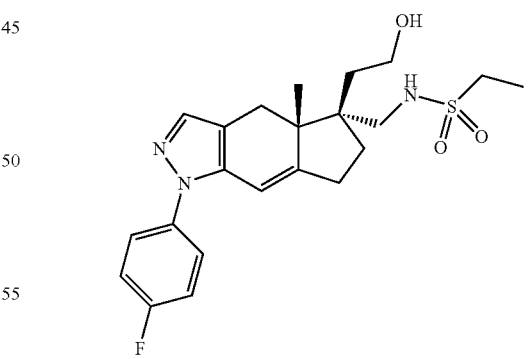

Example 78 (9 mg, 0.026 mmol) was dissolved in methylene chloride (2 mL), treated with pyridine (0.006 mL, 0.079 mmol), followed by ethanesulfonyl chloride (0.004 mL, 0.039 mmol), and the reaction mixture stirred at 23° C. for 1 h. The mixture was then either partitioned between NaHCO$_3$ (aq) and CH$_2$Cl$_2$, and used crude in the following reaction, or purified by loading the reaction mixture directly onto preparative thin layer chromatography (1500 micron SiO$_2$, 20×20 cm, 50% EtOAc-hexane) to provide the product which was characterized by ¹H NMR, HPLC and mass spectrometry (m/z: 434 (M⁺+1)).

Example 80

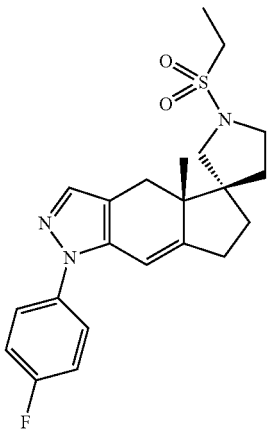

Example 79 (10 mg, 0.023 mmol) was dissolved in benzene (1 mL), treated with recrystallized triphenylphosphine (7 mg, 0.025 mmol), followed by DIAD (0.005 mL, 0.025 mmol), and the reaction mixture stirred at 23° C. for 1 h. The mixture was then concentrated in vacuo and purified by preparative reversed phase HPLC (C18 SiO₂, 0-100% acetonitrile gradient in water with 0.1% TFA eluent), followed by preparative thin layer chromatography (500 micron SiO₂, 20×20 cm, 50% EtOAc-hexane) to provide the product which was characterized by ¹H NMR, HPLC and mass spectrometry (m/z: 416 (M⁺+1)).

Example 81-83

The following compounds were prepared under conditions similar to those described in the examples above and illustrated in Scheme 14. The following examples were characterized by ¹H NMR, HPLC and mass spectrometry.

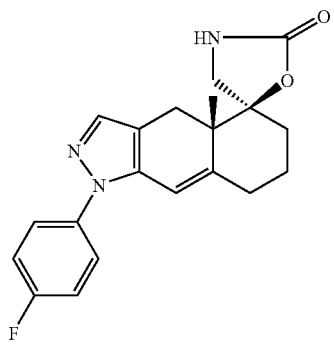

| EXAMPLE | n | R Group | MS (m/z) (M⁺ + 1) |
|---|---|---|---|
| 81 | 1 | phenyl | 464 |
| 82 | 2 | ethyl | 430 |
| 83 | 2 | phenyl | 478 |

Example 84

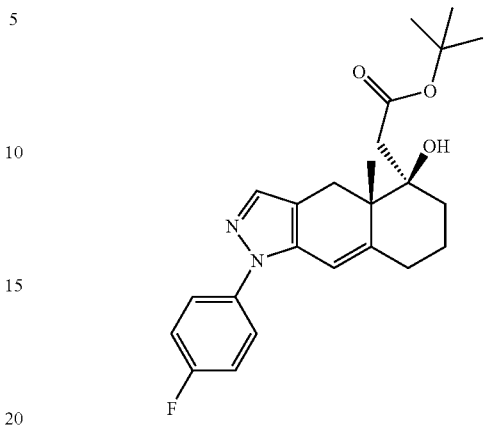

Compound A (500 mg, 1.69 mmol) was dissolved in 17 mL of anhydrous tetrahydrofuran in an oven-dried vessel under argon atmosphere. Then in a separate oven-dried vessel of t-BuOAc (5.06 mmol, 700 mL) was first cooled to −78° C. and then diluted with lithium hexamethyldisilazane (1M in THF, 5.91 mmol, 6.0 mL) under argon atmosphere. The resulting reaction mixture was allowed to stir for 5 minutes. The solution of COMPOUND A was then added dropwise to the lithium enolate solution and allowed to stir for 30 minutes. The reaction mixture was quenched at −78°C. with 20 mL of H₂O, extracted with ethyl acetate (3×20 mL), and the organic layers were dried over sodium sulfate and evaporated under reduced pressure. The crude reaction mixture was purified by flash chromatography (SiO₂, EtOAc/hexanes) to give the desired product as an orange viscous oil. The product was characterized by ¹H NMR, HPLC and mass spectroscopy (m/z: 413 (M⁺+1)).

Example 85

Example 84 (600 mg, 1.46 mmol) was dissolved in 11 mL of anhydrous methylene chloride under argon atmosphere and cooled to 0° C. Then an equi-volume of trifluoroacetic acid (11 mL) was added dropwise, and the resulting reaction mixture was allowed to slowly warm to 23° C. over 2 h. The reaction mixture was evaporated under reduced pressure, and the crude acid product was characterized by ¹H NMR, HPLC and mass spectroscopy (m/z 357 (M⁺+1)). This intermediate (518 mg, 1.46 mmol) was dissolved in 7 mL of anhydrous methylene chloride under argon atmosphere. Then triethyl amine (4.37 mmol, 0.630 mL) was added followed by diphenylphosphoryl azide (2.18 mmol, 0.462 mL). The resulting reaction mixture was allowed to stir over the duration of 3 days and, then was evaporated under reduced pressure. The crude reaction mixture was purified by flash chromatography (SiO$_2$, EtOAc/hexanes) to give the desired product which was characterized by $^1$H NMR, HPLC and mass spectroscopy (m/z: 354 (M$^+$+1)).

Example 86

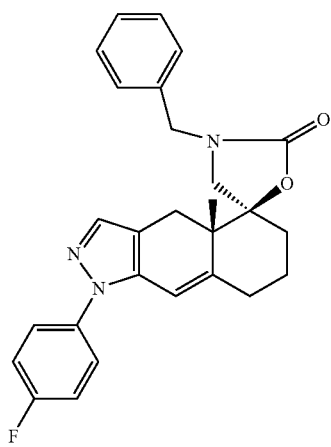

Example 85 (50 mg, 0.14 mmol) was dissolved in 0.70 mL of anhydrous DMF under an argon atmosphere, and benzyl bromide (0.57 mmol, 0.067 mL) was added followed by sodium hydride (60% in mineral oil, 0.28 mmol, 11 mg). The resulting reaction mixture was allowed to stir for 45 minutes. The reaction was quenched with 1 mL of H$_2$O, extracted with ethyl acetate (3×2 mL) and then the resulting organic layers were dried over sodium sulfate and evaporated under reduced pressure. The crude reaction mixture was purified by flash chromatography (SiO$_2$, EtOAc/hexanes) to give the desired product which was characterized by $^1$H NMR, HPLC and mass spectroscopy (m/z: 444 (M$^+$+1)).

Examples 87-92

The following compounds were prepared under conditions similar to those described in the examples above and illustrated in Scheme 15. The following examples were characterized by $^1$H NMR, HPLC and mass spectrometry.

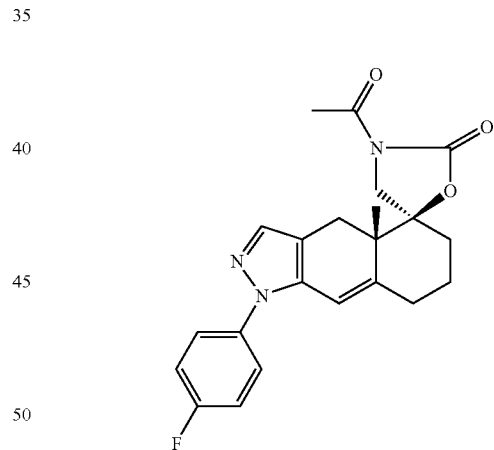

| EXAMPLE | R Group | MS (m/z) (M$^+$ + 1) |
|---|---|---|
| 87 | methyl | 368 |
| 88 | allyl | 394 |
| 89 | isopropyl | 396 |
| 90 | 2-methoxyethyl | 412 |
| 91 | CH$_2$CO$_2$Et | 440 |
| 92 | 2-(1,3-dioxan)ethyl | 468 |

Example 93

Example 85 (50 mg, 0.14 mmol) was dissolved in 0.70 mL of anhydrous tetrahydrofuran under argon atmosphere. Then triethyl amine (0.57 mmol, 0.082 mL) was added followed by acetic anhydride (0.28 mmol, 0.027 mL). Next, the reaction mixture was treated with a catalytic amount of DMAP and allowed to stir for 12 h. The reaction mixture was quenched with 1 mL of H$_2$O, extracted with ethyl acetate (3×2 mL) and then the resulting organic layers were dried over sodium sulfate and evaporated under reduced pressure. The crude reaction product was purified by flash chromatography (SiO$_2$, EtOAc/hexanes) to give the desired product which was characterized by $^1$H NMR, HPLC and mass spectroscopy (m/z: 396 (M$^+$+1)).

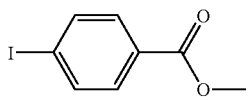

COMPOUND 1

4-Iodobenzoic acid (100 mg, 0.40 mmol) was dissolved in methanol. Then 4.0 equiv. of trimethylsilyl diazomethane (2.0 M in hexanes, 1.61 mmol, 0.800 mL) was slowly added until a yellow color remained, and the reaction mixture was allowed to stir for 1 h. The reaction mixture was quenched with HOAc and evaporated under reduced pressure and the resulting oil was partitioned between $H_2O$ and $CH_2Cl_2$. The aqueous layer was then extracted with methylene chloride (3×2 mL) and the resulting organic layers were dried over sodium sulfate and evaporated under reduced pressure. The product was characterized by $^1$H NMR.

Example 94

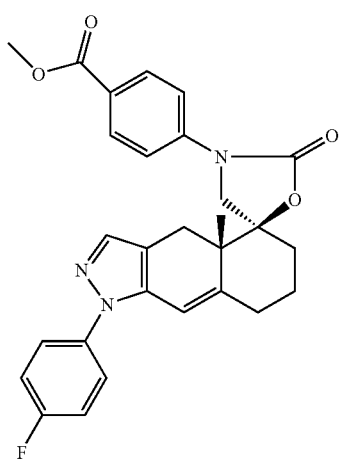

Example 85 (50 mg, 0.14 mmol) was tared into a sealed pressure tube and 1 mol % of copper(I) iodide (0.014 mmol, 3 mg) and potassium phosphate (0.283 mmol, 60 mg) were added. The reactants of the tube were then diluted with 0.50 mL of anhydrous dioxane under an argon atmosphere, and trans 1,2-diaminocyclohexane (0.0014 mmol, 0.170 mL) was added followed by COMPOUND 1 (0.14 mmol, 37 mg). The reaction mixture was heated to 110° C. and allowed to stir for 12 h before it was filtered over $SiO_2$, washed with EtOAc (5 mL) and evaporated under reduced pressure. The crude reaction product was purified by flash chromatography ($SiO_2$, EtOAc/hexanes) and characterized by $^1$H NMR, HPLC and mass spectrometry (m/z: 488 ($M^+$+1)).

Example 95

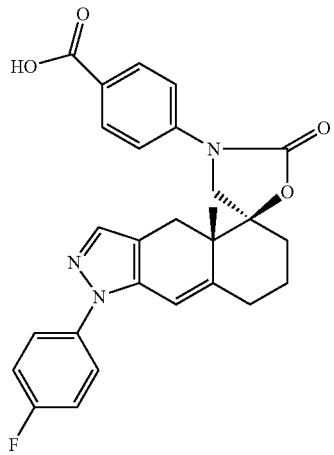

Example 94 (20 mg, 0.041 mmol) was dissolved in 0.410 mL of a mixture of $H_2O$:THF:MeOH (1:3:1). Then LiOH (1 M in $H_2O$, 0.16 mmol, 0.16 mL) was added, and the reaction mixture was allowed to stir for 12 h. The reaction mixture was then neutralized with 1 N HCl (0.16 mL) and followed by the addition of 0.30 mL of chloroform. The solution was then dried over sodium sulfate and evaporated under reduced pressure. The crude reaction product was purified by flash chromatography ($SiO_2$, EtOAc/hexanes) and characterized by $^1$H NMR, HPLC and mass spectrometry (m/z: 474 ($M^+$+1)).

Examples 96-97

The following examples were prepared under conditions similar to those described in the example above and illustrated in Scheme 15. The following examples were characterized by $^1$H NMR, HPLC and mass spectroscopy.

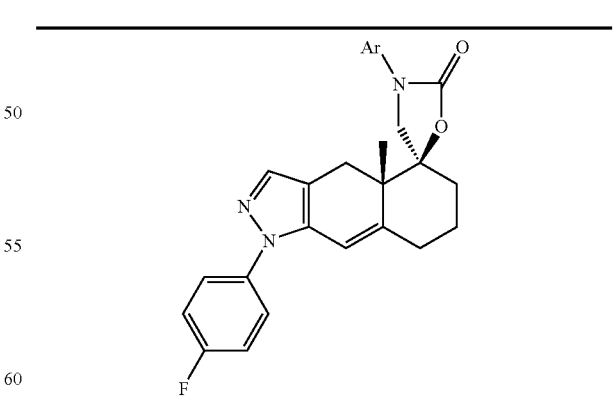

| EXAMPLE | Ar-Group | MS (m/z) ($M^+$ + 1) |
|---|---|---|
| 96 | phenyl | 430 |
| 97 | 3-carboxyphenyl | 474 |

Example 98

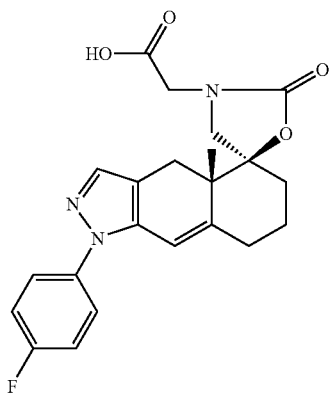

Example 91 (59 mg, 0.13 mmol) was dissolved in 1.3 mL of a mixture of $H_2O$:THF:MeOH (1:3:1). Then LiOH (1 M, 0.54 mmol, 500 uL) was added, and the reaction mixture was allowed to stir for 12 h. The reaction mixture was then neutralized with 1 N HCl and followed by the addition of 1.5 mL of chloroform. The solution was then dried over sodium sulfate and evaporated under reduced pressure. The product was characterized by $^1$H NMR, HPLC and mass spectrometry (m/z: 412 (M$^+$+1)).

Example 99

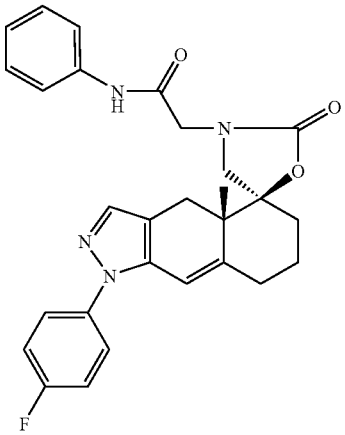

Example 98 (30 mg, 0.073 mmol) was dissolved in 0.70 mL of anhydrous methylene chloride under an argon atmosphere and o-7-azabenzotriazol-1-yl)-N,N,N',N'-tetramethyluronium hexafluorophosphate (0.15 mmol, 56 mg) was added. Then aniline (0.73 mmol, 0.067 mL) was added followed by diisopropylethyl amine (1.09 mmol, 0.191 mL). The resulting reaction mixture was allowed to stir for 4 h at 23° C. The reaction mixture was quenched with 1 mL of aqueous $NaHCO_3$, extracted with methylene chloride (3×2 mL) and then the resulting organic layers were dried over sodium sulfate and evaporated under reduced pressure. The crude reaction product was purified by flash chromatography (SiO$_2$, acetone/hexanes) and characterized by $^1$H NMR, HPLC and mass spectrometry (m/z: 487 (M$^+$+1)).

Example 100

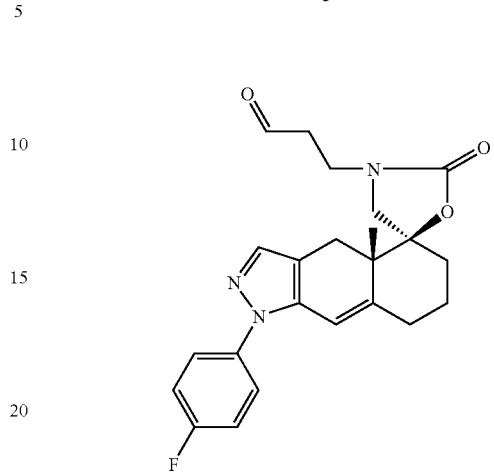

Example 92 (12 mg, 0.026 mmol) was dissolved in 0.80 mL of tetrahydrofuran. Then 2N aqueous HCl (0.39 mmol, 193 uL) was added, and the reaction was heated to 85° C. and allowed to stir fro 12 h. The reaction was quenched with 1 mL of $H_2O$, extracted with diethyl ether (3×2 mL) and the organic layers were dried over sodium sulfate and evaporated under reduced pressure. The crude reaction product was purified by flash chromatography (SiO$_2$, acetone/hexanes) and characterized by $^1$H NMR, HPLC and mass spectrometry (m/z: 410 (M$^+$+1)).

Example 101

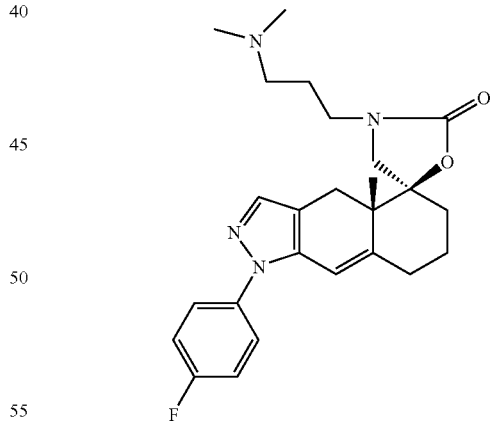

Example 100 (10 mg, 0.024 mmol) was dissolved in 0.70 mL of anhydrous methylene chloride under argon atmosphere and NaBH(OAc)$_3$ (0.049 mmol, 10 mg) was added. Then diisopropylethyl amine (0.073 mmol, 0.013 mL) was added followed by dimethylamine (0.037 mmol, 0.018 mL, 2 M THF). The resulting reaction mixture was allowed to stir for 12 h at 23° C., quenched with 1 mL of aqueous NaHCO$_3$, extracted with methylene chloride (3×2 mL), and the organic layers were dried over sodium sulfate and evaporated under reduced pressure. The crude reaction product was purified by flash chromatography (SiO$_2$, acetone/hexanes) and characterized by $^1$H NMR, HPLC and mass spectrometry (m/z: 439 (M$^+$+1)).

Example 102

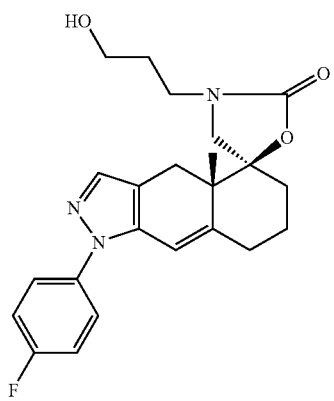

Example 100 (10 mg, 0.024 mmol) was dissolved in 0.122 mL of anhydrous toluene under argon atmosphere and cooled to −78° C. Then DIBAL-H (0.049 mmol, 0.050 mL, 1 M toluene) was added, and the reaction mixture was stirred for 30 min at −78° C. The reaction mixture was quenched with 0.500 mL of Rochelle's salt, extracted with methylene chloride (3×1 mL), and the organic layers were dried over sodium sulfate and evaporated under reduced pressure. The crude reaction product was purified by flash chromatography (SiO$_2$, acetone/hexanes) and characterized by $^1$H NMR, HPLC and mass spectrometry (m/z: 412 (M$^+$+1)).

Example 103

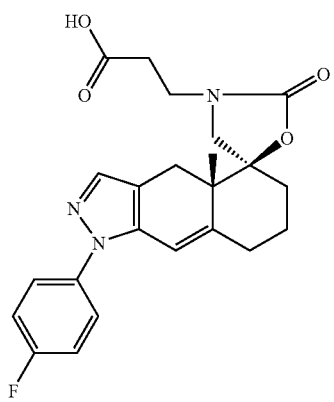

Example 100 (10 mg, 0.024 mmol) was diluted in 0.350 mL of t-BuOH and 2-methyl-2-butene (0.61 mmol, 0.061 mL) was added. The reaction mixture was allowed to stir for 5 min at 23° C., and then a solution of sodium chlorite (0.073 mmol, 7 mg) and mono-basic sodium phosphate (0.061 mmol, 10 mg) in 0.140 mL of H$_2$O was added. The reaction mixture was allowed to stir for 3 h at 23° C., and then quenched with 1 mL of aqueous NH$_4$Cl, extracted with methylene chloride (3×1 mL) and the organic layers were dried over sodium sulfate and evaporated under reduced pressure. The crude reaction product was purified by flash chromatography (SiO$_2$, EtOAc/hexanes) and characterized by $^1$H NMR, HPLC and mass spectrometry (m/z: 426 (M$^+$+1)).

Example 104

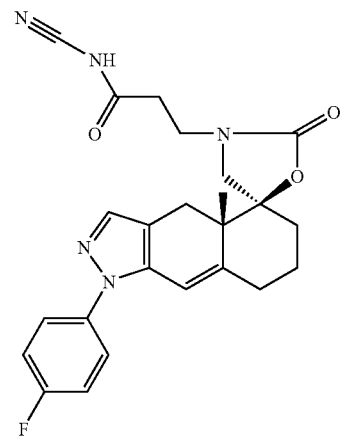

Example 103 (8 mg, 0.019 mmol) was dissolved in 0.250 mL of anhydrous methylene chloride under an argon atmosphere and cooled to 0° C. Then cyanamide (0.028 mmol, 1.2 mg) was added followed by diisopropylethyl amine (0.056 mmol, 0.010 mL), and EDCI (0.021 mmol, 4 mg). The reaction mixture was allowed to slowly warm to 23° C. over 12 h, then quenched with 0.500 mL of aqueous NH$_4$Cl, extracted with methylene chloride (3×0.500 mL), and then the organic layers were dried over sodium sulfate and evaporated under reduced pressure. The crude reaction product was purified by flash chromatography (SiO$_2$, acetone/hexanes) and characterized by $^1$H NMR, HPLC and mass spectrometry (m/z: 450 (M$^+$+1)).

Examples 105 and 106

Example 103 (15 mg, 0.035 mmol) was dissolved in 0.70 mL anhydrous chloroform which was first filtered through basic alumina under an argon atmosphere. A molar equivalent of methanesulfonamide or benzenesulfonamide was added. Then diisopropylethyl amine (0.35 mmol, 0.061 mL) was added followed by PyBOP (0.18 mmol, 92 mg) and a catalytic amount of DMAP. The resulting reaction mixture was allowed to stir at 23° C. for 5 h. The reaction mixture was quenched with 1 mL of aqueous NaHCO$_3$, extracted with methylene chloride (3×1 mL) and then the resulting organic layers were dried over sodium sulfate and evaporated under reduced pressure. The crude reaction product was purified by flash chromatography (SiO$_2$, acetone/hexanes). The examples made through this procedure are outlined below and were characterized by $^1$H NMR, HPLC and mass spectroscopy.

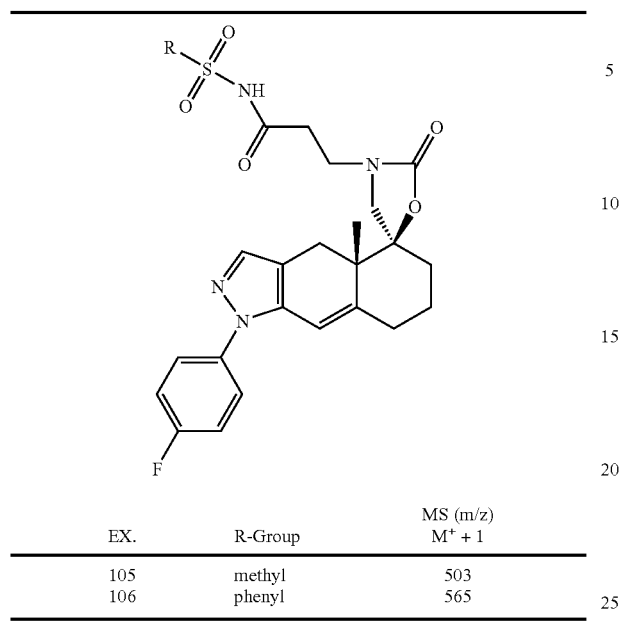

| EX. | R-Group | MS (m/z) M⁺ + 1 |
|---|---|---|
| 105 | methyl | 503 |
| 106 | phenyl | 565 |

Examples 107 and 108

EXAMPLE 107

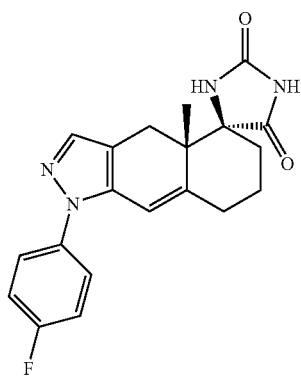

EXAMPLE 108

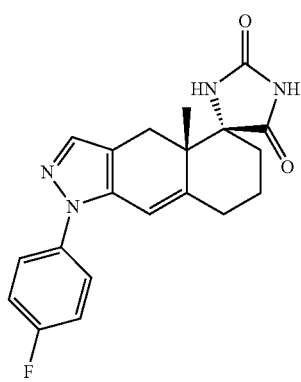

In 6 mL of H₂O was dissolved 4.0 equiv of potassium cyanide (5.4 mmol, 356 mg) and 10 equiv of ammonium carbonate (13.5 mmol, 1.3 g). To this was added COMPOUND A (400 mg, 1.35 mmol) in 6 mL of ethanol. The reaction mixture was degassed with argon and heated to 125° C. for 48 h. The reaction mixture was then cooled to 23° C., quenched with 50 mL of H₂O, extracted with methylene chloride (3×50 mL) and the organic layers were dried over sodium sulfate and evaporated under reduced pressure. The crude reaction product was purified by column chromatography (SiO₂, MeOH/CH₂Cl₂) to give the separated hydantoin isomers as white solids which were each characterized by ¹H NMR, HPLC and mass spectrometry (m/z: 367 (M⁺+1)).

Example 109

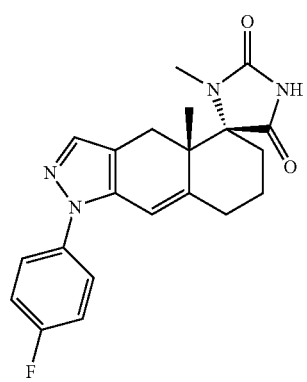

Example 108 (20 mg, 0.056 mmol) was dissolved in 0.5 mL of acetone and 0.5 mL of ethanol under argon atmosphere, and potassium carbonate (0.066 mmol, 9 mg) was added. After 5 min, methyl iodide (0.083 mmol, 0.006 mL) was added, and the reaction mixture was warmed to 60° C. for 2 h before cooling to room temperature. The reaction mixture was then quenched by the addition of 25 mL of saturated aqueous NH₄Cl, extracted with methylene chloride (3×20 mL), and the organic layers were dried over sodium sulfate and evaporated under reduced pressure. The crude reaction product was purified by column chromatography (SiO₂, methanol/CH₂Cl₂) and characterized by ¹H NMR, HPLC and mass spectrometry (m/z: 381 (M⁺+1)).

Example 110

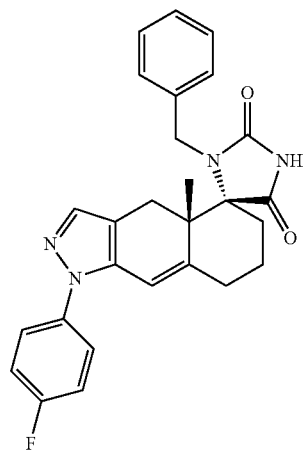

Example 110 was prepared from Example 108 according to the above procedure described in Example 109. The product was characterized by $^1$H NMR, HPLC and mass spectrometry (m/z: 457 (M$^+$+1)).

Example 111

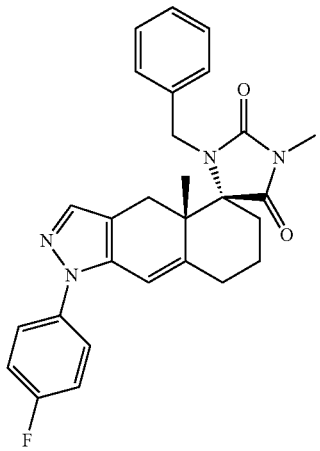

Example 110 (14 mg, 0.031 mmol) was dissolved in 0.5 mL DMF under argon atmosphere and cooled to 0° C. To this was added sodium hydride [60% in mineral oil] (0.093 mmol, 4 mg) and methyl iodide (0.155 mmol, 0.011 mL), and the reaction mixture was allowed to warm to 23° C. over 5 h. The reaction mixture was then quenched by the addition of 20 mL of saturated aqueous NH$_4$Cl, extracted with methylene chloride (3×20 mL) and the organic layers were dried over sodium sulfate and evaporated under reduced pressure. The crude reaction product was purified by column chromatography, (SiO$_2$, methanol/CH$_2$Cl$_2$) and characterized by $^1$H NMR, HPLC and mass spectrometry (m/z: 471 (M$^+$+1)).

Example 112

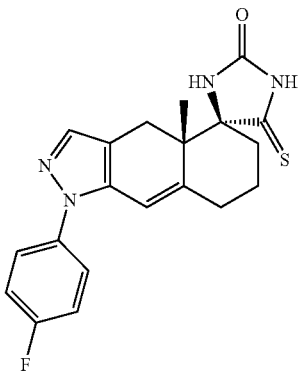

Example 107 (10 mg, 0.027 mmol) was dissolved in 0.5 mL of dioxane under an argon atmosphere and P$_2$S$_5$ (0.082 mmol, 18 mg) was added and the reaction mixture was heated to 110° C. for 5 h before it was cooled to room temperature, and then evaporated under reduced pressure. The crude reaction product was purified by column chromatography (SiO$_2$, methanol/CH$_2$Cl$_2$) and characterized by $^1$H NMR, HPLC and mass spectrometry (m/z: 383 (M$^+$+1)).

Example 113

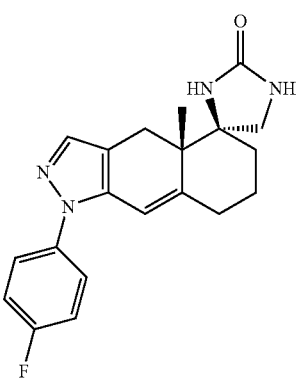

Example 112 (5 mg, 0.013 mmol) was dissolved in 0.5 mL of ethanol and catalytic Raney nickel was added, and the reaction mixture was heated to 65° C. for 1 h before it was cooled to 23° C. The reaction mixture was then filtered through celite, washed with ethyl acetate (10 mL) and evaporated under reduced pressure. The crude reaction product was purified by column chromatography (SiO$_2$,methanol/CH$_2$Cl$_2$) and characterized by $^1$H NMR, HPLC and mass spectrometry (m/z: 353 (M$^+$+1)).

Examples 114-136

The following examples were prepared under conditions similar to those described in the examples above and illustrated in Schemes 19-21. The following examples were characterized by $^1$H NMR, HPLC, and mass spectroscopy.

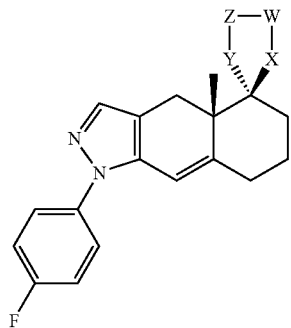

| EX. | W | X | Y | Z | MS (m/z) (M+[+1]) |
|---|---|---|---|---|---|
| 114 | C(O) | NCH₃ | C(O) | NH | 381 |
| 115 | NCH₂Ph | C(O) | NCH₃ | C(O) | 471 |
| 116 | NCH₃ | C(O) | NCH₃ | C(O) | 395 |
| 117 | NCH₂CH=CH₂ | C(O) | NCH₃ | C(O) | 421 |
| 118 | C(O) | NCH₃ | C(O) | NCH₂Ph | 471 |
| 119 | C(O) | NCH₃ | C(O) | NCH₃ | 395 |
| 120 | C(O) | NCH₃ | C(O) | NCH₂CH=CH₂ | 421 |
| 121 | C(O) | NCH₃ | C(O) | NH | 381 |
| 122 | N(CH₂)₂CO₂H | C(O) | NCH₂Ph | C(O) | 529 |
| 123 | NH | C(O) | N(CH₂)₂CO₂H | C(O) | 439 |
| 124 | NH | C(O) | N(CH₂)₂-[1,3-dioxan-2-yl] | C(O) | 481 |
| 125 | C(O) | NCH₃ | C(O) | N(CH₂)₂CO₂H | 453 |
| 126 | C(O) | NCH₃ | C(O) | N(CH₂)₂-[1,3-dioxan-2-yl] | 495 |
| 127 | NCH₂CH=CH₂ | C(O) | NCH₂CH=CH₂ | C(O) | 447 |
| 128 | NCH₂Ph | C(O) | NCH₂Ph | C(O) | 547 |
| 129 | NH | C(S) | NCH₂Ph | C(O) | 473 |
| 130 | NH | C(S) | NH | C(O) | 383 |
| 131 | NH | C(S) | NCH₂CH=CH₂ | C(O) | 423 |
| 132 | NH | C(S) | NCH₃ | C(O) | 397 |
| 133 | NH | CH₂ | NCH₂Ph | C(O) | 443 |
| 134 | NH | CH₂ | NH | C(O) | 353 |
| 135 | C(O) | NCH₃ | CH₂ | NCH₃ | 381 |
| 136 | NH | CH₂ | NCH₃ | C(O) | 367 |

Compound C

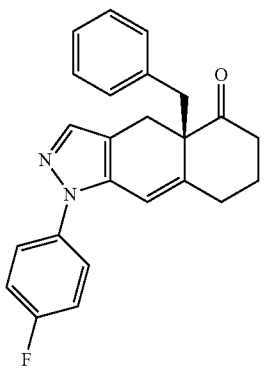

Step 1:

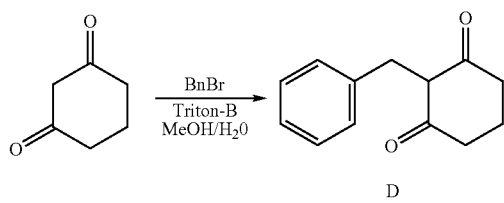

Triton B (benzyltrimethylammonium hydroxide (29.8 g, 74.6 mL of a 40 wt. % solution in MeOH, 178 mmol) was added to a solution of 1,3-cyclohexanedione in water (90 mL) followed by benzyl bromide (36.6 g, 25.5 mL, 214 mmol) at room temperature. The two phase mixture was stirred vigorously overnight after which time the product crystallized and was collected by filtration and washed with $CH_2Cl_2$ (50 mL) to give COMPOUND D (13.38 g). The filtrate was concentrated in vacuo and purified by flash chromatography (110 g Si, 50 mL/min, isocratic at 100% hexane for 5 min, gradient to 50% EtOAc in hexanes over 10 min, gradient to 80% EtOAc in hexanes over 30 min) to give further COMPOUND D (3.79 g, total yield 48%) as a colorless solid. LCMS (ES+) 203 (M+H)$^+$; $^1$H NMR (DMSO-$d_6$, 500 MHz) δ 7.16 (4H, m), 7.07 (1H, m), 3.57 (3H, br s), 2.35 (4H, br s), 1.83 (2H, quintet, J 6.2 Hz).

Step 2:

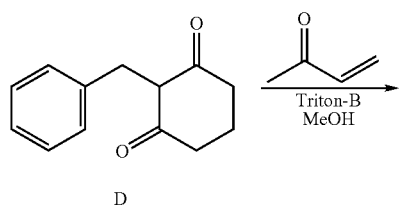

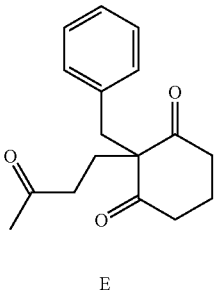

Methyl vinyl ketone (2.48 g, 2.94 mL, 35.3 mmol) was added to a solution of COMPOUND D (6.69 g, 23.6 mmol) in MeOH (20 mL) followed by Triton B (0.394 g, 0.985 mL of a 40 wt. % solution in MeOH, 2.36 mmol). The reaction was stirred at 60° C. for 6 h then overnight at room temperature after which time the product crystallized. The product was collected by filtration and washed with MeOH to afford COMPOUND E (3.97 g, 44%) as colorless solid. LCMS (ES+) 272 (M+H)$^+$; $^1$H NMR (CDCl$_3$, 500 MHz) δ 7.19 (3H, m), 6.98 (2H, m), 3.05 (2H, s), 2.47 (2H, ddd, J 17.1, 7.8, 4.7 Hz), 2.27 (2H, t, J 7.3 Hz), 2.15 (2H, ddd, J 17.2, 8.8, 4.9 Hz), 2.12 (2H, t, J 7.3 Hz), 1.71 (1H, m), 1.34 (1H, m).

Step 3:

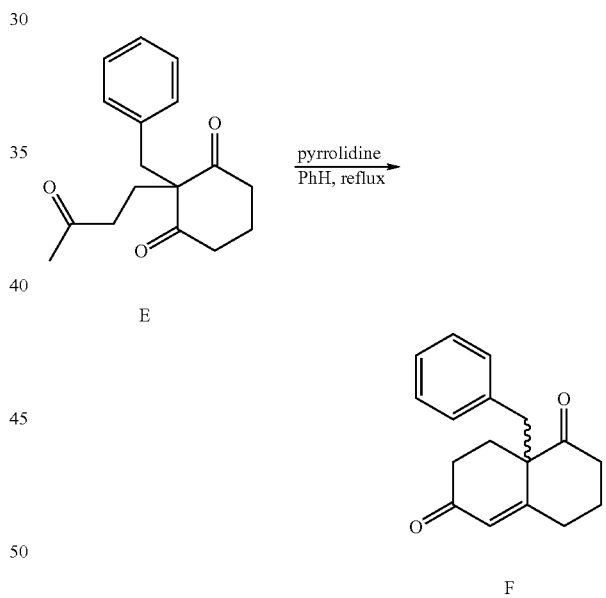

A solution of Compound E (5.47 g, 20.1 mmol) was heated at reflux in benzene (100 mL) with a Dean Stark apparatus attached. Water was azeotroped and the reaction was removed from reflux before adding pyrrolidine (1.43 g, 1.67 ml, 20.1 mmol). The reaction was heated at reflux for 2 h after which time water was azeotroped from the reaction. The reaction was allowed to cool and Et$_2$O (100 mL) was added. The mixture was washed with 1N HCl (100 mL) followed by water (100 mL). The aqueous layers were back extracted with Et$_2$O (2×100 mL) and the combined organic layers were washed with brine (100 mL) dried (MgSO$_4$) and concentrated in vacuo to afford recovered starting material (0.792 g). The aqueous layer was extracted with EtOAc (3×100 mL) and the combined extracts were dried (MgSO$_4$) then concentrated in vacuo to afford COMPOUND F (0.683 g) as a colorless solid. The aqueous layer was further extracted with CH₂Cl₂ (4×200 mL) and the combined extracts were dried (MgSO₄) then concentrated in vacuo to afford more of the desired COMPOUND F as the pyrollidine imminium chloride salt at the 1-position (4.797 g). A solution of this compound in AcOH (4 mL), MeOH (50 mL) and water (10 mL) containing NaOAc (4.0 g) was heated at reflux overnight. The solvents were removed in vacuo, the residue was treated with 1N HCl (100 mL) and the product was extracted with CH₂Cl₂ (3×200 mL). The combined organic extracts were washed with dilute aqueous Na₂CO₃ and water, dried (Na₂SO₄) and concentrated in vacuo to afford further COMPOUND F (2.348 g, total yield 59%) as a solid. LCMS (ES+) 255 (M+H)⁺; ¹H NMR (CDCl₃, 500 MHz) δ 7.28 (3H, m), 7.05 (2H, m), 5.98 (1H, br s), 3.22 (1H, d, J 13.6 Hz), 3.16 (1H, d, J 13.6 Hz), 2.72 (1H, m), 2.66 (1H, m), 2.60 (1H, m), 2.54 (1H, m), 2.40 (1H, m), 2.31 (1H, m), 2.16 (1H, m), 2.11(1H, m), 2.02 (1H, dt, J 14.2, 5.7 Hz), 1.72 (1H, m).

Step 4:

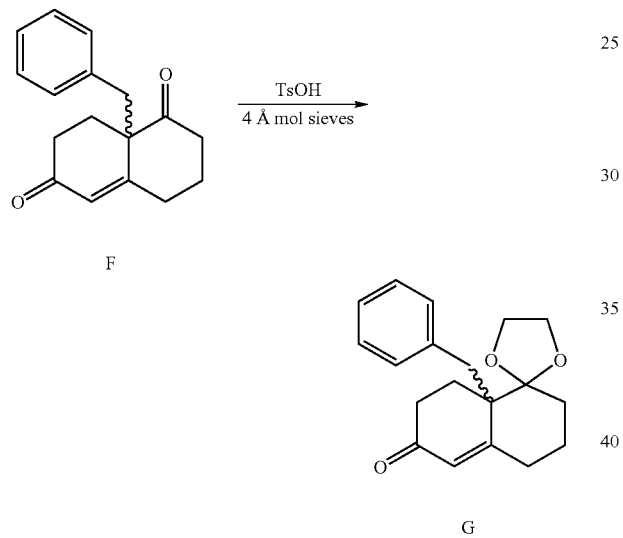

p-Toluenesulfonic acid monohydrate (0.749 g, 3.93 mmol) was added quickly in one portion to a solution of COMPOUND F (1.00 g, 3.93 mmol) in ethylene glycol (19.6 mL) containing 4 Å molecular sieves. The resulting solution was stirred at room temperature for 23 min, after which time it was poured into a mixture of ice and saturated NaHCO₃ (100 mL). The solution as extracted with EtOAc ( 1×200 mL, 2×100 mL), the combined organic layers were washed with brine (100 mL) and the brine layer was back extracted with EtOAc (100 mL). The combined organic extracts were dried (MgSO₄) and concentrated in vacuo to give a crude oil (~1.3 g). This was purified by flash chromatography (110 g Si, 70 mL/min, gradient from 0 to 40% EtOAc in hexanes over 40 min) followed by firther flash chromatography on the fractions containing the desired product (35 g Si, 40 mL/min, 20% EtOAc in hexanes to give COMPOUND G (275.0 mg, 23%) as a colorless oil. LCMS (ES+) 299 (M+H)⁺; ¹H NMR (CDCl₃, 500 MHz) δ 7.19 (3H, m), 7.12 (2H, m), 5.94 (1H, d, J 1.5 Hz), 4.00 (4H, m), 3.33 (1H, d J 13.5 Hz), 3.03 (1H, d, J 13.5 Hz), 2.77 (1H, tdd, J 13.8, 6.3, 1.7 Hz), 2.38 (1H, m), 2.26 (1H, tdd, J 13.5, 6.1, 1.2 Hz), 2.06-1.67 (6H, m), 1.04 (1H, ddd, J 16.8, 13.3, 6.5 Hz).

Step 5:

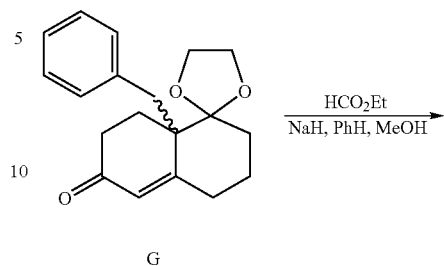

COMPOUND G (275 mg, 0.923 mmol) was dissolved in benzene (20 mL) and ~5 mL was distilled off azeotropically to dry the solvent. The solution was cooled to ~10° C. and ethyl formate (288.1 mg, 314 μL, 3.69 mmol) was added followed by NaH (147 mg of a 60% dispersion in oil 3.69 mmol). After 3 min MeOH (20 μL) was added and the reaction mixture became brown. The reaction was stirred at room temperature for 3 h, then cooled to 0° C. and water (50 mL) was added slowly. Et₂O (50 mL) was added and the organic layer was washed with water (3×50 mL). The combined aqueous phases were washed with Et₂O (100 mL) and acidified to pH 5.5-6 with saturated KH₂PO₄ (~20 mL) followed by addition of 3N HCl (18 mL). The aqueous layer was extracted with EtOAc (3×100 mL) and the combined organic extracts were dried (Na₂SO₄) and concentrated in vacuo to afford COMPOUND H (222.1 mg, 74%) as a brown oil. This was used in the next step without any further purification. LCMS (ES+) 327 (M+H)⁺.

Step 6:

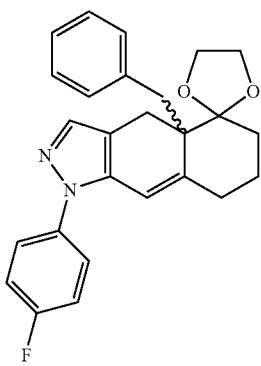

Example 139 p-Fluorophenyl hydrazine hydrochloride (166.2 mg, 0.681 mmol) and NaOAc (139.1 mg, 1.02 mmol) were successively added to a solution of COMPOUND H (222.1 mg, 0.681 mmol) in acetic acid (10 mL) at room temperature under $N_2$. The mixture was stirred at room temperature overnight and then added slowly to a 10% saturated $NaHCO_3$ solution (100 nL). Saturated $NaHCO_3$ was added dropwise until effervescence ceased. The aqueous mixture was extracted with EtOAc (3×100 mL) and the combined organic extracts were washed with brine (100 mL), dried ($MgSO_4$) and concentrated in vacuo to afford the crude product. This was purified by flash chromatography (35 g Si, 40 mL/min, isocratic at 100% hexanes for 5 min, gradient to 20% EtOAc over 25 min, isocratic at 20% EtOAc in hexanes for 10 min) to give Example 139 (162.3 mg, 57%) as a colorless oil. LCMS (ES+) 417 (M+H)+; 1H NMR (CDCl3, 500 MHz) δ 7.10 (6H, m), 6.99 (4H, m), 6.14 (1H, d, J 2.1 Hz), 4.07 (4H, m), 3.28 (1H, d, J 16.6 Hz), 3.10 (1H, d, J 13.2 Hz), 2.85 (1H, d, J 13.0 Hz), 2.80 (1H, d, J 16.5 Hz), 2.71 (1H, tdd J 14.0, 5.6, 2.4 Hz), 2.35 (1H, br d, J 15.2 Hz), 1.97 (1H, td, J 13.5, 4.6 Hz), 1.86-1.67 (3H, m).

Step 7:

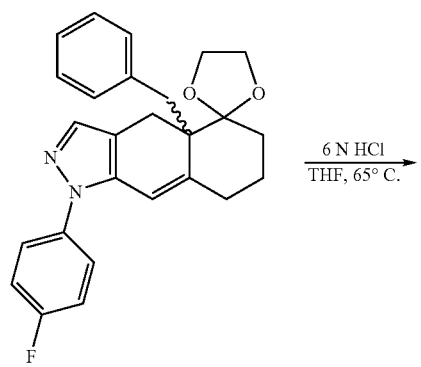

Example 139

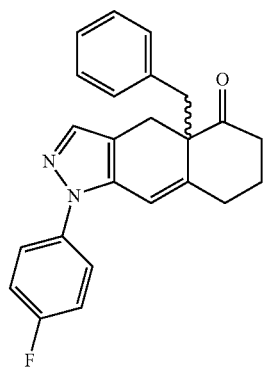

C

6N HCl (0.26 mL, 1.55 mmol) was added to a solution of Example 12 (161 mg, 0.387 mmol) in THF (10 mL) and the resulting solution was heated at reflux for 5 h. The reaction mixture was cooled and added slowly to 10% saturated $Na_2CO_3$ (100 mL). The resulting nixture was extracted with EtOAc (3×100 mL). The combined organic phases were dried ($MgSO_4$) and concentrated in vacuo to afford the crude product (172.6 mg). This was purified by flash chromatography (10 g Si, 25 ml/min, isocratic at 100% hexanes for 4 mi, gradient to 20% EtOAc in hexanes over 30 min, isocratic at 20% EtOAc in hexanes for 10 min) to give ketone C (128.2 mg, 89%) as a colorless oil. Ketone C was resolved into its two enantiomers by chiral HPLC (OD, 20×250 mm, isocratic at 3% EtOH in heptane) to give (R)-COMPOUND C and (S)—COMPOUND C (67.1 and 61.6 mg respectively) in order of elution. LCMS (ES+) 373 (M+H)+; 1H NMR (CDCl3, 500 MHz) δ 7.45 (3H, m), 7.20 (5H, m), 6.98 (2H, m), 6.38 (1H, br d, J 1.9 Hz), 3.03 (1H, d, J 13.1 Hz), 3.02 (1H, d, J 16.6 Hz), 2.85 (1H, d, J 13.3 Hz), 2.71 (1H, d, J 16.6 Hz), 2.61 (1H, m), 2.55 (1H, dd, J 12.7, 5.9 Hz), 2.51 (1H, m), 2.37 (1H, m), 2.00 (1H, m), 1.64 (1H, qt, J 13.1, 4.3 Hz).

COMPOUND I

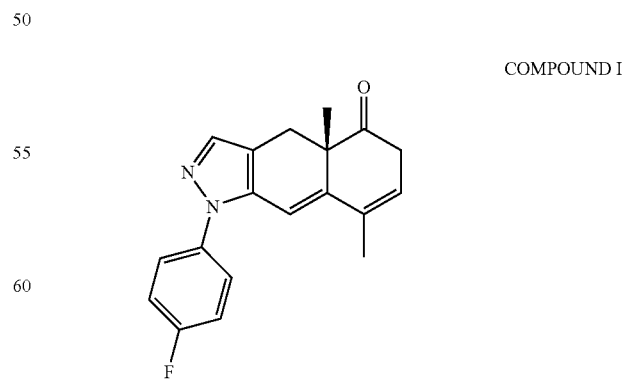

Step 1:

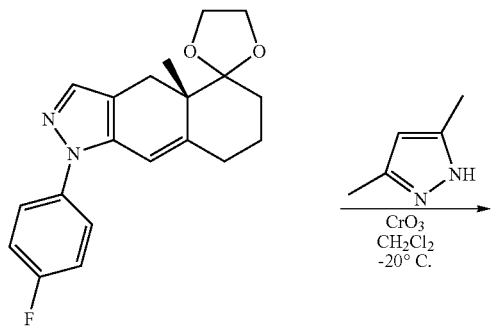

Example 138

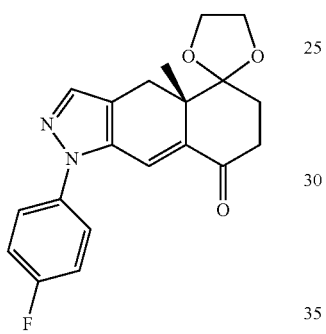

Example 140

A suspension of CrO₃ (294 mg, 2.94 mmol) in dry CH₂Cl₂ (2 mL) was stirred vigorously for a few minutes at −20° C. under nitrogen and 3,5-dimethylpyrazole (424 mg, 4.41 mmol) was added quickly in one portion. The mixture was stirred vigorously for 15 min. A solution of Example 138 (50 mg, 0.147 mmol) in dry CH₂Cl₂ (2 mL) was added by cannula. The mixture was stirred vigorously for 2 h at −20° C. The reaction was warmed to 0° C. and 6N NaOH (1 mL) was added and the mixture was stirred at 0° C. for 1 h. The mixture was diluted with CH₂Cl₂ (20 mL) then washed with water (20 mL), 10% aqueous HCl (10 ml), water (10 mL), and brine (20 mL). The organic layer was dried (MgSO₄) and concentrated in vacuo to afford the crude product (215.1 mg). This was purified by flash chromatography (10 g Si, 25 mL/min, gradient from 0 to 30% EtOAc in hexanes over 60 min) to give Example 140 (23.6 mg, 45%) as a light yellow oil. LCMS (ES+) 355 (M+H)$^+$; $^1$H NMR (CDCl₃, 500 MHz) δ 7.51 (1H, s), 7.45 (2H, d J 8.9, 4.7 Hz), 7.36 (1H, s), 7.17 (2H, J 8.4 Hz), 4.09 (4H, m), 3.20 (1H, d, J 16.1 Hz), 2.71 (1H, ddd, J 18.4, 12.4, 7.7 Hz), 2.68 (1H, d, J 16.1 Hz), 2.61 (1H, ddd, J 18.4, 6.6, 1.7 Hz), 2.27 (1H, ddd, J 13.7, 12.4, 6.6 Hz), 1.98 (1H, ddd, J 13.7, 7.7, 1.7 Hz), 1.29 (3H, s), Step 2:

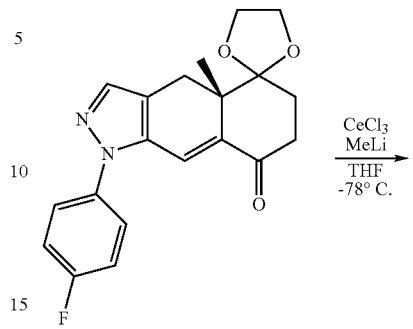

Example 140

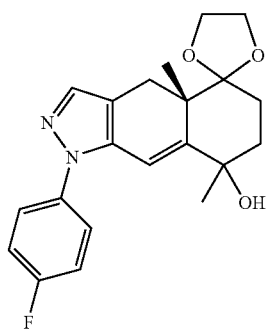

Example 141

A suspension of CeCl₃ (504 mg, 2.05 mmol) in dry THF (5 mL) was stirred vigorously for 2 h at room temperature under nitrogen until cloudy. The mixture was cooled to −78° C. and MeLi (1.27 mL of a 1.6 M solution in Et₂O, 2.05 mmol) was added. The dark orange mixture was stirred at −78° C. for 1 h. A solution of Example 140 (72.4 mg, 0.205 mmol) in dry THF (2 mL) was added by cannula and the reaction was stirred at −78° C. for 2.5 h. The reaction was quenched by the addition of saturated NH₄Cl (10 mL) and partitioned between water (100 mL) and CH₂Cl₂ (100 mL). The aqueous layer was extracted with CH₂Cl₂ (2×50 mL) and the combined organic extracts were dried (MgSO₄) and concentrated in vacuo to afford the crude Example 141 (80.6 mg). This was carried through to the next step without any further purification.

Step 3:

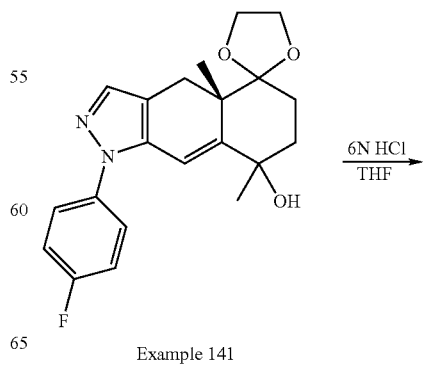

Example 141

-continued

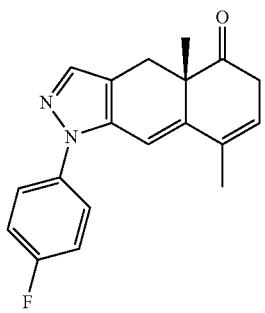

I

A solution of crude Example 141 (28.2 mg) in 6N aqueous HCl (300 µL) and THF (7 mL) was heated at 50° C. for 6 h. The reaction was diluted with EtOAc (25 mL) and 10% Na₂CO₃ (25 mL). The aqueous layer was extracted with EtOAc (2×25 mL) and the combined organic extracts were dried (MgSO₄) and concentrated in vacuo to afford the crude product. This was purified by flash chromatography (10 g Si, 25 mL/min, gradient form 0 to 30% EtOAc in hexanes over 60 min) to give ketone I (13.1 mg). LCMS (ES+) 309 (M+H)⁺; ¹H NMR (CDCl₃, 500 MHz) δ 7.52 (1H, s), 7.48 (2H, d J 8.9, 4.7 Hz), 7.18 (2H, J 8.4 Hz), 6.18 (1H, s), 5.80 (1H, br s), 3.45 (1H, br d, J 21.5 Hz), 3.05 (1H, d, J 16.3 Hz), 3.02 (1H, ddd, J 21.5, 4.9, 1.4 Hz), 2.81 (1H, d, J 16.6 Hz), 1.93 (3H, s), 1.29 (3H, s).

COMPOUND J

Step 1:

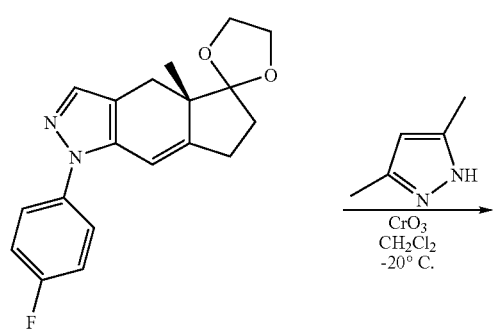

Example 142

-continued

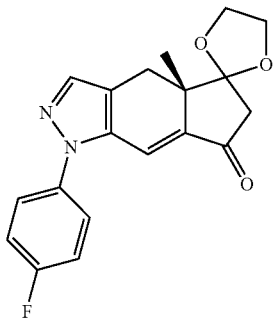

Example 143

A suspension of CrO₃ (306 mg), 3.06 mmol) in dry CH₂Cl₂ (2 mL) was stirred vigorously for 15 min at −20° C. under nitrogen and 3,5-dimethylpyrazole (442 mg, 4.60 mmol) was added quickly in one portion. The mixture was stirred vigorously for 1 h. A solution of Example 142 (50 mg, 0.153 mmol) in dry CH₂Cl₂ (2 mL) was added by cannula. The mixture was stirred vigorously for 2 h at −20° C. The reaction was warmed to 0° C. and 6N NaOH (1 mL) was added and the mixture was stirred at 0° C. for 1 h. The mixture was diluted with CH₂Cl₂ (20 mL) then washed with water (20 mL), 10% aqueous HCl (20 ml), water (20 mL), and brine (20 mL). The organic layer was dried (MgSO₄) and concentrated in vacuo to afford the crude product (191 mg). This was purified by flash chromatography (10 g Si, 25 mL/min, gradient from 0 to 30% EtOAc in hexanes over 60 min) to give Example 143 (29.8 mg, 57%) as a light yellow oil. LCMS (ES+) 341 (M+H)⁺; ¹H NMR (CDCl₃, 500 MHz) δ 7.51 (1H, s), 7.43 (2H, d J 8.9, 4.7 Hz), 7.16 (2H, J 8.4 Hz), 7.13 (1H, s), 3.99 (4H, m), 3.36 (1H, d J 16.0 Hz), 2.90 (1H, d, J 18.1 Hz), 2.62 (1H, d, J 18.1 Hz), 2.55 (1H, d, J 16.0 Hz), 1.34 (3H, s).

Step 2:

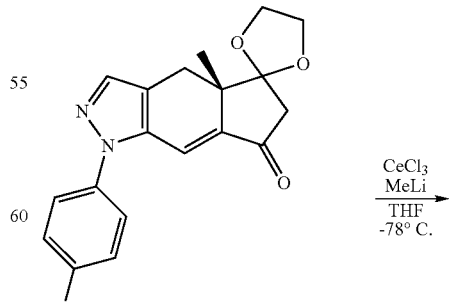

Example 143

-continued

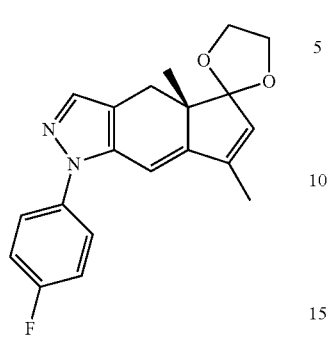

Example 144

A suspension of CeCl₃ (2.55 g, 10.36 mmol) in dry THF (25 mL) was stirred vigorously for 2 h at room temperature under nitrogen until cloudy. The mixture was cooled to −78° C. and MeLi (4.80 mL of a 1.6 M solution in Et₂O, 8.63 mmol) was added. The dark orange mixture was stirred at −78° C. for 1 h. A solution of Example 143 (293.4 mg, 0.863 mmol) in dry THF (10 mL) was added by cannula and the reaction was stirred at −78° C. for 6 h then at room temperature overnight. The reaction was quenched by the addition of saturated NH₄Cl (2 mL) and partitioned between water (100 mL) and EtOAc (100 mL). The aqueous layer was extracted with EtOAc (2×100 mL) and the combined organic extracts were dried (MgSO₄) and concentrated in vacuo to afford the crude product (370 mg). This was purified by flash chromatography (35 g Si, 40 mL/min, 0 to 30% EtOAc in hexanes over 60 min) to give Example 144 (73.9 mg, 25%,) as a pale yellow solid. LCMS (ES+) 339 (M+H)⁺; ¹H NMR (CDCl₃, 500 MHz) δ 7.47 (2H, d J 8.9, 4.7 Hz), 7.44 (1H, s), 7.14 (2H, J 8.9 Hz), 6.19 (1H, s), 5.79 (1H, s), 3.99 (4H, m), 3.08 (1H, d, J 15.4 Hz), 2.43 (1H, d, J 15.4 Hz), 1.85 (3H, br s), 1.09 (3H, s).

Step 3:

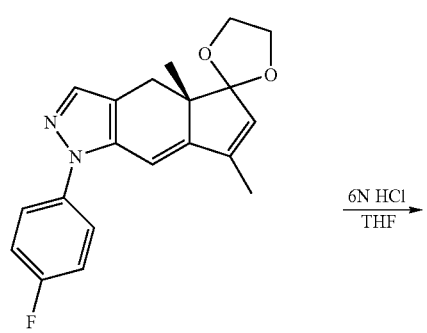

Example 144

6N HCl / THF

-continued

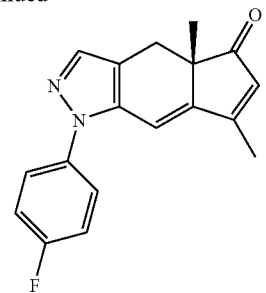

J

A solution of Example 144 (73.9 mg, 0.219 mmol) in 6N HCl (1 mL) and THF (20 mL) was heated to 55° C. for 4 h. The reaction mixture was diluted with EtOAc (40 mL) and saturated Na₂CO₃ (40 mL). The aqueous layer was extracted with EtOAc (2×25 mL). The combined organic extracts were dried (MgSO₄) and concentrated in vacuo to give the crude product. This was purified by flash chromatography (10 g Si, 25 mL/min, 0.5% MeOH in CHCl₃) to give ketone J (64.0 mg, 100%) as a pale yellow oil. LCMS (ES+) 295 (M+H)⁺; ¹H NMR (CDCl₃, 600 MHz) δ 7.56 (1H, s), 7.51 (2H, d J 8.9, 4.8 Hz), 7.20 (2H, J 8.6 Hz), 6.48 (1H, s), 6.14 (1H, s), 2.85 (1H, d, J 15.9 Hz), 2.53 (1H, d J 15.9 Hz), 2.22 (3H, br s), 1.18 (3H, s).

COMPOUND K

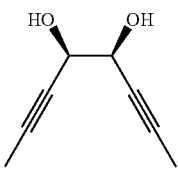

Step 1:

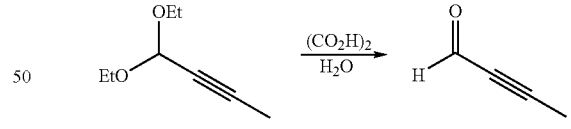

L

2-Butyn-1-al diethyl acetal (5 g, 35.2 mmol) and oxalic acid (316 mg, 3.53 mmol) were stirred as an emulsion in water (10 mL) at 75° C. for 5 h. The mixture was diluted with water (50 mL) and extracted with CH₂Cl₂ (3×100 mL). The combined organic extracts were dried (Na₂SO₄) and concentrated in vacuo to afford the crude COMPOUND L as a colorless oil. This compound was used in the next step with no further purification. ¹H NMR (CDCl₃, 500 MHz) δ 9.11 (1H, s), 2.04 (3H, s).

Step 2:

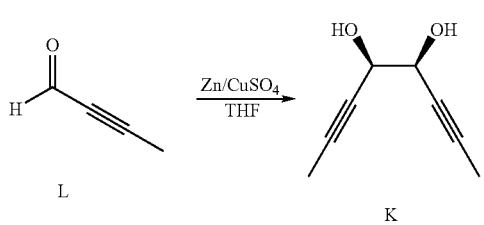

L          K

COMPOUND L above was dissolved in THF (8 mL) and added by cannula to a stirred suspension of zinc (2.34 g, 0.0352 mol) and $CuSO_4$ in TBH (2 mL) at room temperature under $-N_2$, followed by dropwise addition of AcOH. The suspension was stirred at room temperature for 3 h. The mixture was filtered to remove the zinc and $CuSO_4$ and the solid residues were washed with $Et_2O$ (3×100 mL). The filtrate was then neutralized with a solution of saturated $K_2CO_3$ (200 mL) and the organic layer was separated. The aqueous layer was extracted with $Et_2O$ (3×100 mL). The combined organic layers were dried ($MgSO_4$) and concentrated in vacuo to afford the crude product (570.5 mg). This was purified by flash chromatography (35 g Si, 40 mL/min, gradient from 20 to 50% EtOAc in hexanes over 37 min) to give diol K (245.6 mg, 10%), as a pale yellow oil. A small sample of this was recrystallized from EtOAc/hexanes to give COMPOUND H (43.7 mg) as a pale yellow solid, m.p. 106-107° C. (lit. 116° C.). $^1$H NMR ($CDCl_3$, 500 MHz) δ 4.38 (2H, s), 1.90 (6H, s).

COMPOUND M

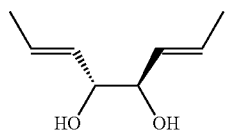

Step 1:

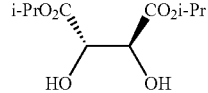

N

A solution of di-i-propyl D-tartrate (25 g, 106 mmol), 2,3-dimethoxypropane (15.6 g, 18.4 mL, 149 mmol) and p-toluenesulfonic acid (81.2 mg, 0.426 mmol) in benzene (150 mL) was heated at reflux overnight. The reaction mixture was washed with saturated $K_2CO_3$ dried ($MgSO_4$) and concentrated in vacuo to afford COMPOUND N as a colorless oil in quantitative yield. Spectroscopic data agreed with that published in the literature.

Step 2:

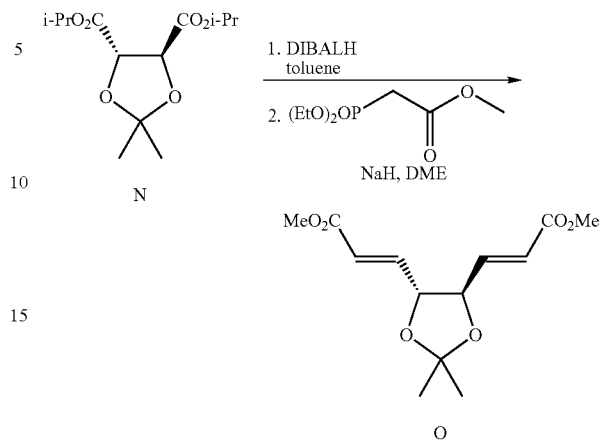

N          O

A solution of DIBALH (38.6 mL of 1 M solution in hexanes, 38.6 mmol) was added to a stirred solution of COMPOUND N (5 g, 19.3 mmol) in dry toluene (60 mL) at −78° C. under nitrogen. The mixture was stirred at −78° C. for 3 h. A solution of sodio methyl diethylphosphonoacetate (obtained by adding at 0° C., methyl diethylphosphoacetate (10.1 g, 8.85 mL, 48.2 mmol) in dry DME (20 mL) to a suspension of NaH (2.05 g, 60% dispersion in oil, 51.5 mmol) in dry DME (20 mL) and stirring the mixture for 30 min at room temperature) was added at −78° C. After 5 min the cooling bath was removed and the reaction mixture was allowed to warm to room temperature and was stirred overnight. Water (50 mL) was added and the mixture was poured into $Et_2O$ (500 mL). The organic layer was washed with water (4×50 mL), dried ($MgSO_4$) and concentrated in vacuo to afford the crude product (7.17 g). This was purified by flash chromatography (110 g Si, 70 mL/min, 100% hexanes for 5 min, gradient to 10% EtOAc in hexanes over 20 min, isocratic at 10% EtOAc in hexanes for 40 min) to give COMPOUND O (501.8 mg) as a colorless oil. LCMS (ES+) 293 (M+Na)$^+$; $^1$H NMR ($CDCl_3$, 500 A) δ 6.85 (2H, d, J 15.6 Hz), 6.15 (2H, d, J 15.6 Hz), 4.25 (2H, m), 3.75 (6H, s), 1.45 (6H, s).

Step 3:

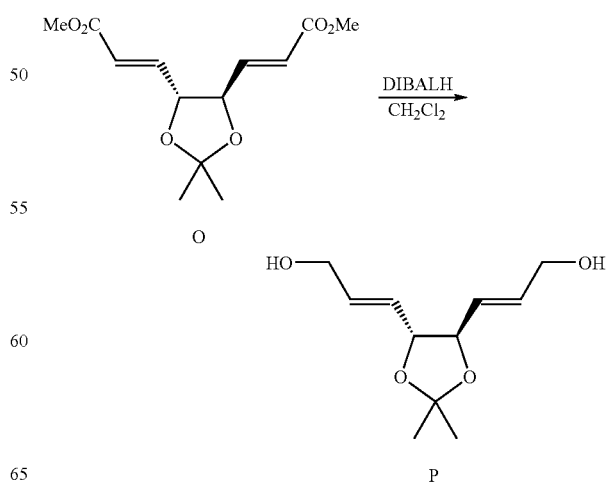

O          P

DIBALH (3.1 mL of a 1M solution in hexanes, 3.09 mmol) was added dropwise to a stirred solution of COMPOUND O in dry CH$_2$Cl$_2$ at −78° C. under nitrogen. The reaction mixture was allowed to warm slowly to 0° C. over 4 h and was quenched by the addition of saturated NH$_4$Cl (8 mL). The resulting thick slurry was filtered through Celite. The residue was triturated repeatedly with EtOAc (3×50 mL) and filtered through Celite. The combined filtrates were dried (Na$_2$SO$_4$) and concentrated in vacuo to give the crude product (170.9 mg). This was purified by flash chromatography (10 g Si, 25 mL/min, gradient from 65 to 100% EtOAc in hexanes over 30 min, then isocratic at 100% EtOAc for 7 min) to give COMPOUND P (96.3 mg, 67%) as a colorless oil. $^1$H NMR (CDCl$_3$, 500 MHz) δ 5.90 (2H, dt, J 15.5, 5.0 Hz), 5.64 (2H, br d, J 15.5 Hz), 4.09 (6H, m), 3.01 (2H, br s), 1.40 (6H, s).

Step 4:

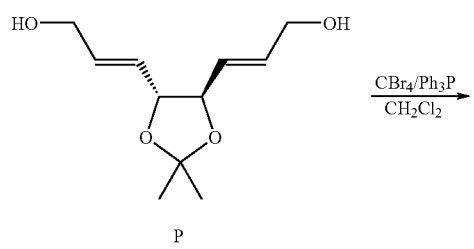

P

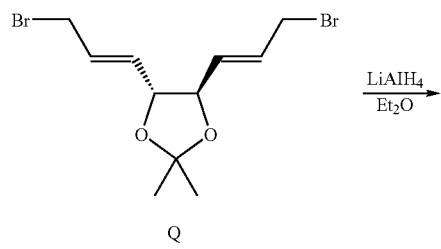

Q

CBr$_4$ (358 mg, 1.08 mmol) and Ph$_3$P (283 mg, 1.08 mmol) were added successively to a stirred solution of COMPOUND P (96.3 mg, 0.450 mmol) in dry CH$_2$Cl$_2$ (2 mL) at 0° C. The reaction was stirred at 0° C. for 1 h. After evaporation of the solvent in vacuo, the residue was purified by flash chromatography (10 g Si, 25 mL/min, isocratic at 100% hexanes for 5 min, gradient to 10% EtOAc in hexanes over 20 min, then isocratic at 10% EtOAc in hexanes for 15 min) to give COMPOUND Q (132.9 mg, 87%) as a colorless oil. $^1$H NMR (CDCl$_3$, 500 MH) δ 5.98 (2H, dt, J 15.2, 7.5 Hz), 5.70 (2H, br dd, J 15.2, 5.3 Hz), 4.07 (2H, m), 3.92 (4H, d, J 7.5 Hz), 1.40 (6H, s).

Step 5:

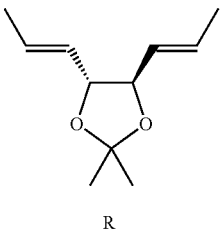

R

LiAlH$_4$ (3.82 mL of a 1 M solution in Et$_2$O, 3.82 mm6l) was added to a stirred solution of COMPOUND Q (298.3 mg, 0.877 mmol) in dry Et$_2$O (6 mL) under nitrogen and the reaction mixture was heated at reflux for 1 h. The reaction was cooled to 0° C. and saturated NH4Cl (1 mL) was added to quench the reaction. The resulting slurry was filtered through Celite and the precipitate was washed with Et$_2$O. The filtrate was washed with brine (20 mL), dried (MgSO$_4$) and concentrated in vacuo to afford COMPOUND R (125.9 mg, 79%) as a colorless oil. $^1$H NMR (CDCl$_3$, 600 MHz) δ 5.75 (2H, dq, J 15.2, 6.5 Hz), 5.38 (2H, br d, J 15.2 Hz), 3.98 (2H, dd, J 5.3, 2.1 Hz), 1.68 (6H, dd, J 6.6, 1.7 Hz), 1.37 (6H, s).

Step 6:

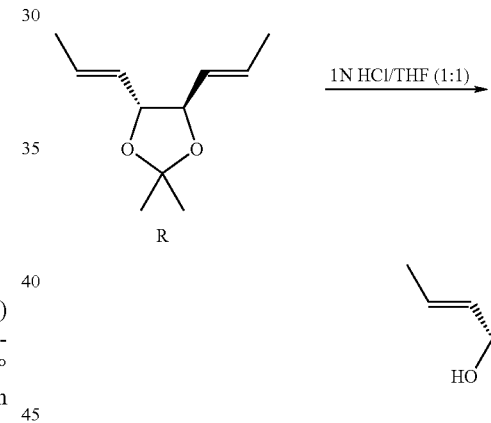

A solution of COMPOUND R (115.9 mg, 0.637 mmol) in 1N HCl/THF (1:1, 30 mL) was stirred at room temperature for 3 h. The reaction mixture was diluted with CH$_2$Cl$_2$ (50 mL) and water (50 mL). The organic layer was separated and dried (Na$_2$SO$_4$) then concentrated in vacuo to give COMPOUND M (89.5 mg, 99%) as a colorless oil. $^1$H NMR (CDCl$_3$, 500 MHz) δ 5.77 (2H, dq, J 15.4, 6.6 Hz), 5.47 (2H, br d, J 15.4 Hz), 3.91 (2H, d, J 6.0 Hz), 1.71 (6H, dd, J 6.6, 1.5 Hz).

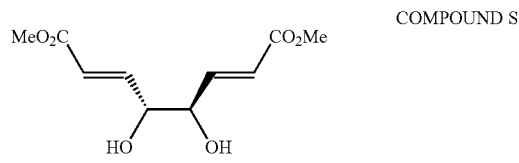

COMPOUND S

-continued

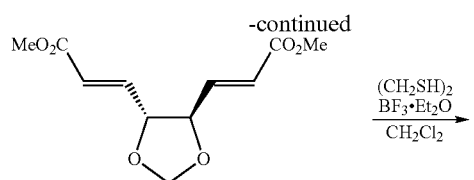

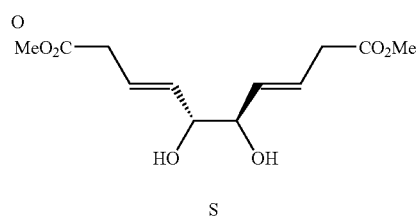

BF$_3$·Et$_2$O (52.6 mg, 47 μL, 0.370 mmol) and 1,2-ethanedithiol (41.9 mg, 37 μL, 0.444 mmol) were added successively to a stirred solution of COMPOUND N in dry CH$_2$Cl$_2$ at room temperature under nitrogen. After 30 min the reaction was quenched with saturated NaHCO$_3$ (3 mL) and stirred for a further 30 min. The organic layer was separated, and the aqueous layer was extracted with EtOAc (3×5 mL). The combined organic extracts were dried (MgSO$_4$) and concentrated in vacuo to afford COMPOUND R (46.5 mg, 85%) as a colorless solid. $^1$H NMR (CDCl$_3$, 500 MHz) δ 6.98 (2H, dd, J 15.6, 4.2 Hz), 6.10 (2H, dd, J 15.6, 1.1 Hz), 4.80 (2H, br s), 4.33 (2H, t, J 1.8 Hz), 3.72 (6H, s).

COMPOUND T

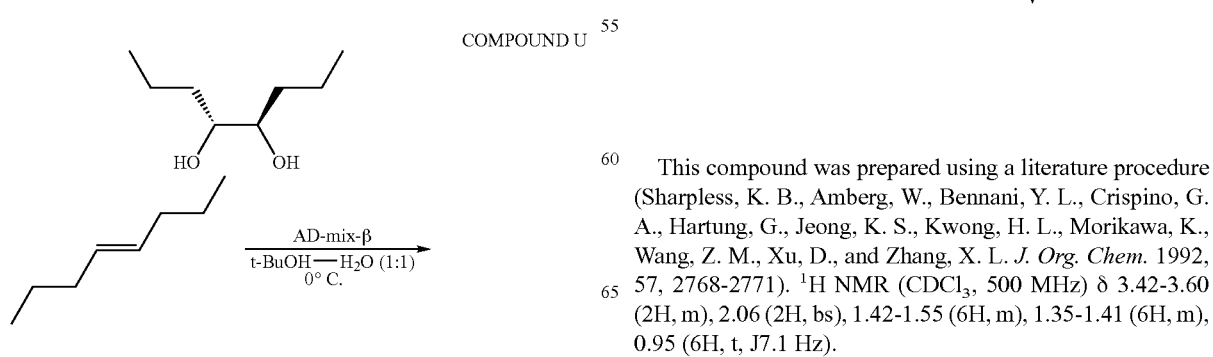

This compound was prepared using a literature procedure (Sharpless, K. B., Amberg, W., Bennani, Y. L., Crispino, G. A., Hartung, G., Jeong, K. S., Kwong, H. L., Morikawa, K., Wang, Z. M., Xu, D., and Zhang, X. L. *J. Org. Chem.* 1992, 57, 2768-2771). $^1$H NMR (CDCl$_3$, 500MHz) δ 3.37-3.41 (2H, m), 2.28 (2H, bs), 1.58-1.66 (2H, m), 1.46-1.52 (2H, m), 1.01 (6H, t, J 7.5 Hz).

COMPOUND U

-continued

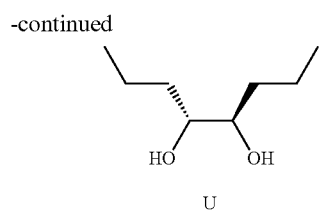

U

This compound was prepared using a literature procedure (Sharpless, K. B., Amberg, W., Bennani, Y. L., Crispino, G. A., Hartung, G., Jeong, K. S., Kwong, H. L., Morikawa, K., Wang, Z. M., Xu, D., and Zhang, X. L. *J. Org. Chem.* 1992, 57, 2768-2771). $^1$H NMR (CDCl$_3$, 500MHz) δ 3.40-3.70 (2H, m), 2.03 (2H, bs), 1.50-1.58 (4H, m), 1.38-1.48 (4H, m), 0.98 (6H, t, J 6.9 Hz).

COMPOUND V

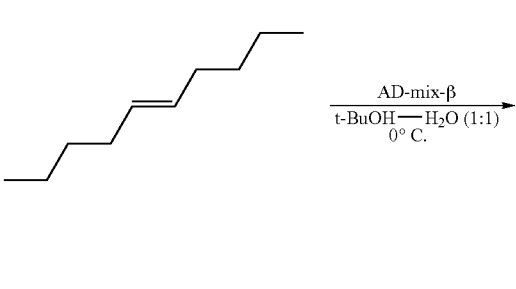

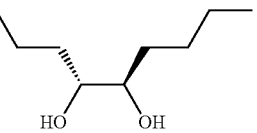

V

This compound was prepared using a literature procedure (Sharpless, K. B., Amberg, W., Bennani, Y. L., Crispino, G. A., Hartung, G., Jeong, K. S., Kwong, H. L., Morikawa, K., Wang, Z. M., Xu, D., and Zhang, X. L. *J. Org. Chem.* 1992, 57, 2768-2771). $^1$H NMR (CDCl$_3$, 500 MHz) δ 3.42-3.60 (2H, m), 2.06 (2H, bs), 1.42-1.55 (6H, m), 1.35-1.41 (6H, m), 0.95 (6H, t, J7.1 Hz).

EXAMPLES

Example 145

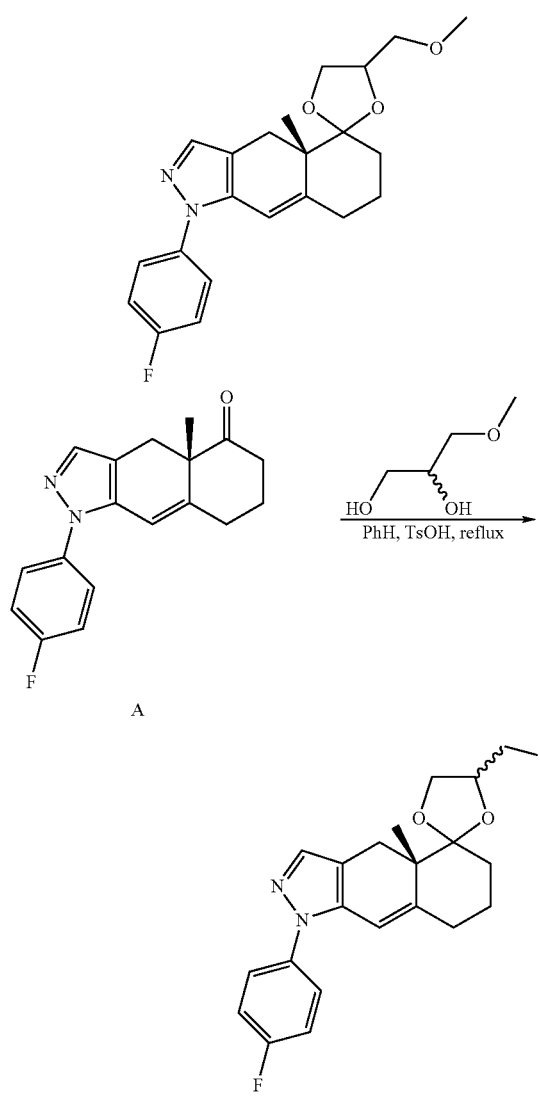

Example 145

A solution of COMPOUND A (25.1 mg, 0.0847 mmol) and 3-methoxy-1,2-propanediol (89.9 mg, 80.7 μL, 0.847 mmol) in benzene (25 mL) was heated at reflux with a Dean Stark apparatus attached and ~5 mL of solvent was distilled over to azeotrope water from the reaction. The reaction was removed from reflux and p-toluenesulfonic acid monohydrate (4.8 mg, 0.0245 mmol) was added. The reaction was heated at reflux for 5 h. The solution was cooled and diluted with EtOAc (20 mL). The mixture was washed with saturated NaHCO$_3$ (20 mL), water (20 mL) and brine (20 mL), dried (MgSO$_4$), then concentrated in vacuo to give the crude product. This was purified by flash chromatography (4 g Si, 10 mL/min, gradient from 0 to 20% EtOAc in hexanes over 40 min) to give Example 145 as a mixture of four diastereoisomers. The diastereoisomers were separated by chiral HPLC (AD, 20×250 mm, 9 mL/min, isocratic at 1.5% EtOH in heptane) to give four diastereoisomers (Examples 146, 147, 148 and 149, 6.3, 3.7, 5.3, 5.9 mg in order of elution, overall yield 65%) as colorless oils. Major diastereoisomer: LCMS (ES+) 385 (M+H)$^+$; $^1$H NMR (CDCl$_3$, 500 MHz) δ 7.44 (2H, dd, J 8.9, 4.9 Hz) 7.42 (1H, s), 7.14 (2H, t, J 8.6 Hz), 6.17 (1H, br d, J 2.2 Hz), 4.36 (1H, br quintet, J 6.3 Hz), 4.13 (1H, t J 7.4 Hz), 3.67 (1H, t, J 7.5 Hz), 3.60 (1H, dd, J 9.8, 5.5 Hz), 3.48 (1H, dd, J 9.8, 5.5 Hz), 3.37 (3H, s), 3.30 (1H, d, J 16.0 Hz), 2.47 (1H, d, J 15.8 Hz), 2.42 (1H, m), 2.27 (1H, br d, J 15.4 Hz), 1.85 (1H, m), 1.79 (1H, m), 1.70 (1H, m), 1.60 (1H, m), 1.19 (3H, s).

Example 150

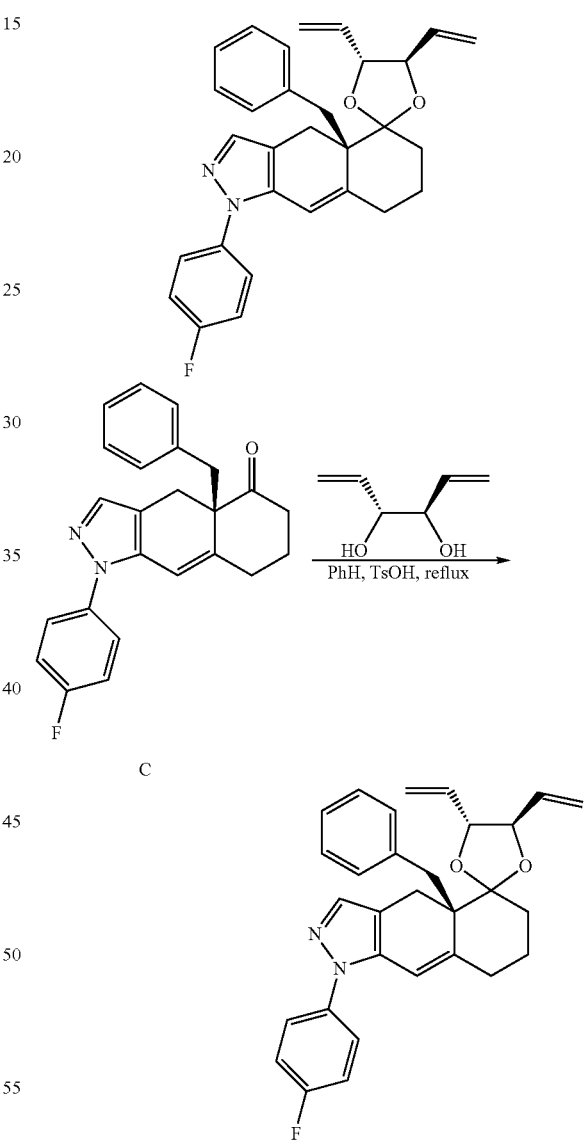

Example 150

A solution of COMPOUND C (20.9 mg, 0.0562 mmol) and (3R,4R)-1,5-hexadien-3,4-diol (64.1 mg, 0.562 mmol) in benzene (25 mL) was heated at reflux with a Dean Stark apparatus attached and ~5 mL of solvent was distilled over to azeotrope water from the reaction. The reaction was removed from reflux and p-toluenesulfonic acid monohydrate (3.2 mg, 0.0169 mmol) was added. The reaction was heated at reflux overnight. The solution was cooled and diluted with EtOAc (20 mL). The mixture was washed with saturated NaHCO$_3$ (20 mL), water (20 mL) and brine (20 mL), dried (MgSO$_4$), then concentrated in vacuo to give the crude product. This was purified by flash chromatography (10 g Si, 25 mL/min, gradient from 0 to 20% EtOAc in hexanes over 40 min) to give Example 150 (11.9 mg, 45%) as a colorless oil. LCMS (ES+) 469 (M+H)$^+$; $^1$H NMR (CDCl$_3$, 500 MHz) δ 7.14-7.06 (6H, br m), 7.01-6.97 (4H, br m), 6.13 (1H, d, J 2.1 Hz), 5.94 (1H, ddd, J 17.2, 10.4, 6.7 Hz), 5.81 (1H, ddd, J 17.2, 10.4, 6.7 Hz), 5.45 (1H, d, J 17.2 Hz), 5.36 (1H, d, J 10.4 Hz), 5.34 (1H, d, J 17.2 Hz), 5.22 (1H, d, J 10.4 Hz), 4.29 (1H, t, J 7.6 Hz), 4.18 (1H, t, J 7.4 Hz), 3.25 (1H, d, J 16.3 Hz), 3.05 (1H, d, J 13.1 Hz), 2.89 (1H, d, J 13.1 Hz), 2.88 (1H, d, J 16.3 Hz), 2.71 (1H, m), 2.38 (1H, d, J 14.8 Hz), 2.08 (1H, m), 1.93 (1H, m), 1.86 (2H, m).

EXAMPLES

The following compounds are synthesized from either compound A, B, C, I, or J in racemic or enantiopure form and commercially available diols or dithiols, or diols whose syntheses are described above, using procedures analogous to that described for Example 145:

| Example | Molecular structure | LCMS (M + 1)$^+$ |
|---|---|---|
| 151 | racemic | 341 |
| 152 | single diastereoisomer | 369 |
| 153 | mixture of diastereoisomers | 369 |

-continued
| Example | Molecular structure | LCMS (M + 1)+ |
|---|---|---|
| 154 | 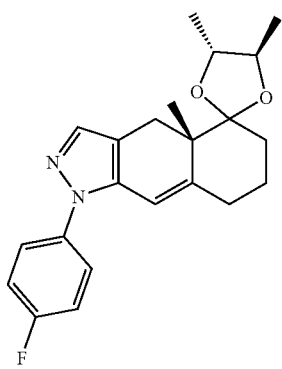 | 369 |
| 155 | 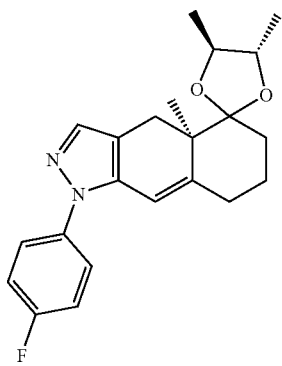 | 369 |
| 156 | 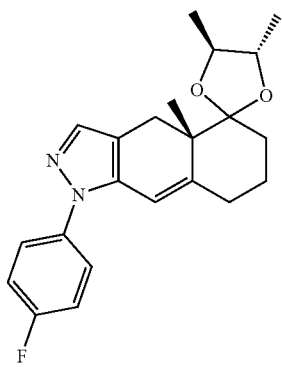 | 369 |
| 157 | 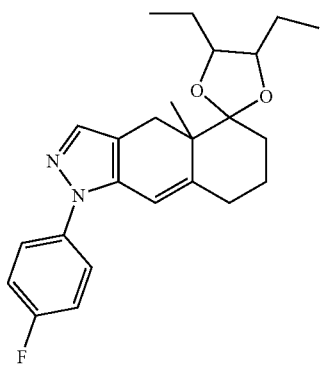 | 397 |
mixture of diastereoisomers

| Example | Molecular structure | LCMS (M + 1)+ |
|---|---|---|
| 158 | 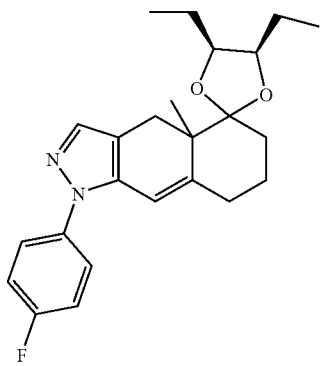<br>mixture of diastereoisomers | 397 |
| 159 | 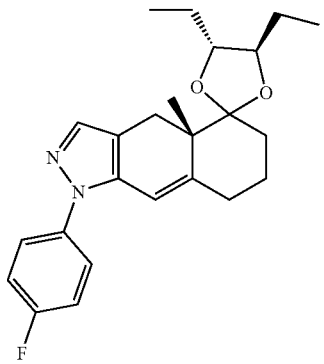 | 397 |
| 160 | 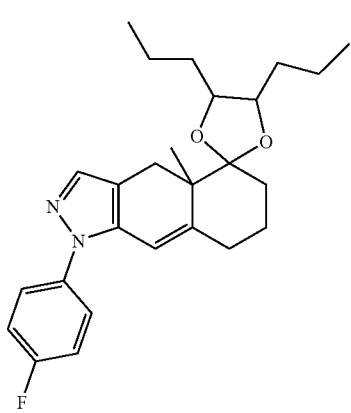<br>mixture of diastereoisomers | 425 |

-continued
| Example | Molecular structure | LCMS (M + 1)+ |
|---|---|---|
| 161 | 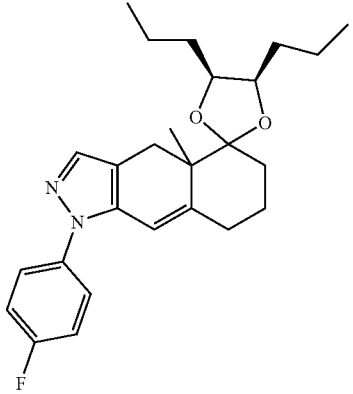 mixture of diastereoisomers | 425 |
| 162 | 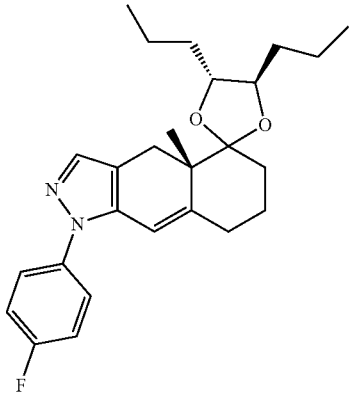 | 425 |
| 163 | 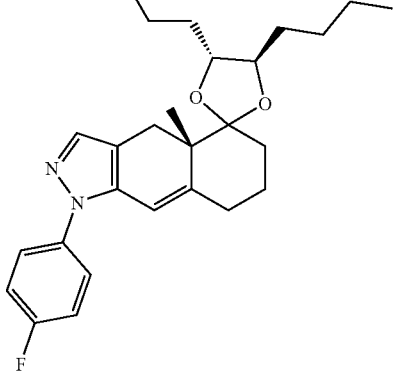 | 453 |

-continued
| Example | Molecular structure | LCMS (M + 1)+ |
|---|---|---|
| 164 | 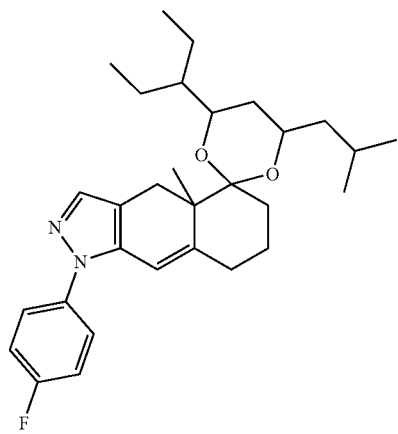 mixture of diastereoisomers | 481 |
| 165 | 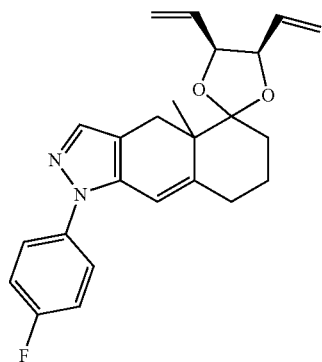 mixture of diastereoisomers | 393 |
| 166 | 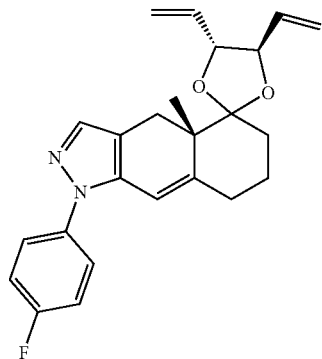 | 393 |

-continued
| Example | Molecular structure | LCMS (M + 1)+ |
|---|---|---|
| 167 | 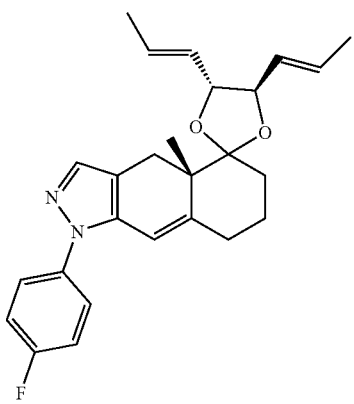 | 421 |
| 168 | 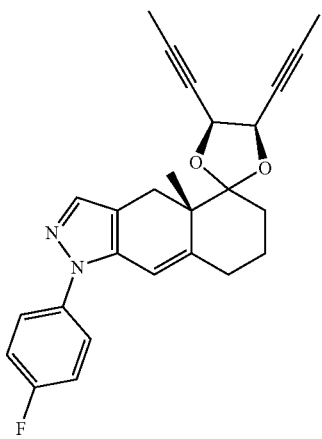<br>single diastereoisomer | 417 |
| 169 | 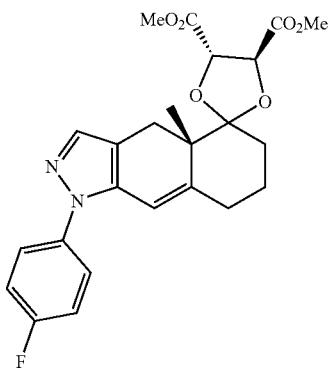 | 457 |

-continued
| Example | Molecular structure | LCMS (M + 1)+ |
|---|---|---|
| 170 | 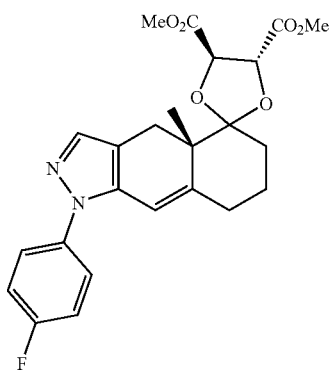 | 457 |
| 171 | 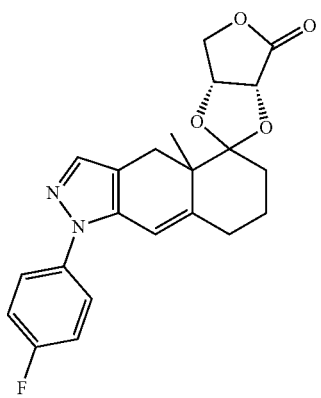 mixture of diastereoisomers | 397 |
| 172 | 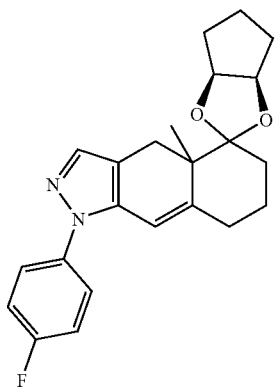 mixture of diastereoisomers | 381 |

| Example | Molecular structure | LCMS (M + 1)+ |
|---|---|---|
| 173 | 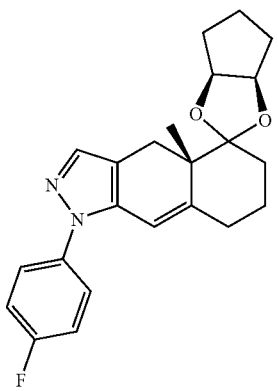 mixture of diastereoisomers | 381 |
| 174 | 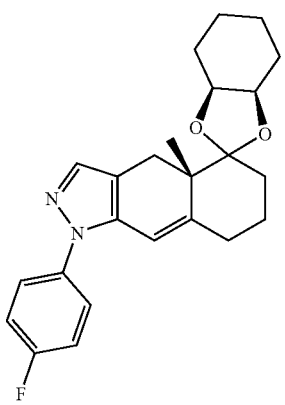 mixture of diastereoisomers | 395 |
| 175 | 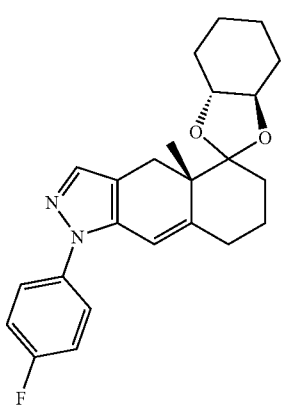 | 395 |

-continued
| Example | Molecular structure | LCMS (M + 1)+ |
|---|---|---|
| 176 | 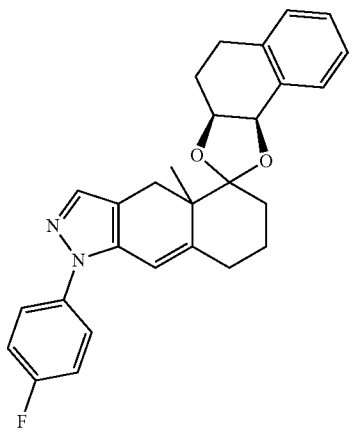 mixture of diastereoisomers | 443 |
| 177 | 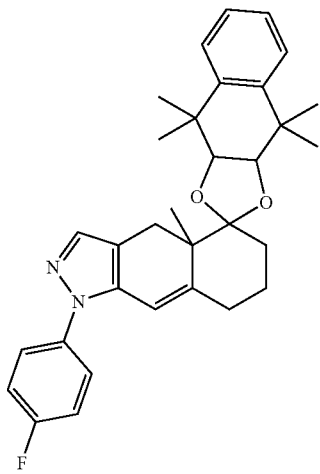 mixture of diastereoisomers | 499 |
| 178 | 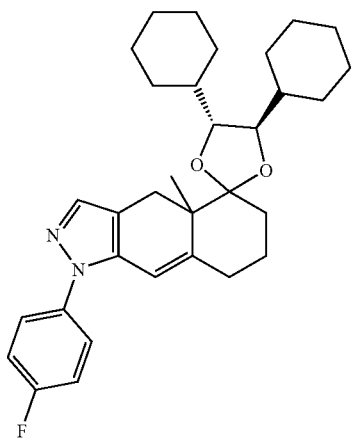 mixture of diastereoisomers | 505 |

| Example | Molecular structure | LCMS (M + 1)+ |
|---|---|---|
| 179 | 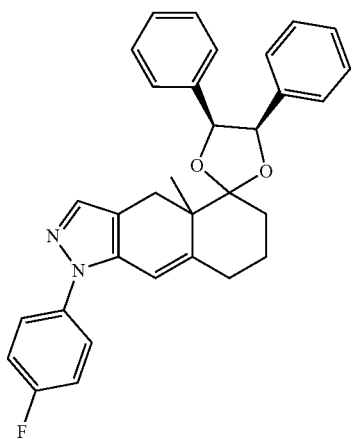 mixture of diastereoisomers | 493 |
| 180 | 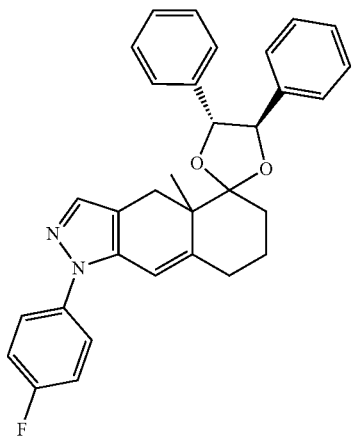 mixture of diastereoisomers | 493 |
| 181 | 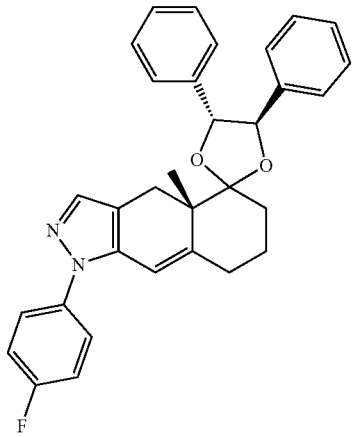 | 493 |

-continued
| Example | Molecular structure | LCMS (M + 1)+ |
|---|---|---|
| 182 | 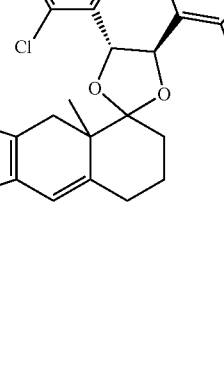 mixture of diastereoisomers | 561(m) |
| 183 | 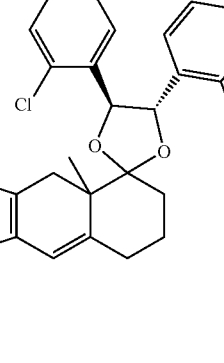 mixture of diastereoisomers | 561(m) |
| 184 | 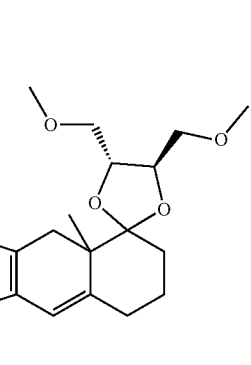 mixture of diastereoisomers | 429 |

| Example | Molecular structure | LCMS (M + 1)+ |
|---|---|---|
| 185 | 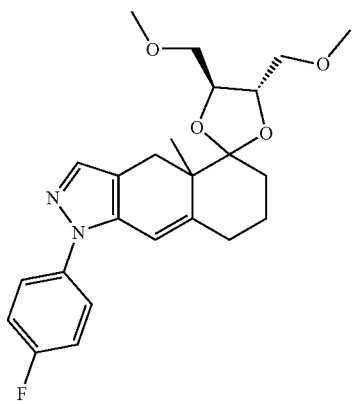 mixture of diastereoisomers | 429 |
| 186 | 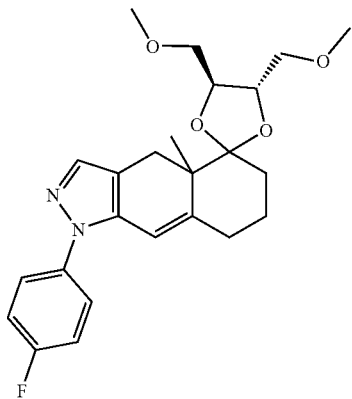 | 429 |
| 187 | 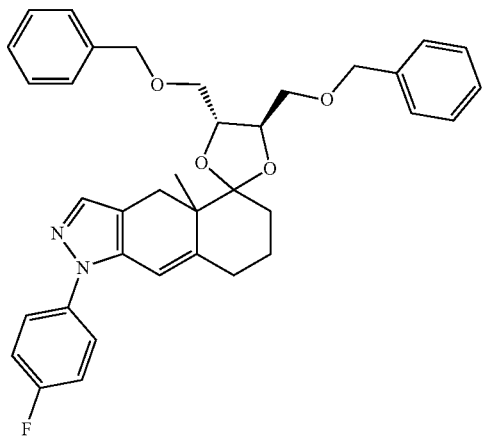 mixture of diastereoisomers | 581 |

-continued
| Example | Molecular structure | LCMS (M + 1)+ |
|---|---|---|
| 188 | 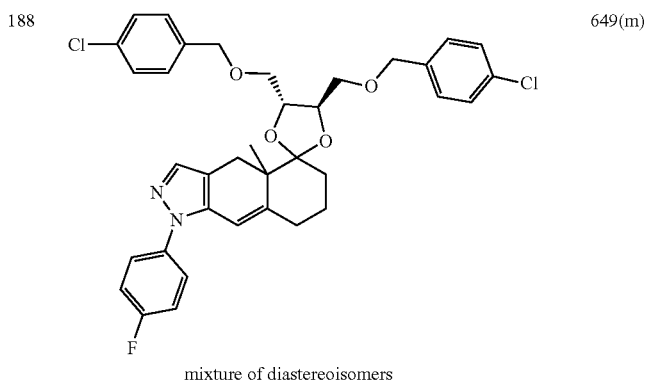  mixture of diastereoisomers | 649(m) |
| 189 | 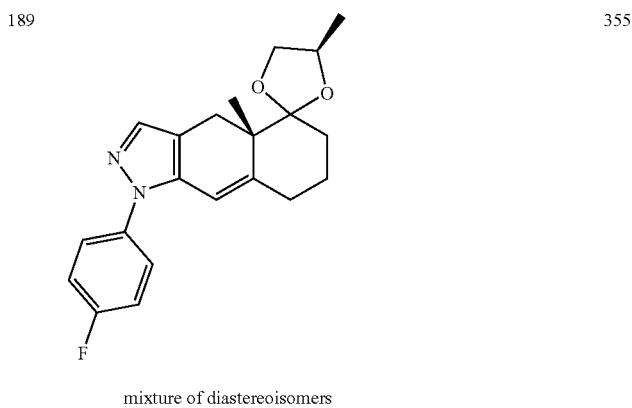  mixture of diastereoisomers | 355 |
| 190 | 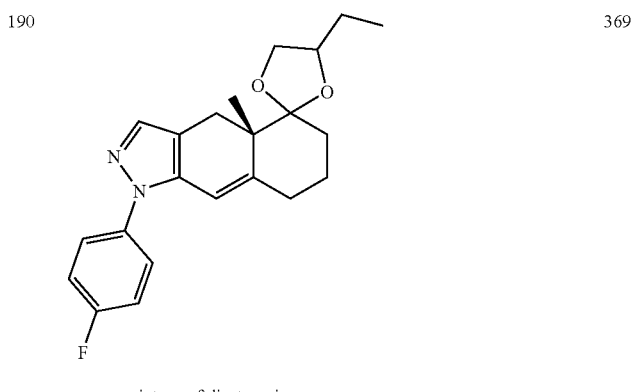  mixture of diastereoisomers | 369 |

-continued
| Example | Molecular structure | LCMS (M + 1)+ |
|---|---|---|
| 191 | 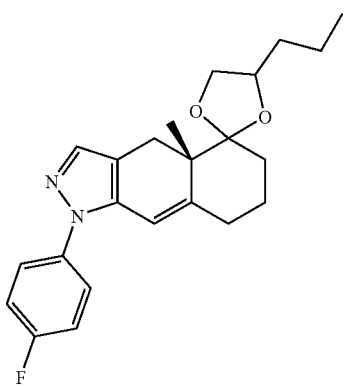 mixture of diastereoisomers | 383 |
| 192 | 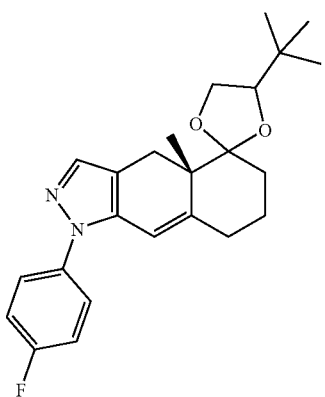 mixture of diastereoisomers | 397 |
| 193 | 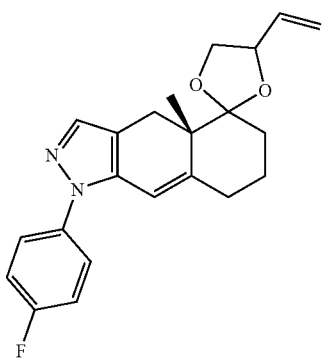 mixture of diastereoisomers | 367 |

-continued

| Example | Molecular structure | LCMS (M + 1)+ |
|---------|--------------------|--------------|
| 194 | mixture of diastereoisomers | 367 |
| 195 | 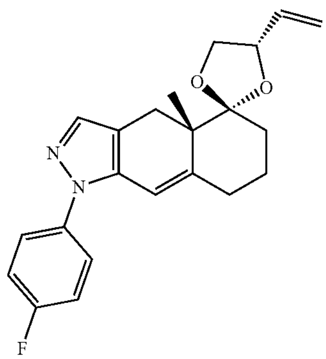 | 367 |
| 196 | 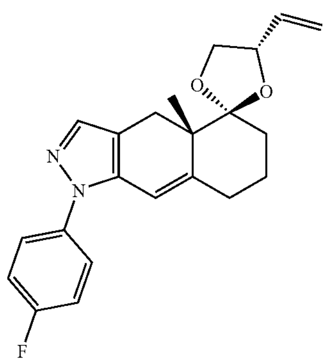 | 367 |
| 197 | mixture of diastereoisomers | 423 |

-continued
| Example | Molecular structure | LCMS (M + 1)+ |
|---|---|---|
| 198 | 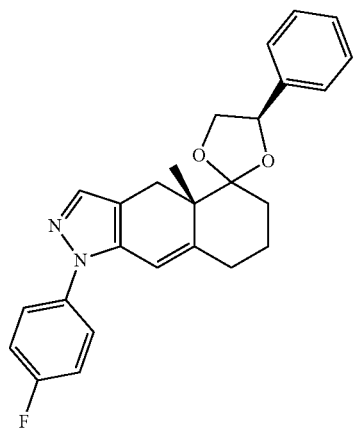<br>diastereoisomer A | 417 |
| 199 | 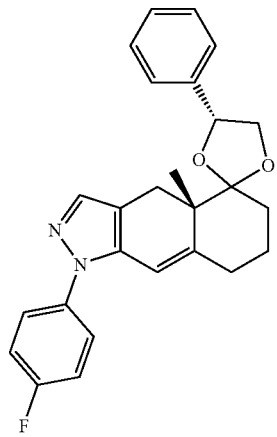<br>diastereoisomer B | 417 |
| 200 | 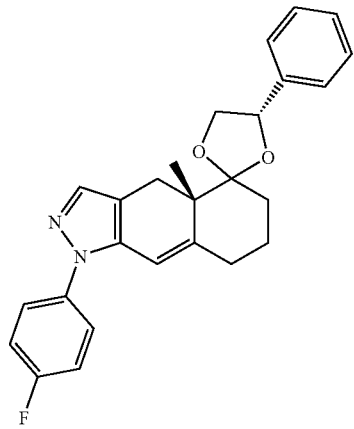<br>diastereoisomer C | 417 |

| Example | Molecular structure | LCMS (M + 1)+ |
|---|---|---|
| 201 | 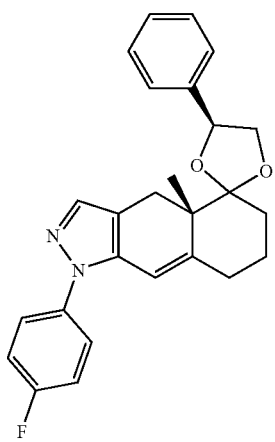<br>diastereoisomer D | 417 |
| 202 | 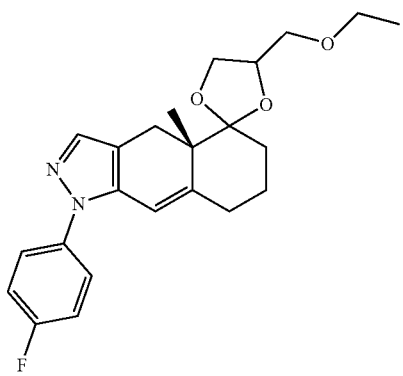<br>diastereoisomer A | 399 |
| 203 | 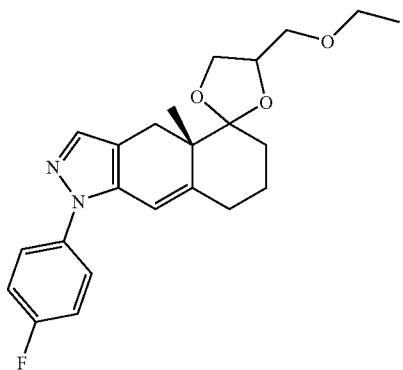<br>diastereoisomer B and C | 399 |

| Example | Molecular structure | LCMS (M + 1)+ |
|---|---|---|
| 204 | 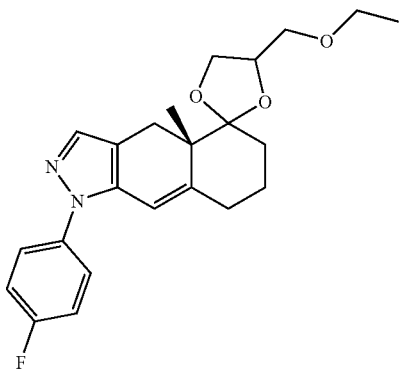 diastereoisomer D | 399 |
| 205 | 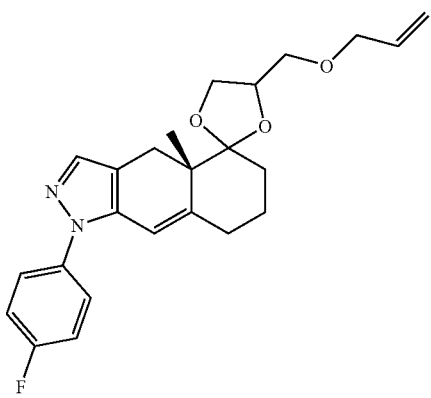 mixture of diastereoisomers | 411 |
| 206 | 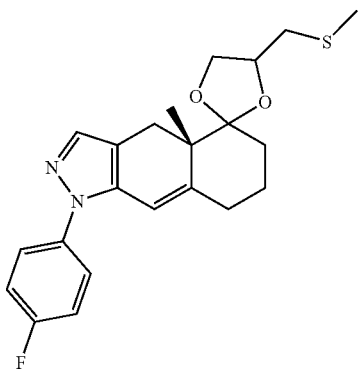 mixture of diastereoisomers | 401 |

-continued
| Example | Molecular structure | LCMS (M + 1)+ |
|---|---|---|
| 207 | 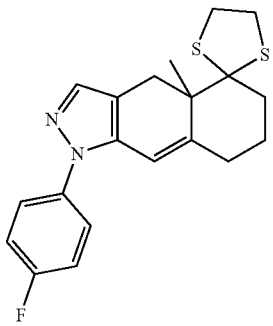 racemic | 373 |
| 208 | 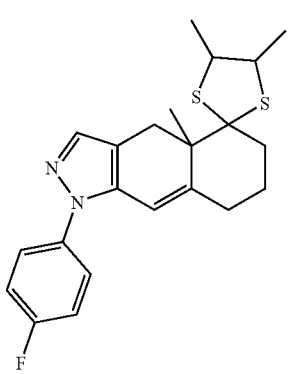 mixture of diastereoisomers | 401 |
| 209 | 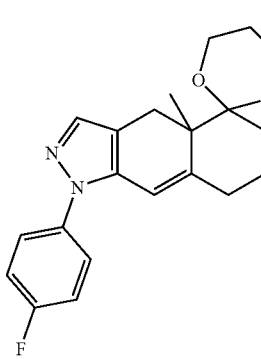 racemic | 355 |
| 210 | 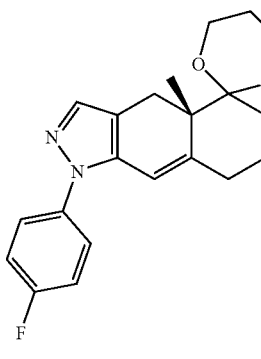 | 355 |

-continued
| Example | Molecular structure | LCMS (M + 1)+ |
|---|---|---|
| 211 | 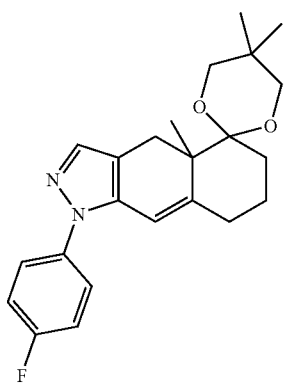 racemic | 383 |
| 212 | 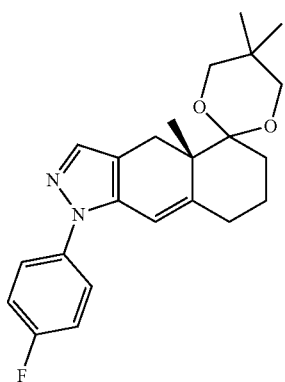 | 383 |
| 213 | 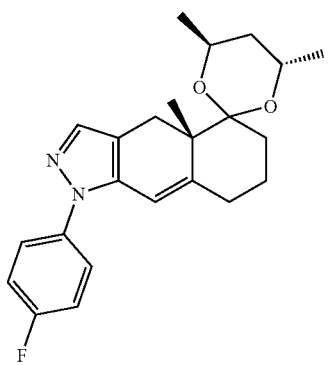 | 383 |
| 214 | 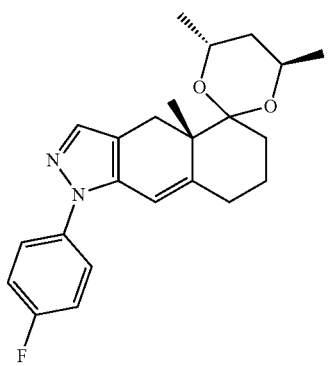 | 383 |

| Example | Molecular structure | LCMS (M + 1)+ |
|---|---|---|
| 215 | 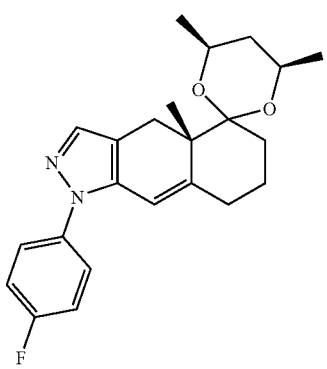 mixture of diastereoisomers | 383 |
| 216 | 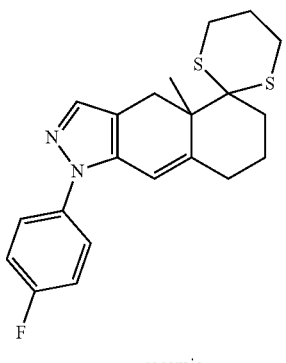 racemic | 387 |
| 217 | 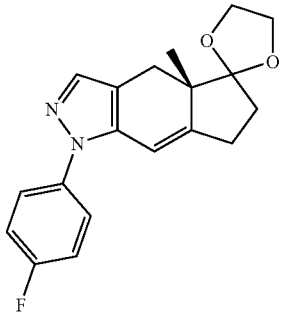 | 327 |
| 218 | 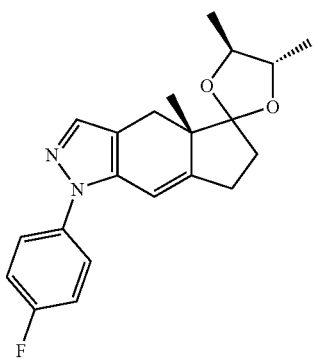 | 355 |

-continued
| Example | Molecular structure | LCMS (M + 1)+ |
|---------|---------------------|---------------|
| 219 | 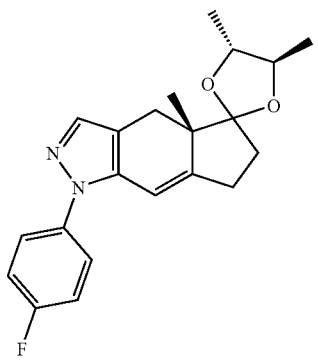 | 355 |
| 220 | 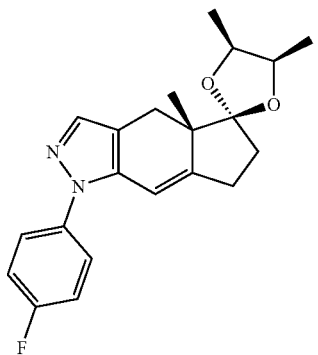 | 355 |
| 221 | 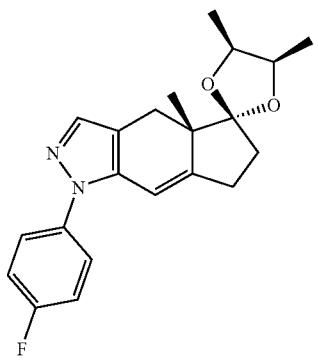 | 355 |
| 222 | 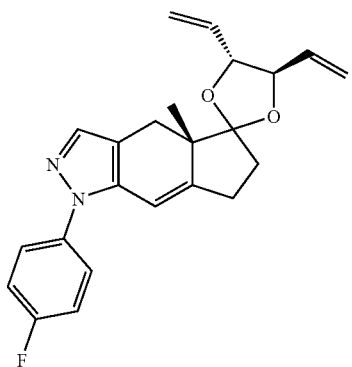 | 379 |

| Example | Molecular structure | LCMS (M + 1)+ |
|---|---|---|
| 223 | 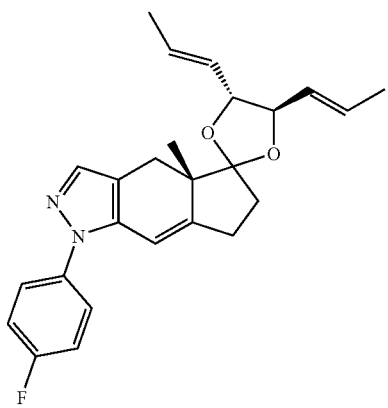 | 407 |
| 224 | 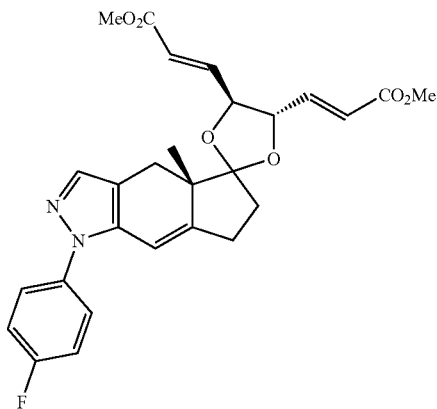 | 495 |
| 225 | 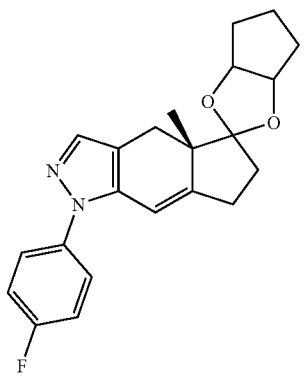<br>mixture of diastereoisomers | 367 |

| Example | Molecular structure | LCMS (M + 1)+ |
|---|---|---|
| 226 | 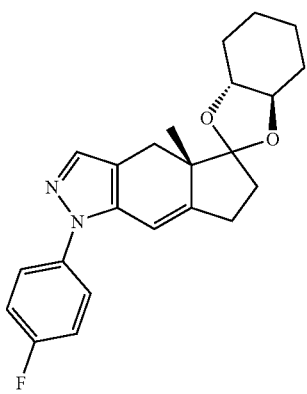 | 381 |
| 227 | 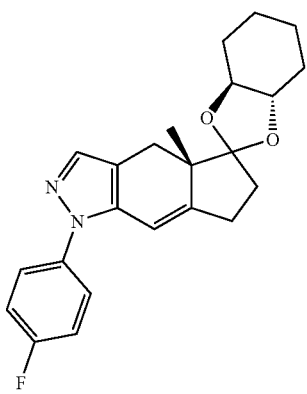 | 381 |
| 228 | 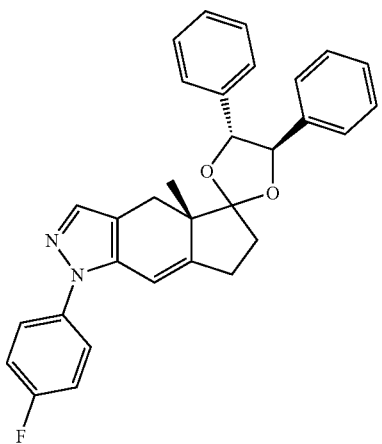 | 479 |

| Example | Molecular structure | LCMS (M + 1)+ |
|---|---|---|
| 229 | 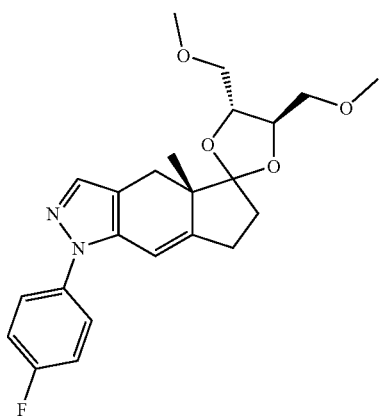 | 415 |
| 230 | 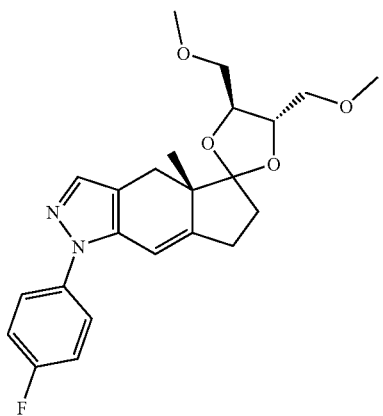 | 415 |
| 231 | 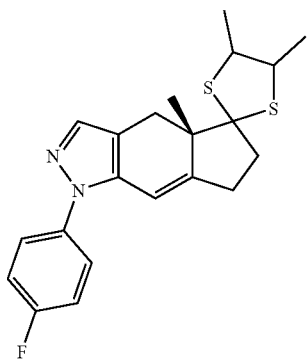 mixture of four diastereoisomers | 387 |

| Example | Molecular structure | LCMS (M + 1)+ |
|---|---|---|
| 232 | 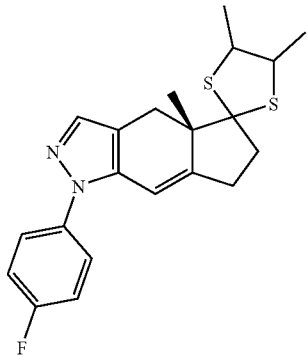 mixture of two diastereoisomers | 387 |
| 233 | 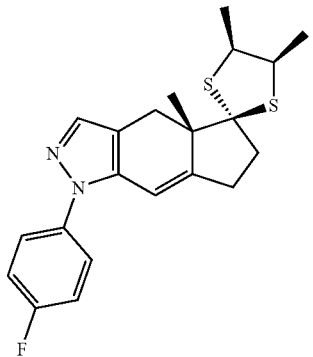 single diastereoisomer | 387 |
| 234 | 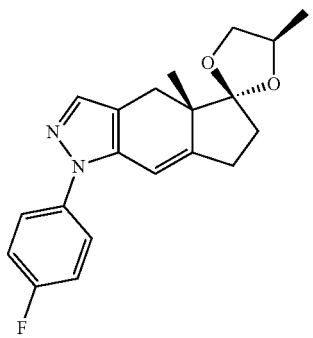 | 341 |
| 235 | 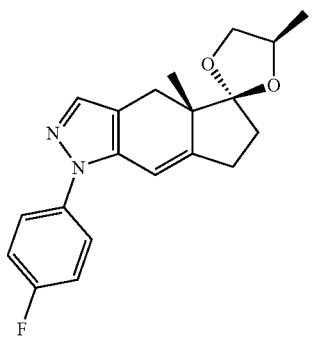 | 341 |

-continued

| Example | Molecular structure | LCMS (M + 1)+ |
|---------|---------------------|---------------|
| 236 | 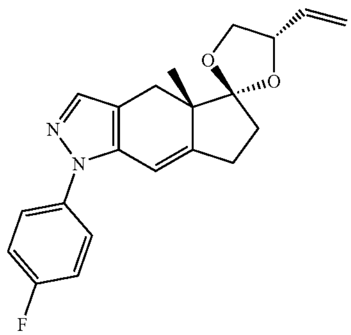 | 353 |
| 237 | 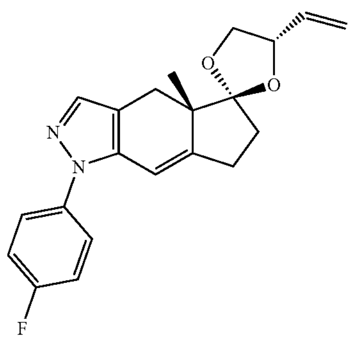 | 353 |
| 238 | 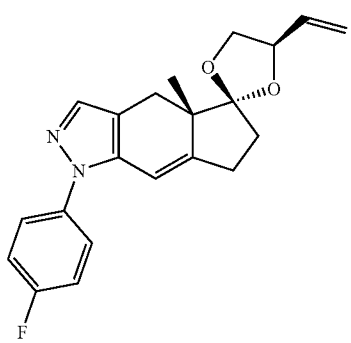 | 353 |
| 239 | 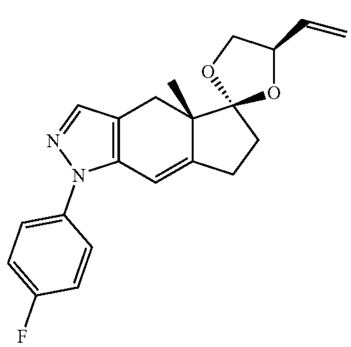 | 353 |

-continued
| Example | Molecular structure | LCMS (M + 1)+ |
|---|---|---|
| 240 | 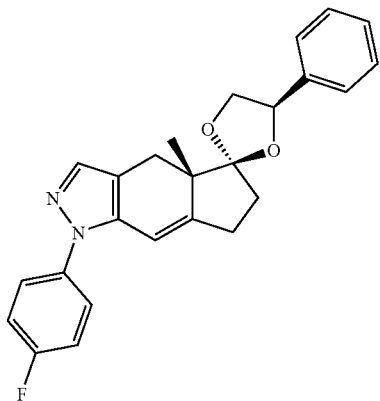 | 403 |
| 241 | 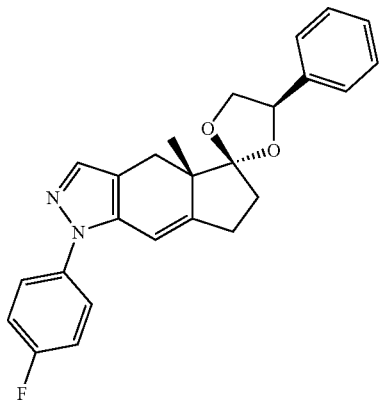 | 403 |
| 242 | 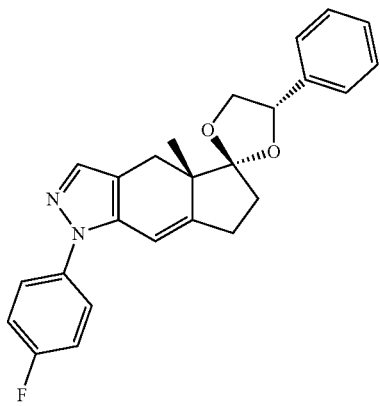 | 403 |

| Example | Molecular structure | LCMS (M + 1)+ |
|---|---|---|
| 243 | 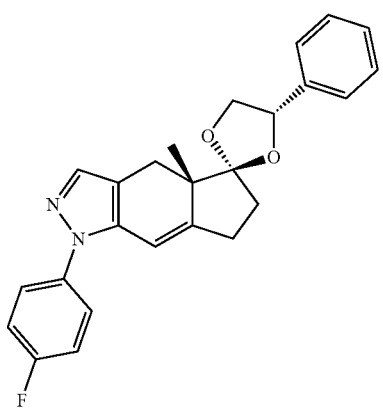 | 403 |
| 244 | 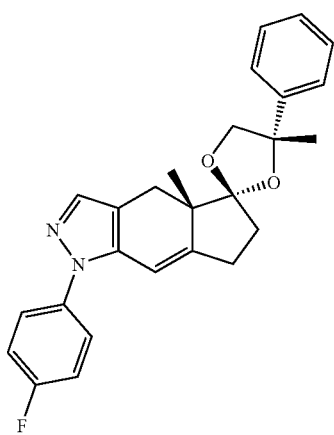 | 417 |
| 245 | 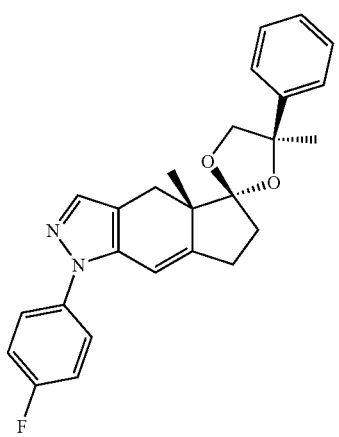 | 417 |

-continued
| Example | Molecular structure | LCMS (M + 1)+ |
|---|---|---|
| 246 | 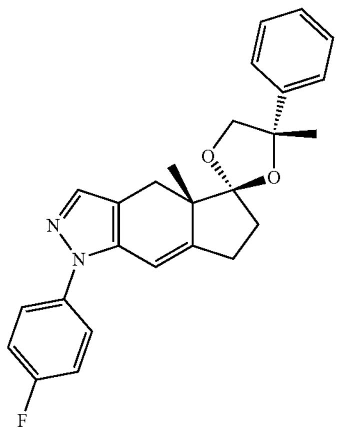 | 417 |
| 247 | 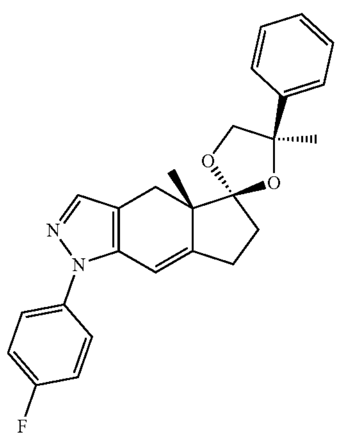 | 417 |
| 248 | 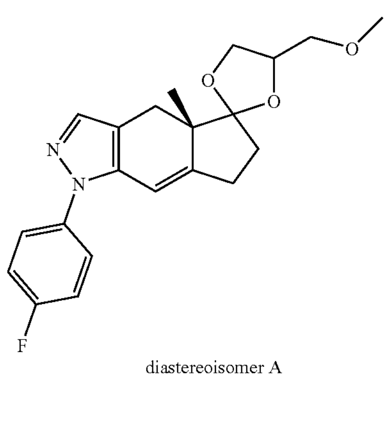 | 371 |
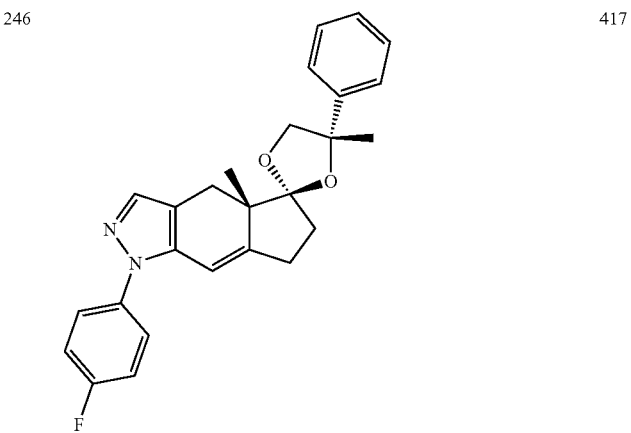
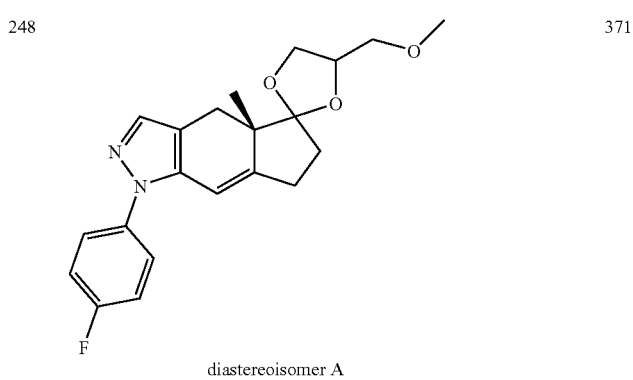
diastereoisomer A

| Example | Molecular structure | LCMS (M + 1)+ |
|---|---|---|
| 249 | 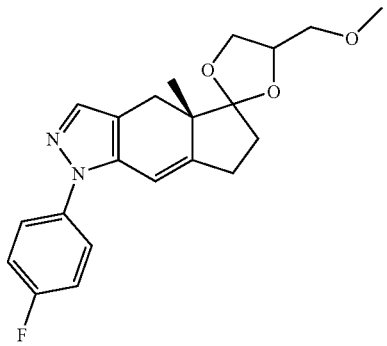<br>diastereoisomer B | 371 |
| 250 | 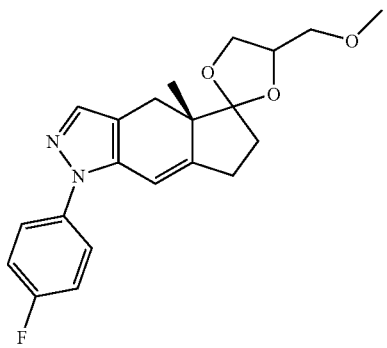<br>diastereoisomer C | 371 |
| 251 | 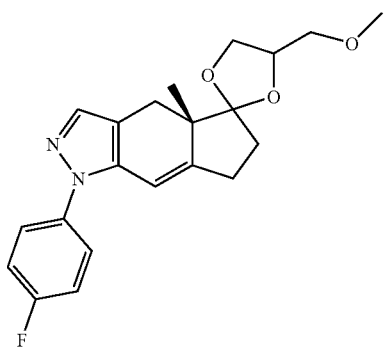<br>diastereoisomer D | 371 |
| 252 | 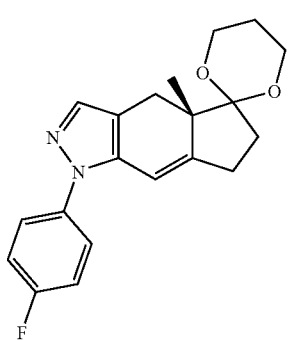 | 341 |

-continued
| Example | Molecular structure | LCMS (M + 1)+ |
|---|---|---|
| 253 | 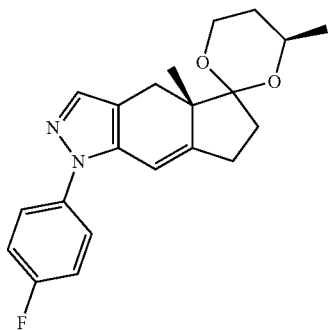<br>single diastereoisomer | 355 |
| 254 | 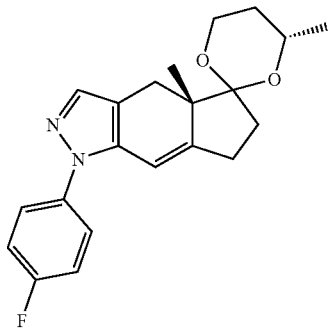<br>single diastereoisomer | 355 |
| 255 | 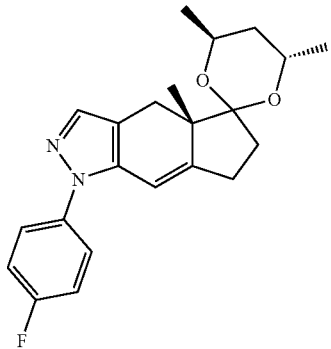 | 369 |
| 256 | 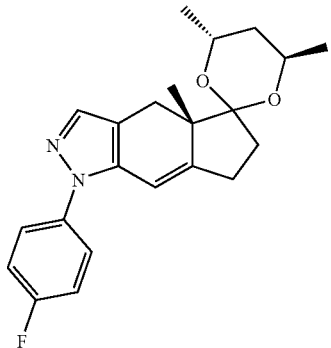 | 369 |

-continued
| Example | Molecular structure | LCMS (M + 1)+ |
|---|---|---|
| 257 | 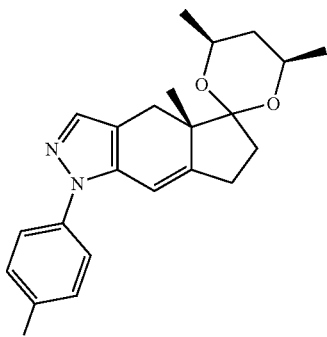 single diastereoisomer | 369 |
| 258 | 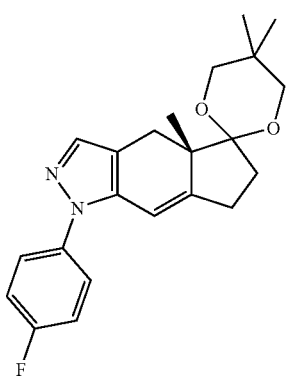 | 369 |
| 259 | 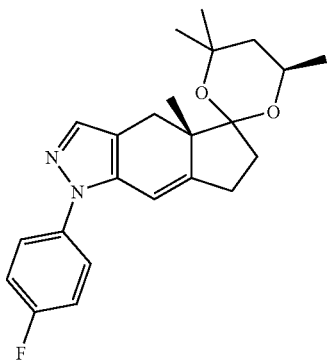 diastereoisomer A | 383 |
| 260 | 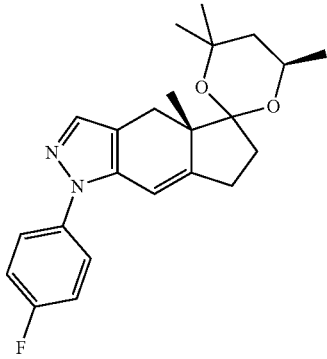 diastereoisomer B | 383 |

| Example | Molecular structure | LCMS (M + 1)+ |
|---|---|---|
| 261 | 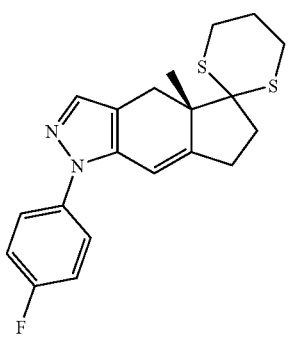 | 373 |
| 262 | 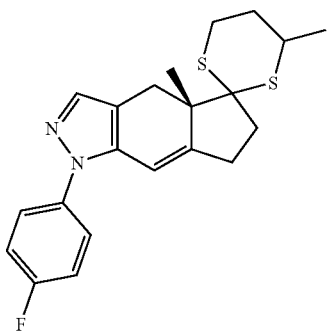 diastereoisomer A | 387 |
| 263 | 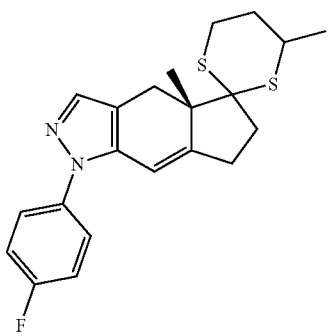 diastereoisomer B | 387 |
| 264 | 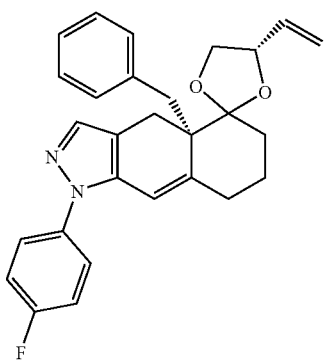 mixture of diastereoisomers | 443 |

-continued

| Example | Molecular structure | LCMS (M + 1)+ |
|---|---|---|
| 265 | diastereoisomer A | 443 |
| 266 | diastereoisomer B | 443 |
| 267 | 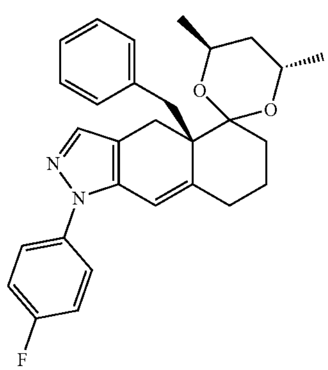 | 459 |
| 268 | 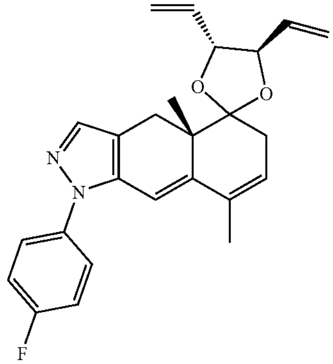 | 405 |

-continued

| Example | Molecular structure | LCMS (M + 1)+ |
|---|---|---|
| 269 | 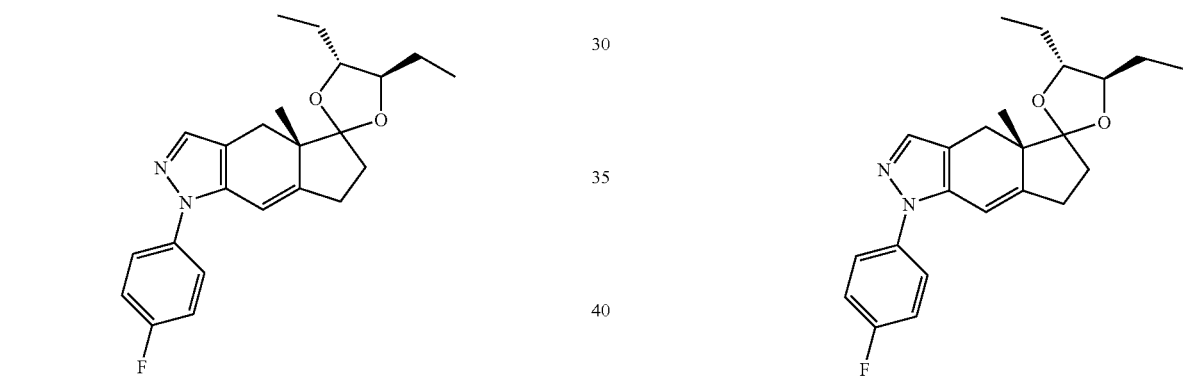 | 505 |

Example 270

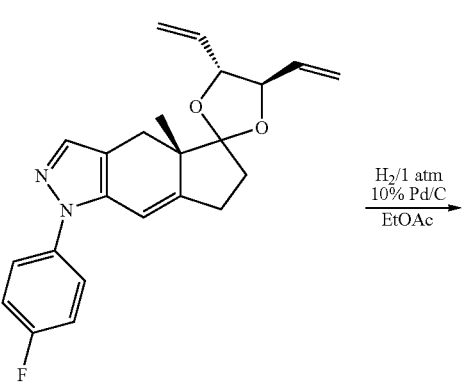

Example 222

A suspension of 10% Pd/C (3.0 mg) in a solution of Example 222 (30.6 mg, 0.0809 mmol) in EtOAc (10mL) was stirred under 1 atm $H_2$ for 30 min. The reaction mixture was filtered through Celite and concentrated in vacuo to afford Example 270 (29.5 mg, 95%) as a colorless oil. LCMS (ES+) 383 (M+H)+; $^1$H NMR (CDCl$_3$, 500 MHz) δ 7.45 (2H, dd, J 8.9, 4.7 Hz), 7.42 (1H, s), 7.14 (2H, t J 8.4 Hz), 6.16 (1, br t, J2.0 Hz), 3.67 (1H, dt, J 7.6, 4.3 Hz), 3.54 (1H, dt, J 7.1, 4.8 Hz), 3.00 (1H, d, J 15.2 Hz), 2.54 (2H, m), 2.37 (1H, d, J 15.2 Hz), 2.20 (1H, dt, J 12.8, 10.5 Hz), 1.96 (1H, ddd, J 12.9, 8.3, 2.8 Hz), 1.61 (4H, m), 1.14 (3H, s), 1.04 (3H, t J 7.6 Hz), 0.97 (3H, t, J 7.6 Hz).

Example 271

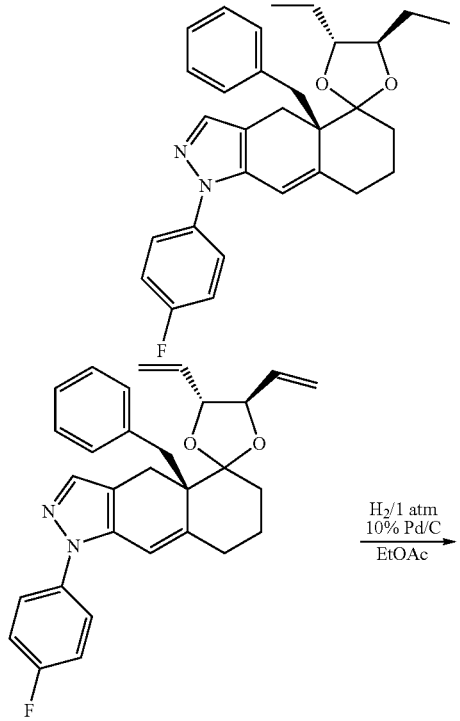

Example 150

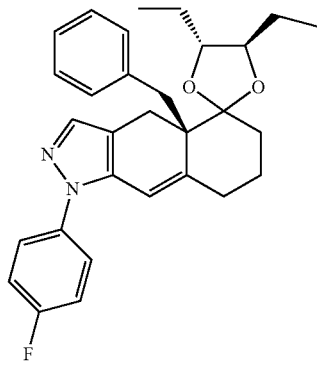

Example 271

A suspension of 10% Pd/C (3.0 mg) in a solution of Example 150 (31.8 mg, 0.0679 mmol) in EtOAc (10 mL) was stirred under 1 atm H₂ for 2 h. The reaction mixture was filtered through Celite and concentrated in vacuo to afford Example 271 (32.0 mg, quantitative) as a colorless oil. LCMS (ES+) 473 (M+H)$^+$; $^1$H NMR (CDCl₃, 500 MHz) δ 7.15-6.95 (10H, br m), 6.12 (1H, br s), 3.78 (1H, m), 3.66 (1H, m), 3.22 (1H, d, J 16.3 Hz), 3.01 (1H, d, J 13.3 Hz), 2.86 (1H, d, J 13.3 Hz), 2.80 (1H, d J 16.3 Hz), 2.68 (1H, m), 2.36 (1H, d, J 14.6 Hz), 2.02 (1H, m), 1.81 (3H, m), 1.69 (2H, m), 16.2 (2H, m), 1.09 (3H, t, J 7.4 Hz), 0.98 (3H, t, J 7.4 Hz).

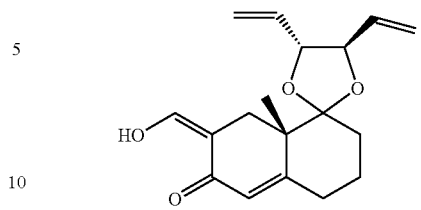

COMPOUND Z

Step 1:

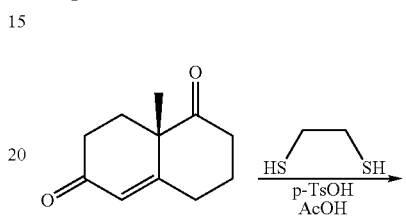

A solution of the Wieland-Miescher ketone (1.00 g, 5.61 mmol) in glacial acetic acid (20 mL) was treated with 1,2-ethanedithiol (529 mg, 529 μL, 5.61 mmol) and a solution of p-toluenesulfonic acid (535 mg, 2.81 mmol) in glacial acetic acid (5 mL). After stirring for 2.5 h, the reaction mixture was poured into water. The resulting suspension was extracted with CHCl₃ (3×60 mL). The combined organic extracts were washed with water (60 mL), 1N aqueous NaOH (60 mL), water (60 mL), brine (60 mL), dried (MgSO₄) and concentrated in vacuo to afford the crude product (1.49 g). This was purified by flash chromatography (35 g Si, 40 ml/min, gradient from 0 to 25% EtOAc in hexanes over 30 min, isocratic at 25% EtOAc in hexanes for 10 min) to give COMPOUND W (1.27 g, 89%) as a colorless solid. LCMS (ES+) 255 (M+H)$^+$; $^1$H NMR (CDCl₃, 500 MHz) δ 5.66 (1H, s), 3.34 (3H, m), 3.24 (1H, m), 2.61 (1H, tdd, 14.9, 6.3, 1.4 Hz), 2.51 (1H, ttd, J 13.7, 4.9, 1.6 Hz), 2.35 (1H, dm, J 15.2 Hz), 2.25-2.10 (4H, m), 2.01 (1H, m), 1.75 (1H, m), 1.60 (1H, m), 1.29 (3H, d, J 1.6 Hz).

Step 2:

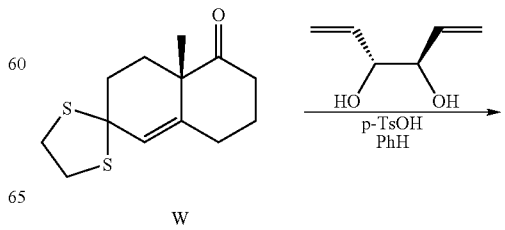

-continued

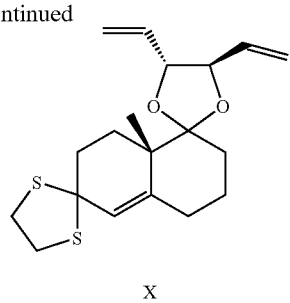

X

A solution of COMPOUND W (730 mg, 2.87 mmol), (3R,4R)-1,5-hexadien-3,4-diol (492 mg, 4.31 mmol) and p-toluenesulfonic acid (164 mg, 0.862 mmol) in benzene (50 mL) was heated at reflux under a Dean-Stark apparatus for 3 h. The reaction mixture was diluted with EtOAc (100 mL) and washed with saturated NaHCO$_3$ (50 mL), water (50 mL) and brine (50 mL), dried (MgSO$_4$) and concentrated in vacuo to afford the crude COMPOUND X (1.06 g) as a colorless oil. This was used in the next step without any further purification. LCMS (ES+) 351 (M+H)$^+$.

Step 3:

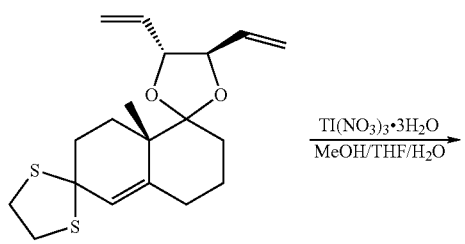

X

Y

A solution of Tl(NO$_3$)$_3$.H$_2$O (1.71 g, 3.85 mmol) in MeOH (200 mL) was added rapidly to a solution of COMPOUND X in THF (66 mL) and water (1.3 mL). The turbid mixture was stirred for 1 h and the colorless precipitate produced was removed by filtration. The filtrate was diluted with Et$_2$O (200 mL) and washed successively with water (100 mL), saturated NaHCO$_3$ (100 mL) and brine (100 mL), then dried (MgSO$_4$) and concentrated in vacuo to give the crude product (993.9 mg). This was purified by flash chromatography (35 g Si, gradient from 0 to 20% EtOAc in hexanes over 25 min, isocratic at 20% EtOAc in hexanes for 10 min) to give COMPOUND Y (374.8 mg, 44%) as a colorless oil. LCMS (ES+) 275 (M+H)$^+$; $^1$H NMR (CDCl$_3$, 600 MHz) δ 5.81 (1H, d, J 1.9 Hz), 5.80 (1H, ddd, J 17.0, 10.2, 6,7 Hz), 5.74 (1H, ddd, J 17.0, 10.2, 6.7 Hz), 5.40 (1H, d, J 17.0 Hz), 5.32 (1H, d, J 17.0 Hz), 5.29 (1H, d J 10.2 Hz), 5.22 (1H, d, J 10.2 Hz), 4.17 (1H, t, 7.8 Hz), 4.00 (1H, t, J 7.5 Hz), 2.43 (3H, m), 2.29 (2H, m), 1.99 (1H, m), 1.81 (4H, m), 1.36 (3H, s).

Step 4:

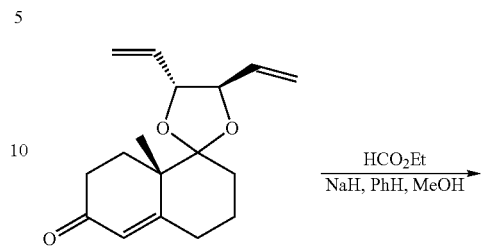

Y

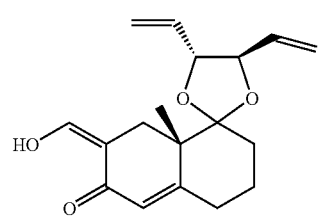

Z

COMPOUND Z was synthesized by a method analogous to COMPOUND G. LCMS (ES+) 304 (M+H).

EXAMPLES

Example 272

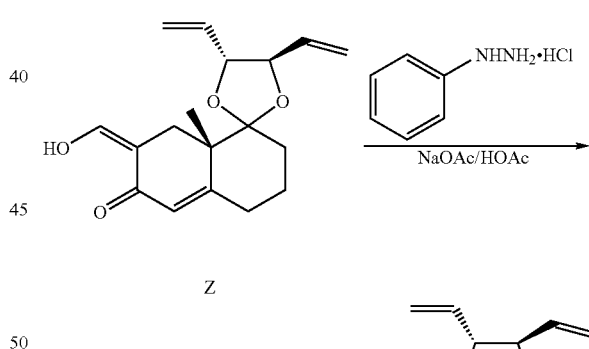

Z

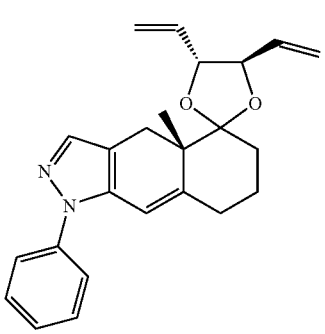

Example 272

Example 272 was synthesized by a method analogous Example 139. LCMS (ES+) 375 (M+H)$^+$; $^1$H NMR (CDCl$_3$, 500 MHz) δ 7.56 (5H, m), 7.33 (1H, m), 6.30 (1H, s), 5.84 (1H, ddd, J 16.8, 10.2, 6.6 Hz), 5.69 (1H, ddd, J 16.8, 10.2, 6.6

Hz), 5.40 (1H, d, J 16.8 Hz), 5.30 (1H, d, J 16.8 Hz), 5.28 (1H, d, J 10.2 Hz), 5.21 (1H, d, J 10.2 Hz), 4.22 (1H, t, 7.7 Hz), 4.1 (1H, t, J 7.7 Hz), 3.20 (1H, d J 15.5 Hz), 2.60 (1H, d, J 15.5 Hz), 2.50 (3H, m) 2.30 (2H, m), 1.91 (5H, m), 1.30 (3H, s).

The following compounds are synthesized from either enantiopure or racemic hydroxyketone Z and commercially available alkyl or aryl hydrazines, using procedures analogous to that described for compounds in the table above:

| Example | Molecular structure | LCMS (M + 1)+ |
|---|---|---|
| 273 | 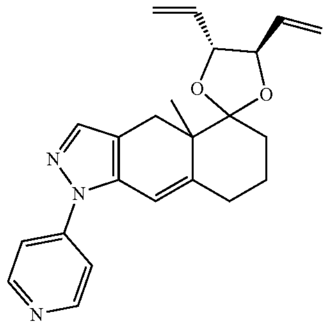 | 376 |
| 274 | 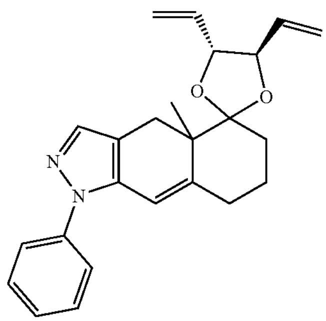 | 375 |
| 275 | 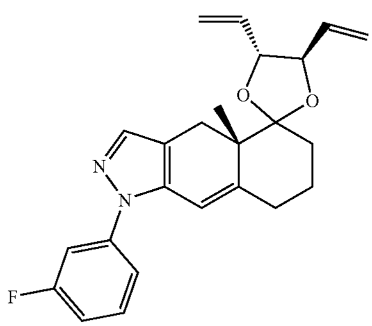 | 393 |
| 276 | 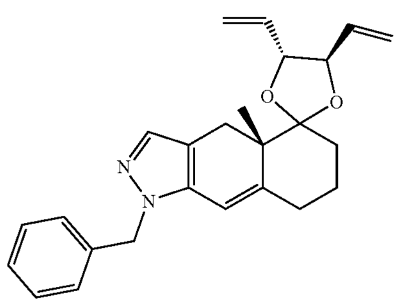 | 389 |
| 277 | | 367 |
| 278 | | 381 |
| 279 | | 432 |
| 280 | | 409 |

-continued

| Example | Molecular structure | LCMS (M + 1)+ |
|---|---|---|
| 281 | 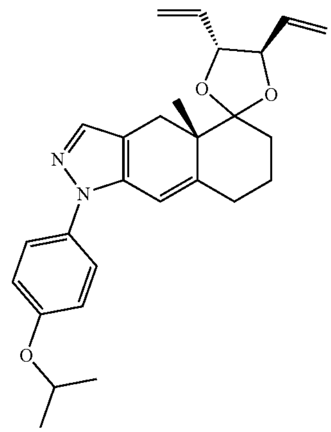 | 433 |
| 282 | 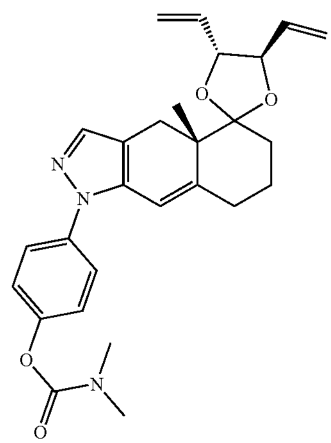 | 462 |
| 283 | 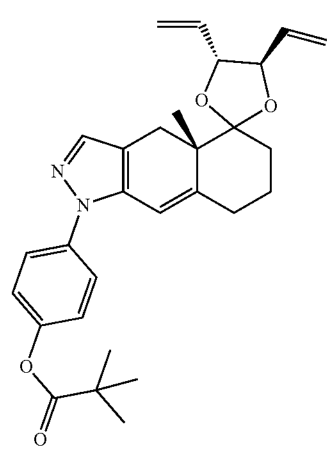 | 475 |

-continued

| Example | Molecular structure | LCMS (M + 1)+ |
|---|---|---|
| 284 | 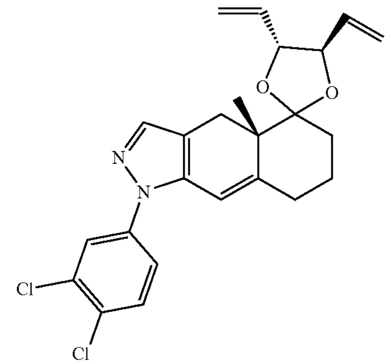 | 445 |
| 285 | 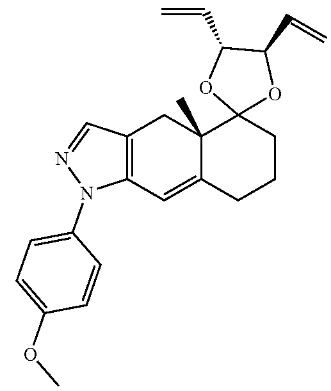 | 405 |
| 286 | 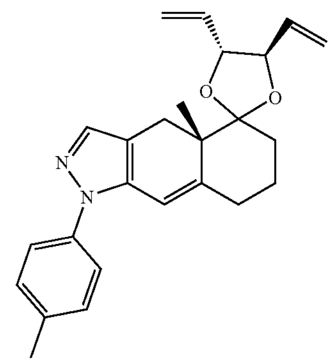 | 389 |
| 287 | 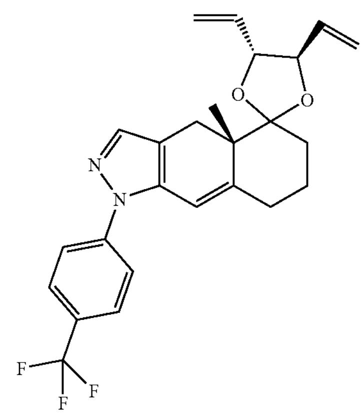 | 443 |

-continued

| Example | Molecular structure | LCMS (M + 1)+ |
|---------|---------------------|---------------|
| 288 | 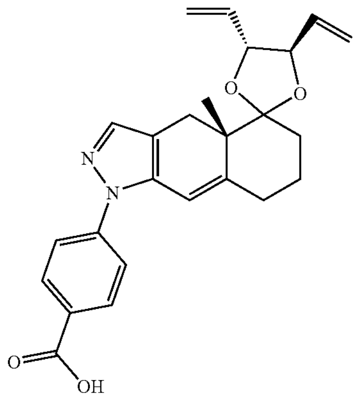 | 419 |

The following compounds are synthesized from racemic COMPOUND A and commercially available alkyl or aryl hydrazines, using procedures analogous to that described for Example 272:

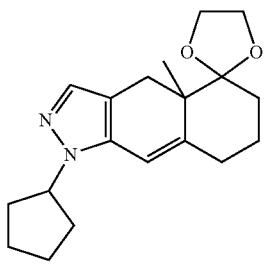

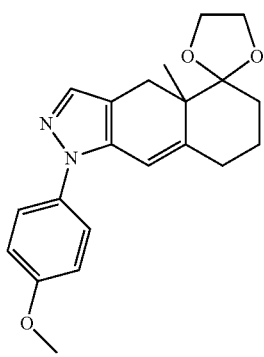

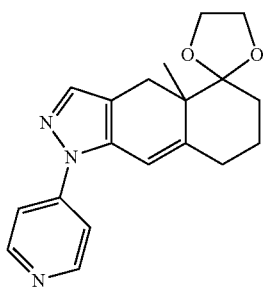

Biological Assays

The activity of the compounds of the present invention regarding glucocorticoid receptor affinity can be evaluated using the following human GR binding assay:

GR Ligand Binding Assay

For the hGRI ligand binding assay, cytosols were prepared from recombinant baculovirus expressed receptors. Frozen cell pellets were dounce homogenized in ice cold $KPO_4$ buffer (10 mM $KPO_4$, 20 mM sodium molybdate, 1 mM EDTA, 5 mM DTT and complete protease inhibitor tablets from Boehringer Mannheim) with a "B" plunger. The homogenates were centrifuged at 35,000× g for 1 h at 4° C. in a JA-20 rotor. The $IC_{50s}$ were determined by incubating the cytosols at a final concentration of 2.5 nM [1,2,4,6,7-$^3$H] Dexamethasone in the presence of increasing concentrations (10-11 to 10-6) of cold dexamethasone or the ligands at 4° C. for 24 h. Bound and free were separated by a gel filtration assay, (Geissler et al., personal communication). Half of the reaction was added to a gel filtration plate (MILLIPORE) containing sephadex G-25 beads that was previously equilibrated with KPO4 buffer containing 1 mg/ml BSA and centrifuged at 1000× g for 5 min. The reaction plate was centrifuged at 1000× g for 5 min. and the reactions were collected in a second 96-well plate and scintillation cocktail was added and counted in (Wallac) double coincidence beta counter. The $IC_{50}$ values were calculated using a 4-parameter fit program.

The compounds of this invention demonstrated a range of GR affinity in the above assay with IC$_{50}$ values between 10 uM and 1 nM. The most advantageous compounds of Formula I and Formula II demonstrated IC$_{50}$ values between 50 nM and 1 nM.

What is claimed is:

1. A compound of Formula II

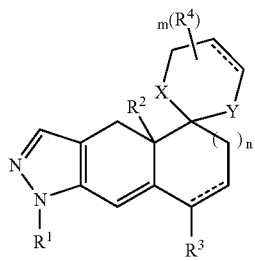

wherein
m is 0, 1 or 2;
n is 0 or 1;
X and Y are each independently selected from CH$_2$, S and O;
R$^1$ is phenyl or pyridyl said phenyl or pyridyl optionally mono or di- substituted with a substituent independently selected from the group consisting of:
(a) halo,
(b) OCH$_3$,
(c) CH$_3$, and
(d) CN;
R$^2$ and R$^3$ are each individually hydrogen or methyl; and
each R$^4$ is independently selected from the group consisting of
(1) —OH,
(2) —C$_{1-6}$alkyl optionally substituted with 1, 2 or 3 substituents selected independently from hydroxy, oxo, —COOH, amino, methylamino, di-methylamino, =S, and halo,
(3) C$_{2-6}$alkenyl optionally substituted with 1, 2 or 3 substituents selected independently from hydroxy, halo and —C(O)—O—C$_{1-2}$alkyl,
(4) C$_{2-6}$alkynyl optionally substituted with 1, 2 or 3 substituents selected independently from hydroxy and halo,
(5) phenyl optionally substituted with 1, 2 or 3 substituents selected independently from hydroxy, C$_{1-2}$alkyl, —COOH, —C(O)—O—CH$_3$ and halo,
(6) —C$_{1-2}$alkyl-phenyl optionally substituted with 1, 2 or 3 substituents independently selected from hydroxy, C$_{1-2}$alkyl and halo,
(7) —CO$_2$H,
(8) —CO$_2$C$_{1-3}$alkyl,
(9) —OC$_{1-3}$alkyl,
(10) —SO$_2$—C$_{1-3}$alkyl,
(11) —SO$_2$-phenyl optionally substituted with 1, 2 or 3 substituents independently selected from hydroxy, C$_{1-2}$ alkyl and halo
(12) —C$_{1-2}$alkyl-O—C$_{1-2}$alkyl,
(13) —C$_{1-2}$alkyl-O—C$_{2-4}$alkenyl,
(14) —C$_{1-2}$alkyl-O-phenyl optionally substituted with with 1, 2 or 3 substituents independently selected from hydroxy, C$_{1-2}$alkyl and halo,
(15) —C$_{1-2}$alkyl-C(O)O—C$_{1-2}$alkyl,
(16) 2-(1,3-dioxan)ethyl,
(17) —C$_{1-2}$alkyl-C(O)—NH-phenyl and
(18) —C$_{1-2}$alkyl-C(O)—NHN.

2. A compound according to claim 1 wherein each R$^4$ is independently selected from the group consisting of —C$_{1-6}$ alkyl or hydrogen.

3. A compound according to claim 1 wherein X and Y are both O or are both S or X is O and Y is CH$_2$; and
R$^1$ is phenyl optionally mono or di-substituted with halo.

4. A compound selected from the group consisting of the following groups:

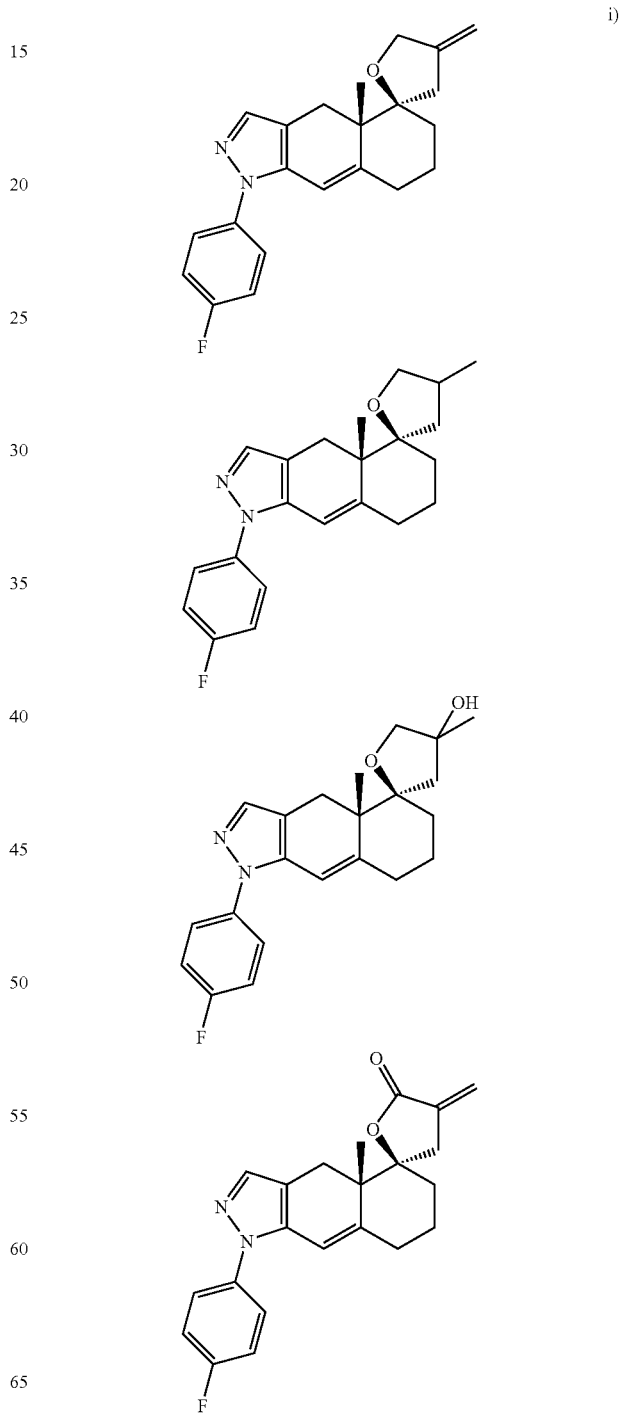

195
-continued
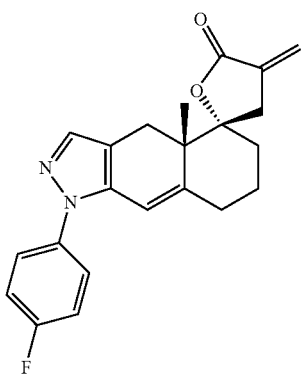
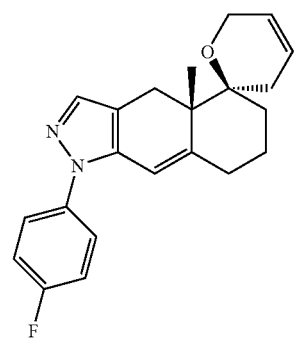
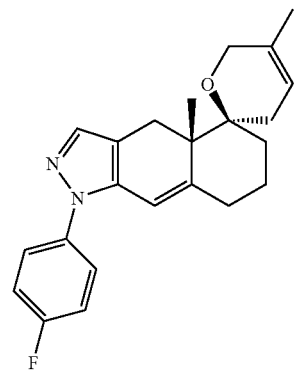
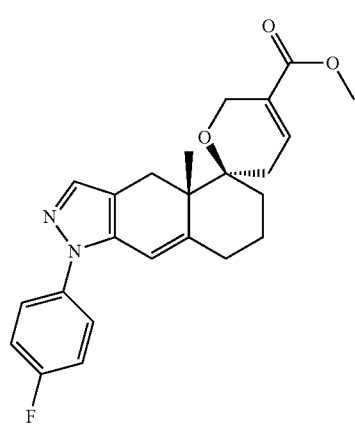
196
-continued
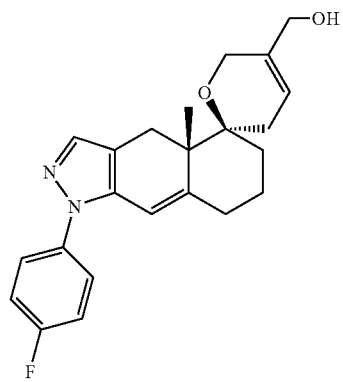
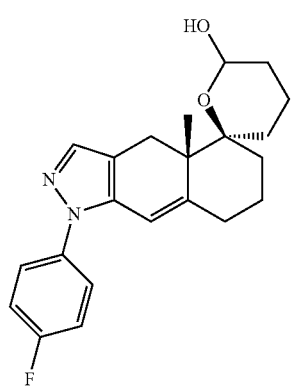
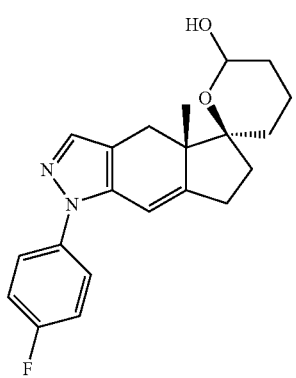
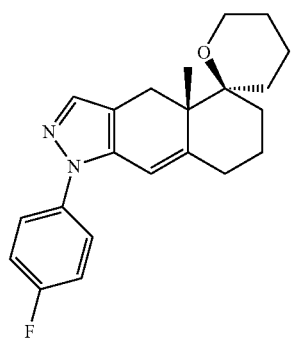

197
-continued
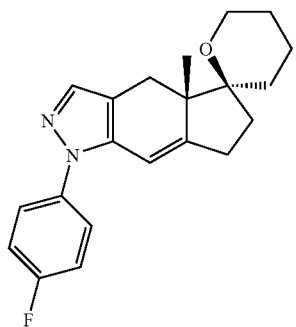
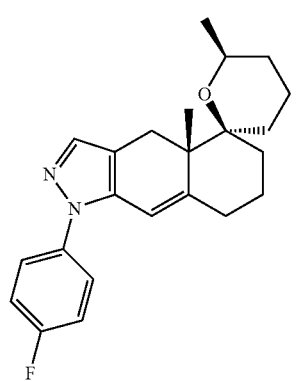
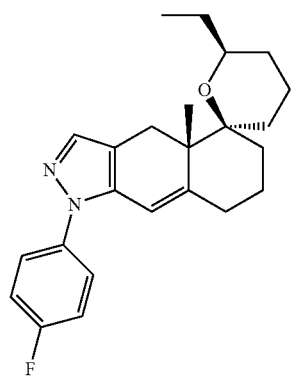
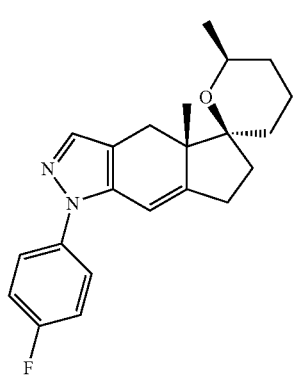
198
-continued
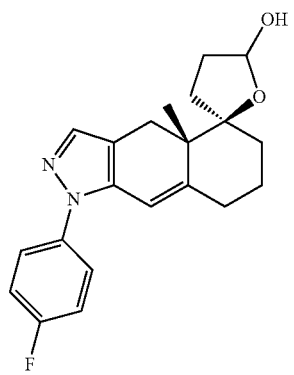
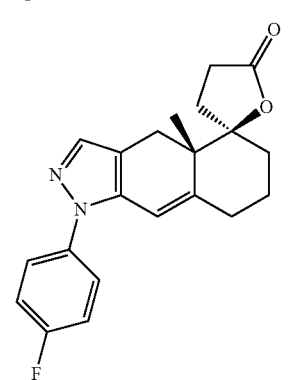
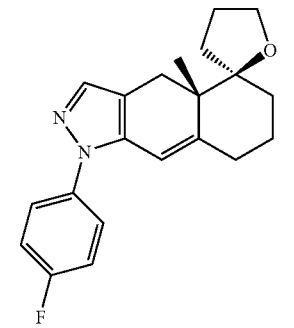
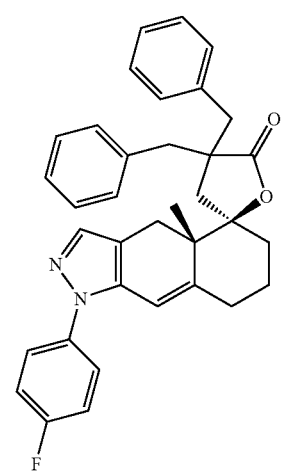

199
-continued
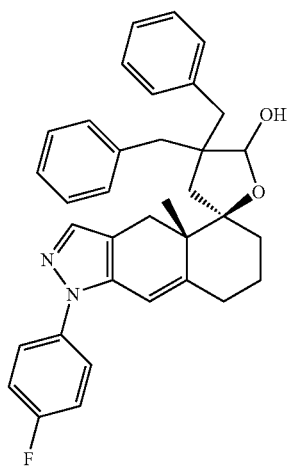
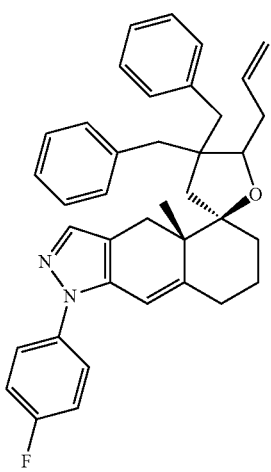
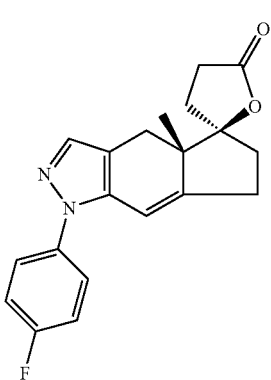
200
-continued
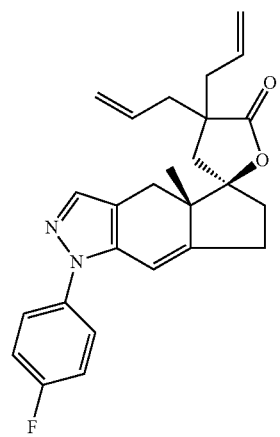
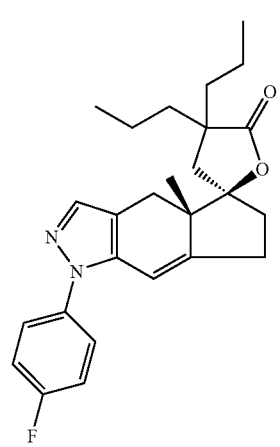
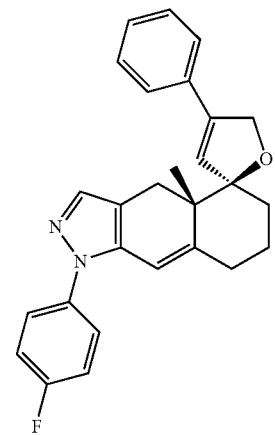

-continued

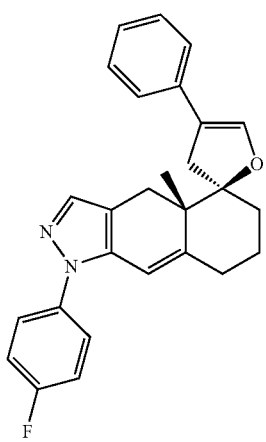

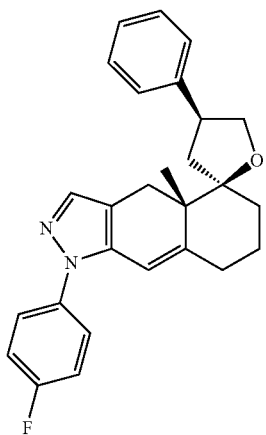

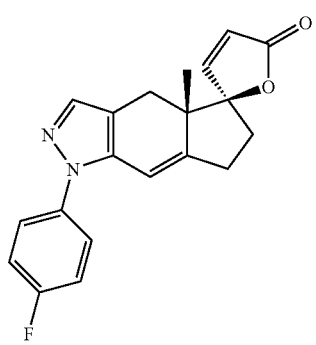

ii)

[Structure with R substituent and (  )k]

| k | R |
|---|---|
| 1 | Vinyl |
| 1 | Phenyl |
| 1 | 4-fluorophenyl |
| 2 | Benzyl |
| 2 | Vinyl |
| 2 | Ethyl | iii)

[Structure with Ra, Rb, A, C, D substituents and (  )k]

| k | D | A | C | Ra | Rb |
|---|---|---|---|---|---|
| 1 | O | $CH_2$ | $CH_2$ | propyl | Propyl |
| 1 | O | $CH_2$ | CHOH | propyl | Propyl |
| 1 | O | $CH_2$ | $CH_2$ | allyl | Allyl |
| 1 | O | $CH_2$ | CHOH | allyl | Allyl |
| 1 | O | $CH_2$ | $CH_2$ | methyl | Methyl |
| 1 | O | $CH_2$ | CHOH | methyl | Methyl |
| 1 | O | $CH_2$ | C(O) | methyl | Methyl |
| 1 | O | $CH_2$ | $CH_2$ | H | H |
| 1 | O | $CH_2$ | CHOH | H | H |
| 2 | $CH_2$ | O | $CH_2$ | ethyl | H |
| 2 | $CH_2$ | O | $CH_2$ | H | Ethyl |
| 2 | $CH_2$ | O | $CH_2$ | H | Phenyl |
| 2 | O | $CH_2$ | CH(allyl) | allyl | Allyl |
| 2 | O | $CH_2$ | $CH_2$ | methyl | Methyl |
| 2 | O | $CH_2$ | $CH_2$ | benzyl | Benzyl |
| 2 | O | $CH_2$ | $CH_2$ | allyl | Allyl |
| 2 | O | $CH_2$ | CHOH | methyl | Methyl |
| 2 | O | $CH_2$ | CHOH | allyl | Allyl |
| 2 | O | $CH_2$ | CH(allyl) | H | H |
| 2 | O | $CH_2$ | C(O) | methyl | Methyl |
| 2 | O | $CH_2$ | C(O) | allyl | Allyl |

203
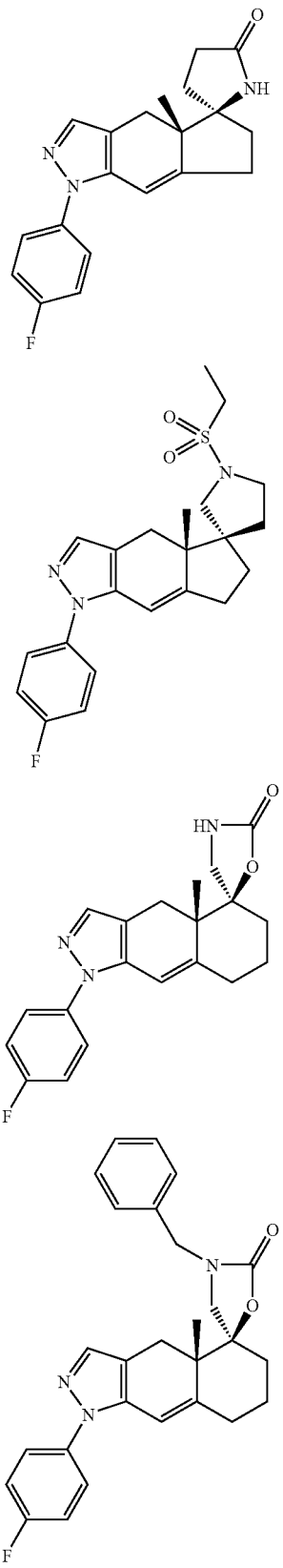
204
-continued
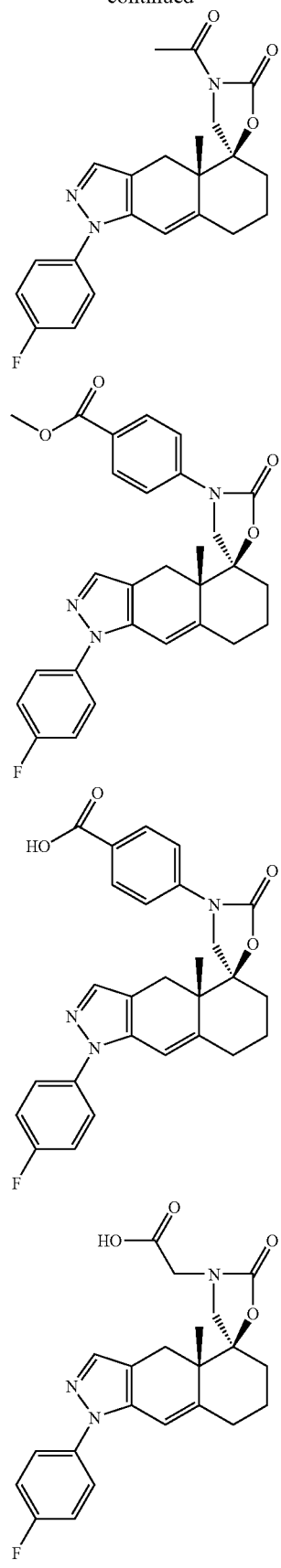

-continued
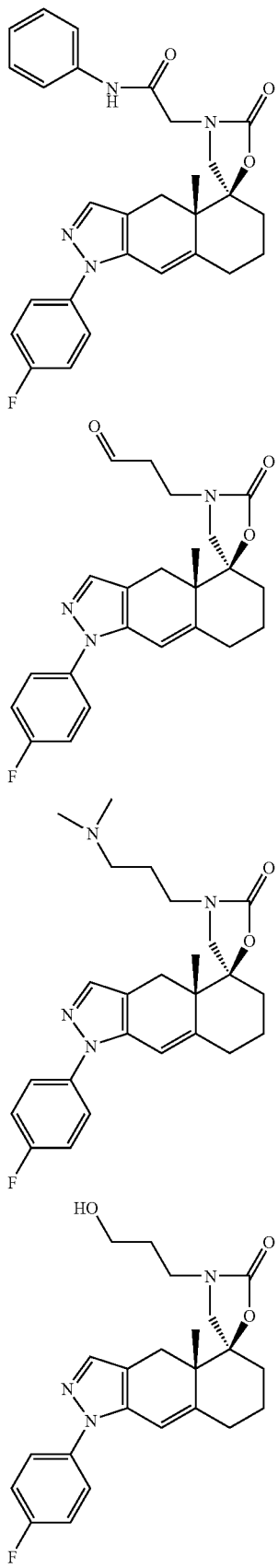
-continued
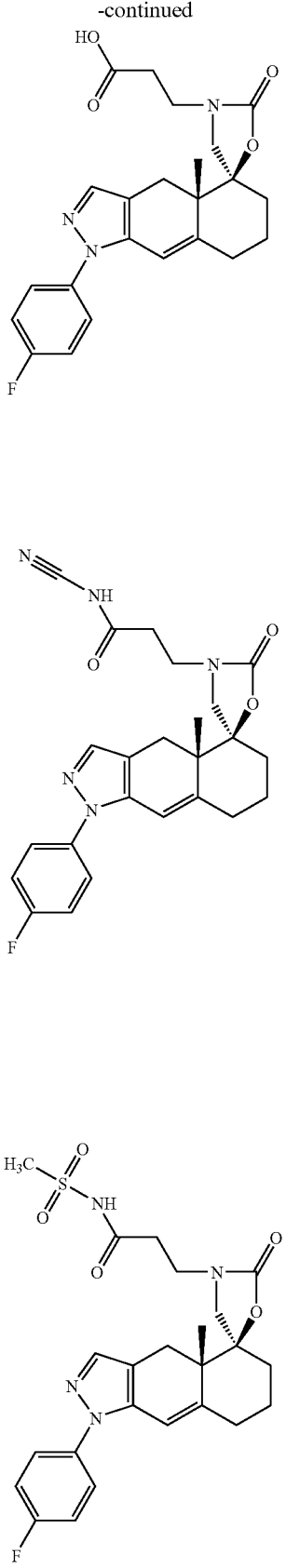

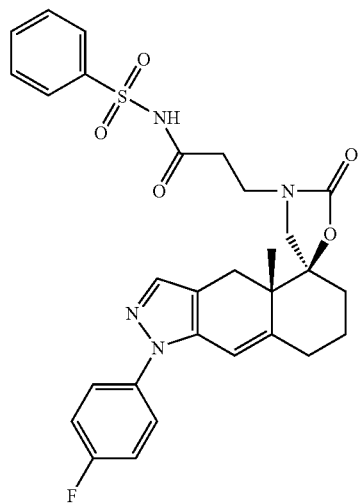
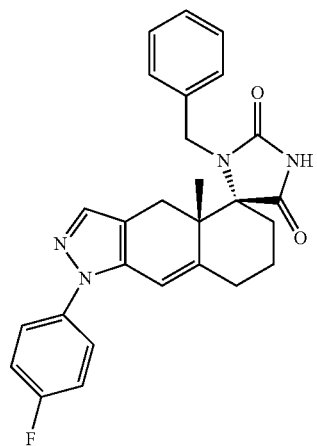
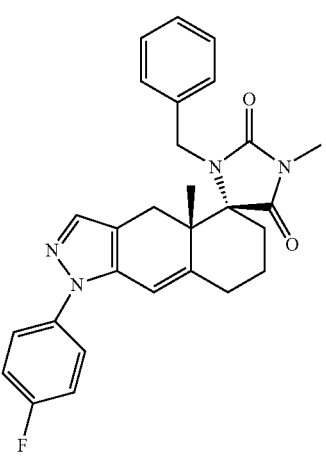
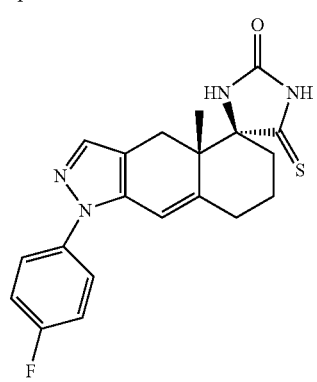
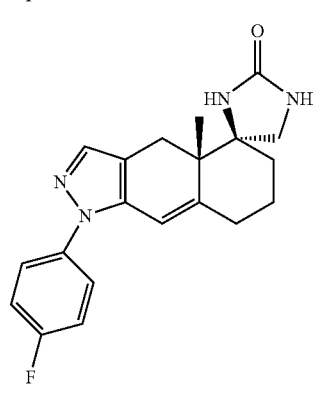

209
-continued
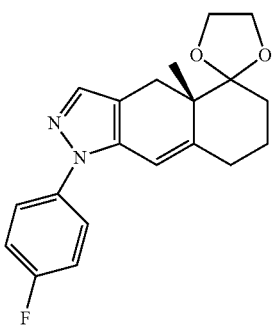
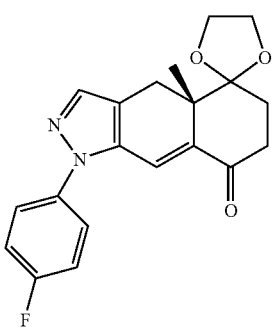
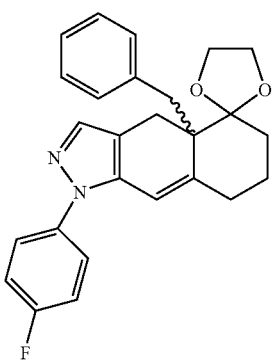
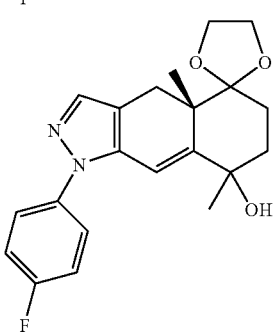
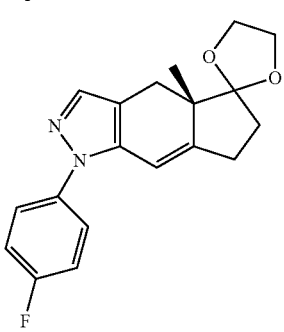
210
-continued
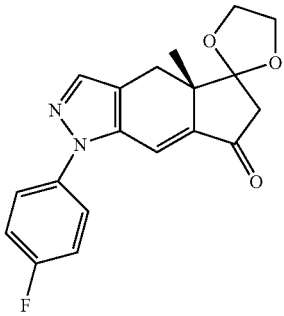
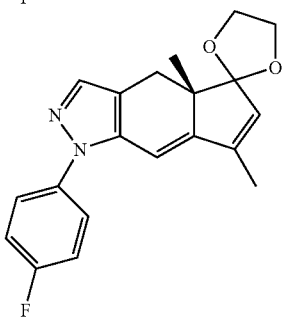
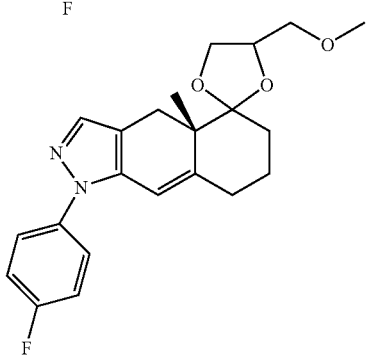
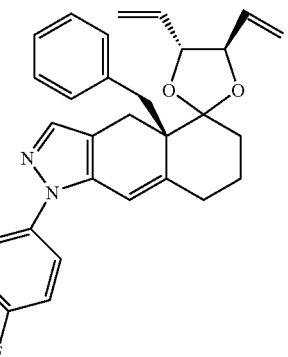
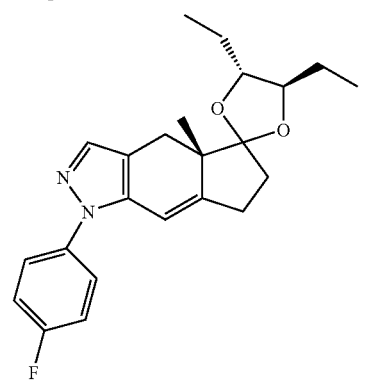

211
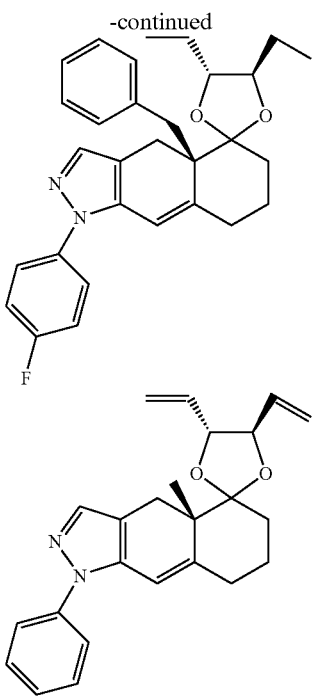
212
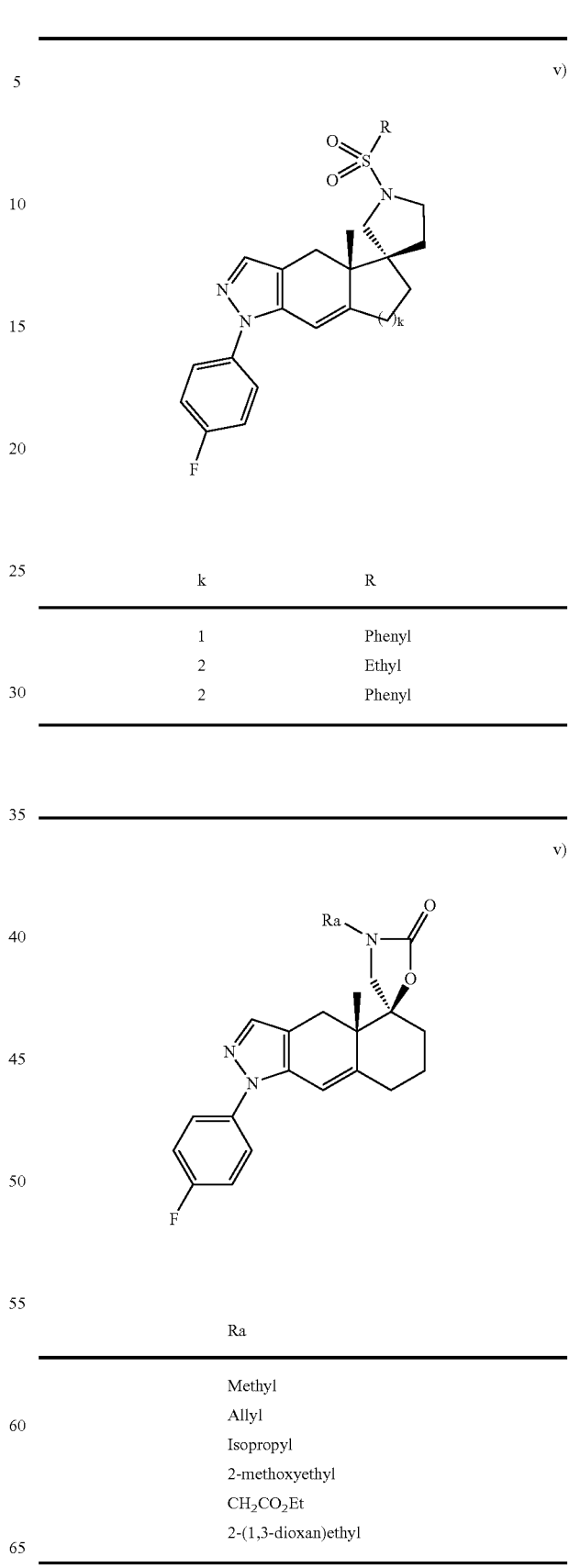
| k | R |
|---|---|
| 1 | Phenyl |
| 2 | Ethyl |
| 2 | Phenyl |
v)
| Ra |
|---|
| Methyl |
| Allyl |
| Isopropyl |
| 2-methoxyethyl |
| CH$_2$CO$_2$Et |
| 2-(1,3-dioxan)ethyl | vii)

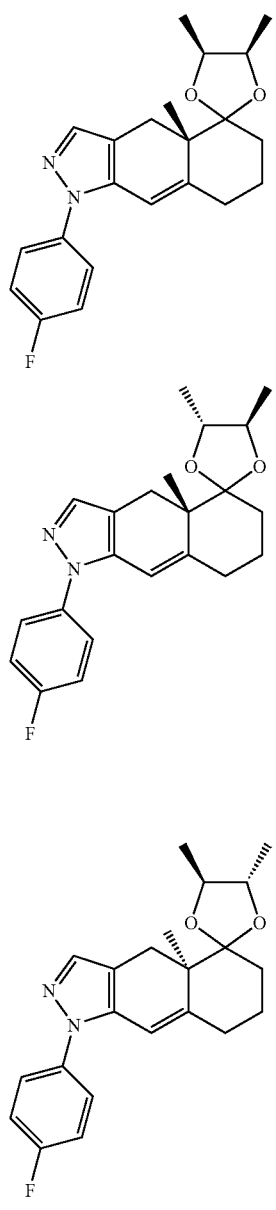

| C₁ | D₁ | A₁ | B₁ |
|---|---|---|---|
| C(O) | NCH₃ | C(O) | NH |
| NCH₂Ph | C(O) | NCH₃ | C(O) |
| NCH₃ | C(O) | NCH₃ | C(O) |
| NCH₂CH=CH₂ | C(O) | NCH₃ | C(O) |
| C(O) | NCH₃ | C(O) | NCH₂Ph |
| C(O) | NCH₃ | C(O) | NCH₃ |
| C(O) | NCH₃ | C(O) | NCH₂CH=CH₂ |
| C(O) | NCH₃ | C(O) | NH |
| N(CH₂)₂CO₂H | C(O) | NCH₂Ph | C(O) |
| NH | C(O) | N(CH₂)₂CO₂H | C(O) |
| NH | C(O) | N(CH₂)₂-[1,3-dioxane-2-yl] | C(O) |
| C(O) | NCH₃ | C(O) | N(CH₂)₂CO₂H |
| C(O) | NCH₃ | C(O) | N(CH₂)₂-[1,3-dioxane-2-yl] |
| NCH₂CH=CH₂ | C(O) | NCH₂CH=CH₂ | C(O) |
| •NCH₂Ph | C(O) | NCH₂Ph | C(O) |
| NH | C(S) | NCH₂Ph | C(O) |
| NH | C(S) | NH | C(O) |
| NH | C(S) | NCH₂CH=CH₂ | C(O) |
| NH | C(S) | NCH₃ | C(O) |
| NH | CH₂ | NCH₂Ph | C(O) |
| NH | CH₂ | NH | C(O) |
| C(O) | NCH₃ | CH₂ | NCH₃ |
| NH | CH₂ | NCH₃ | C(O) | and viii)

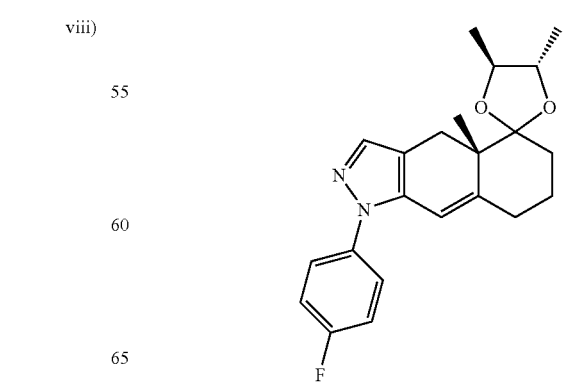

215
-continued
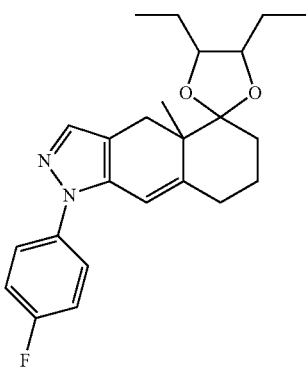
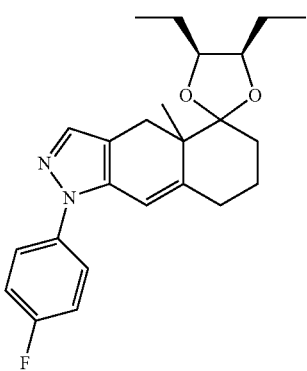
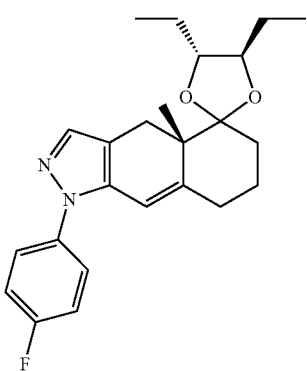
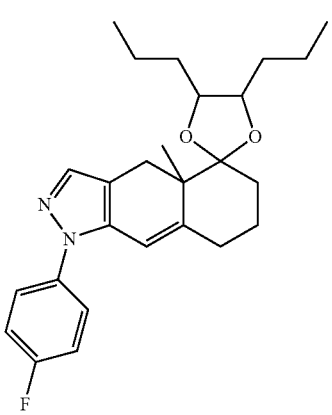
216
-continued
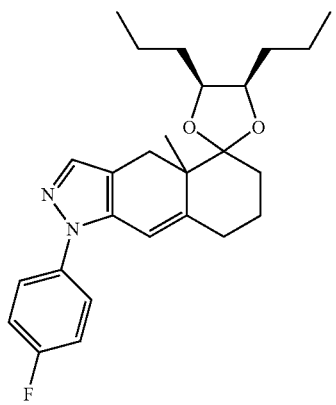
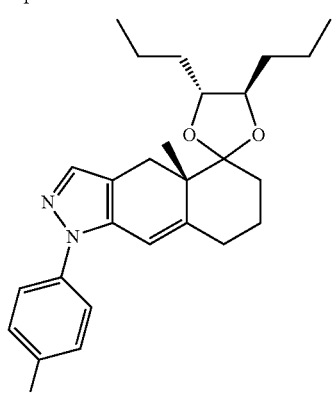
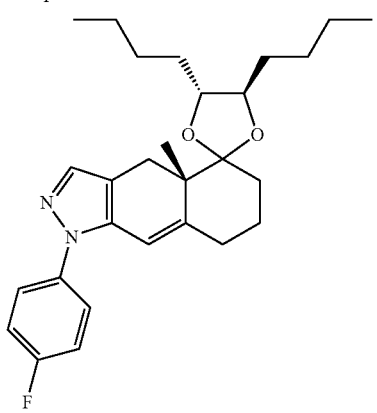
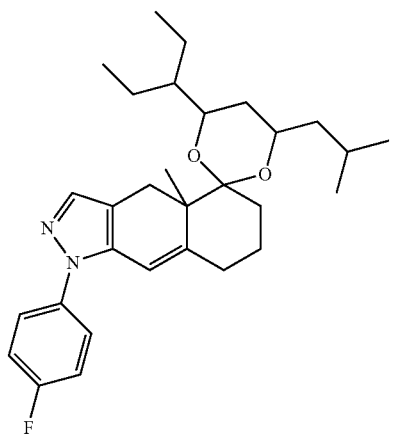

-continued
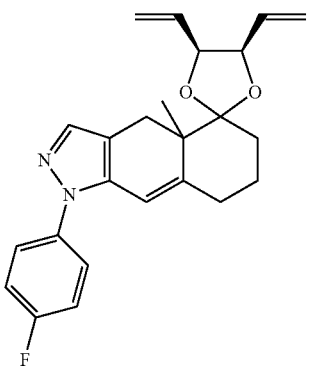
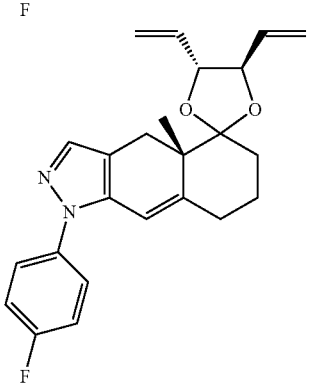
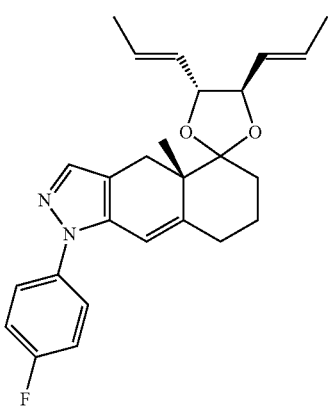
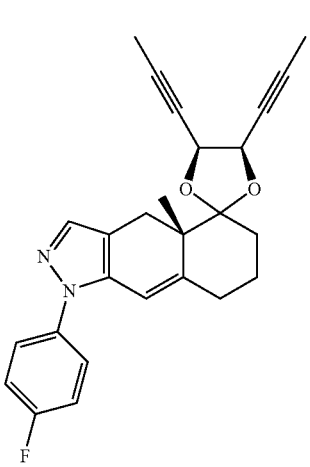
-continued
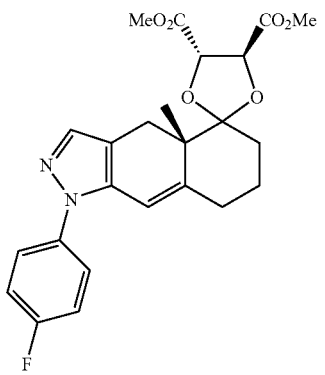
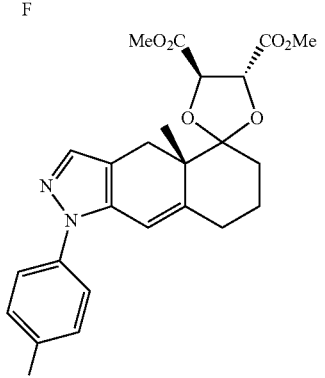
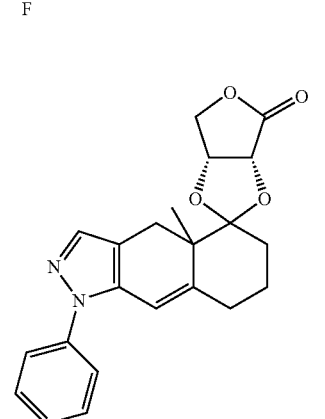
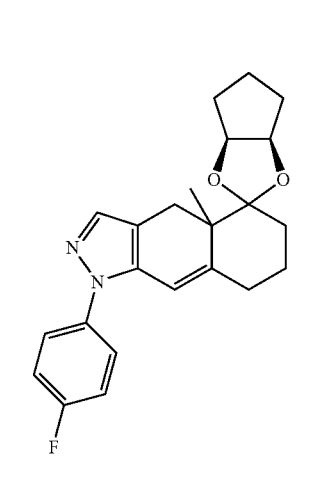

-continued
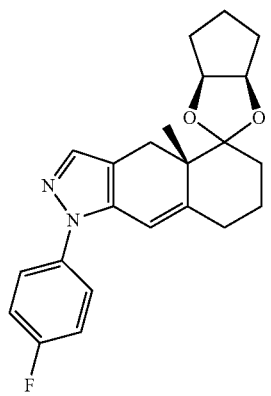
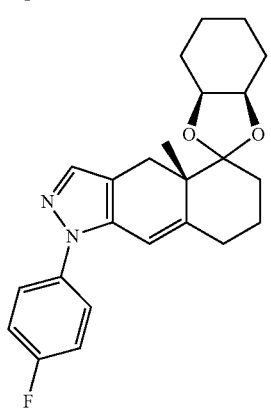
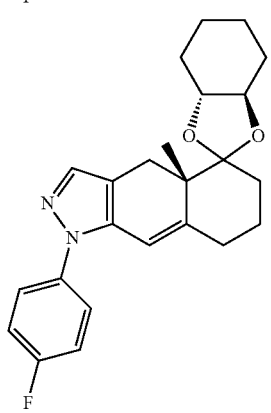
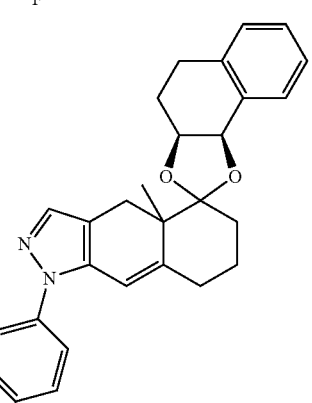
-continued
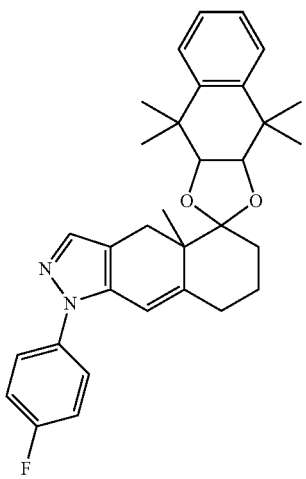
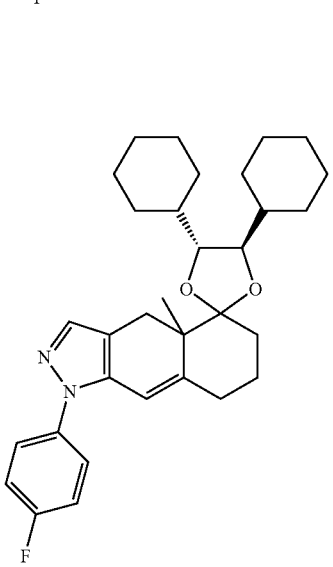
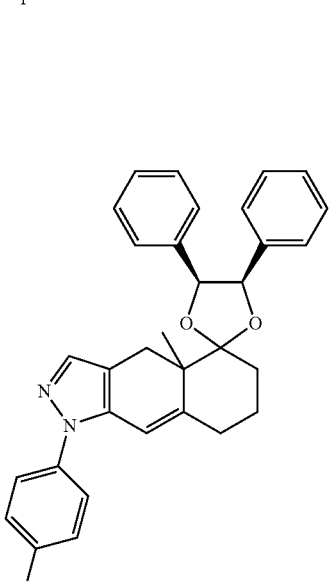

-continued
221
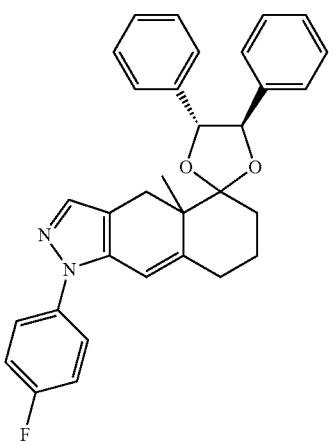
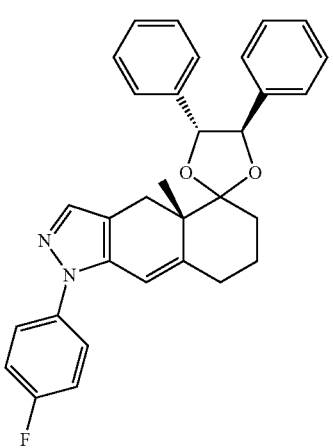
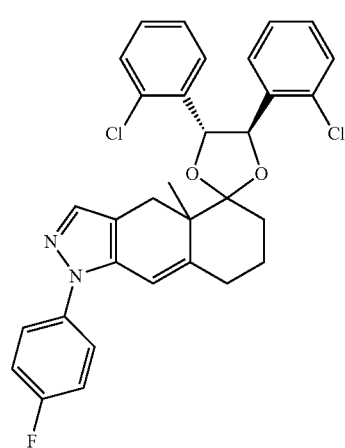
222
-continued
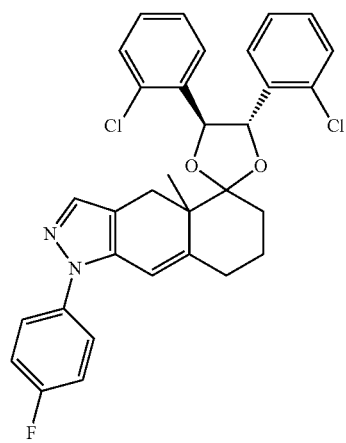
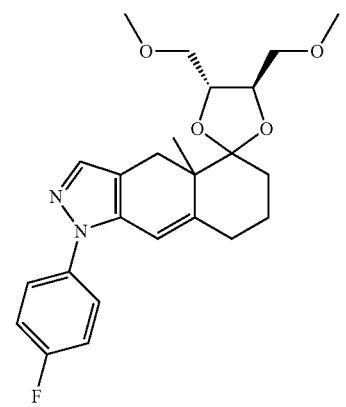
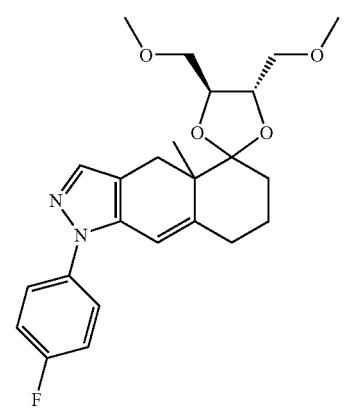

223
-continued
224
-continued
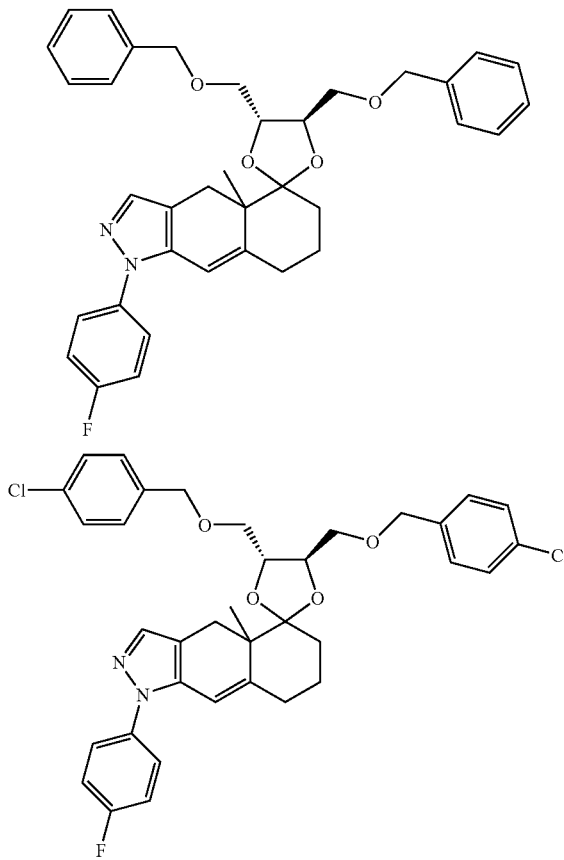
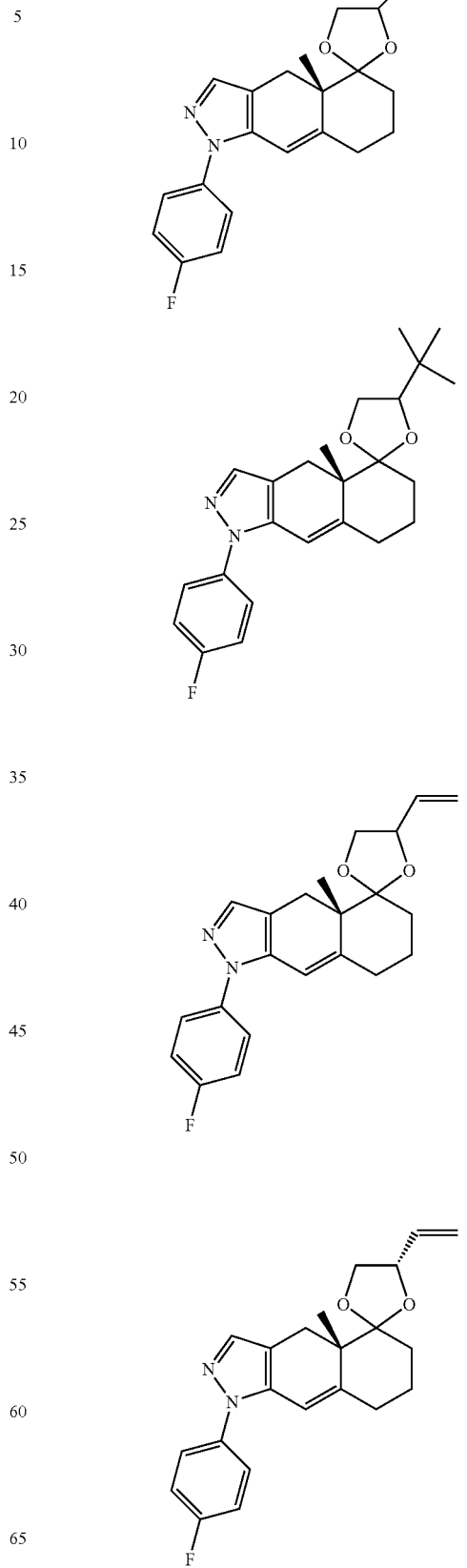

225
-continued
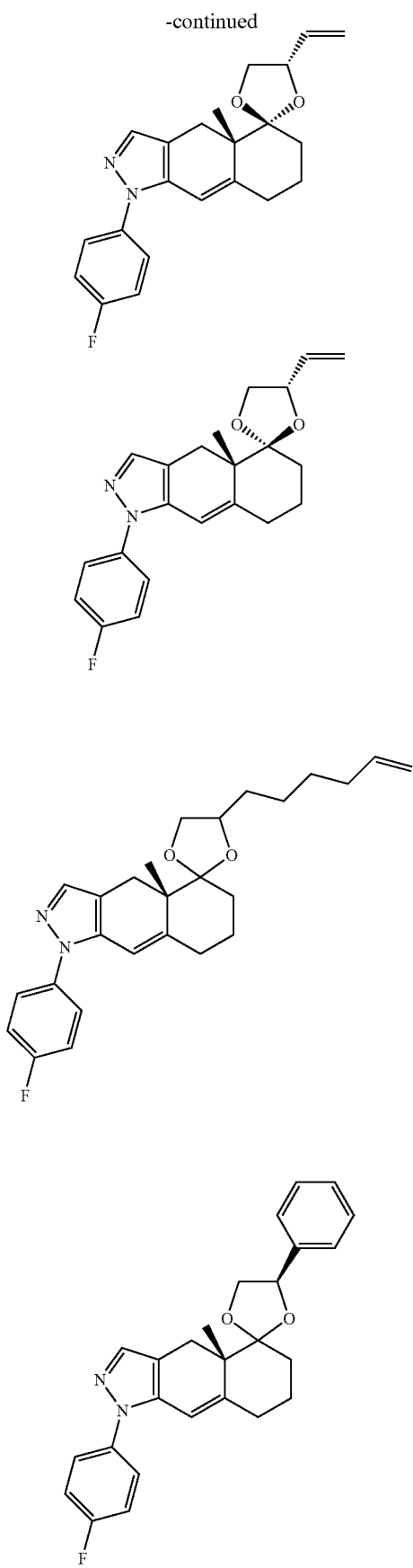
226
-continued
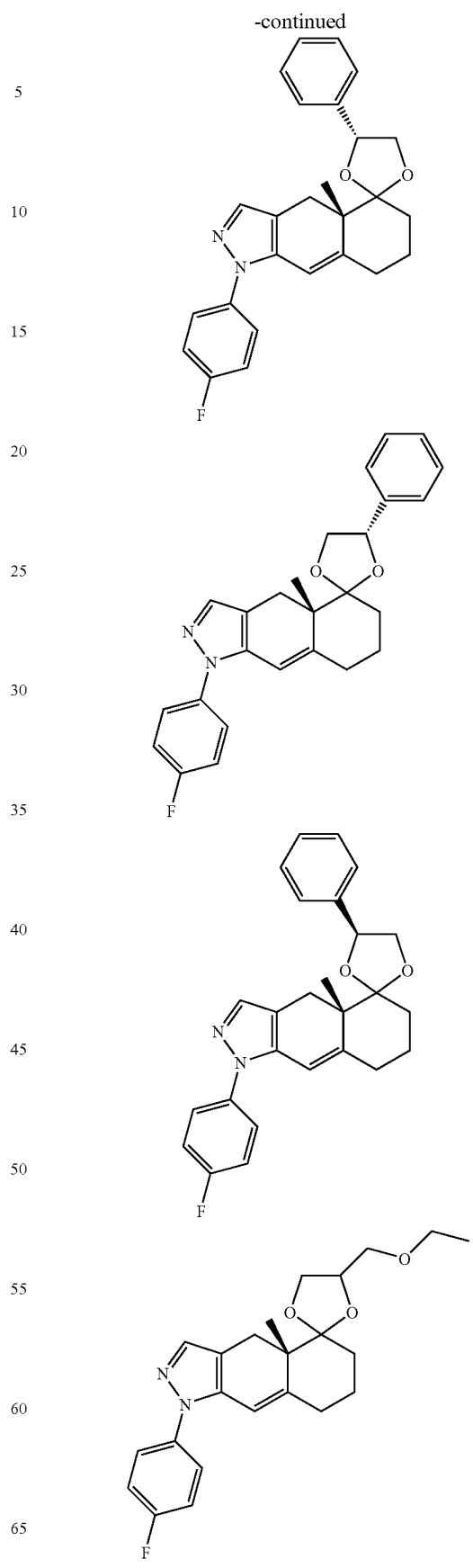

227
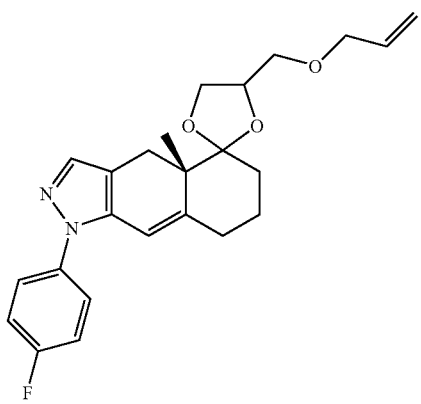
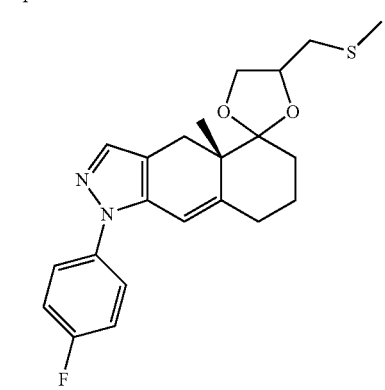
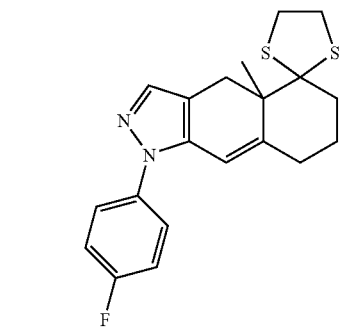
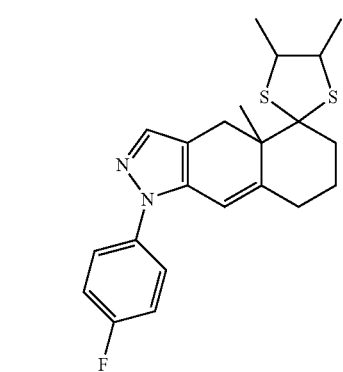
228
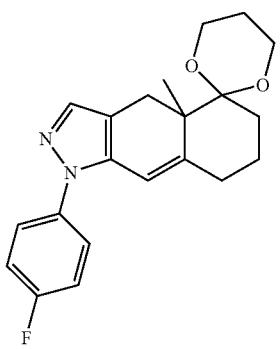
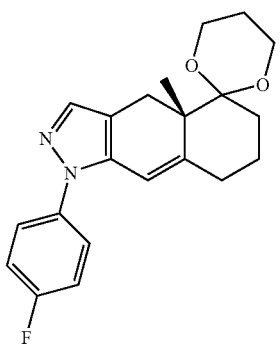
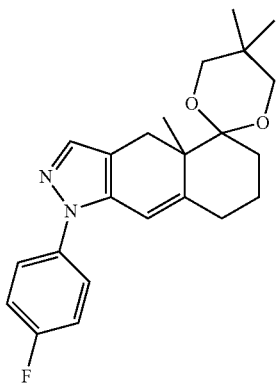
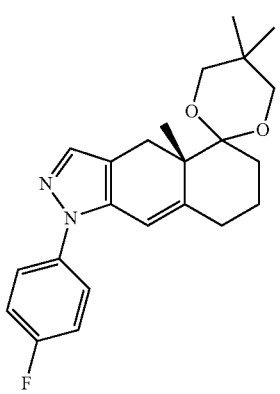

229
-continued
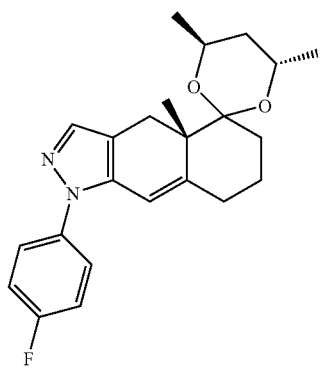
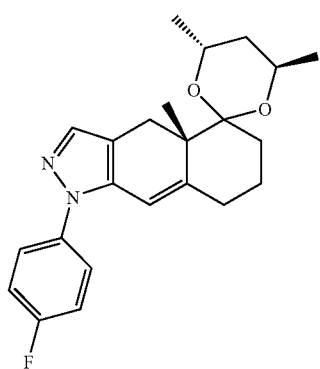
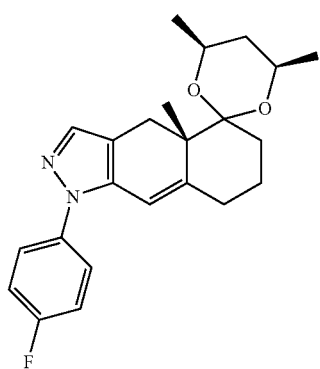
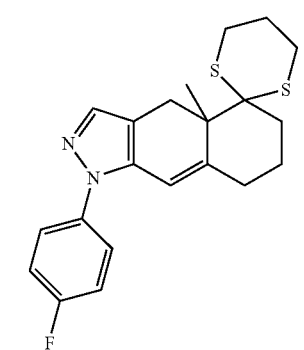
230
-continued
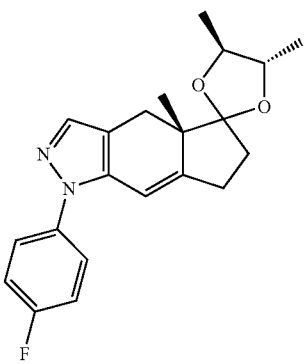
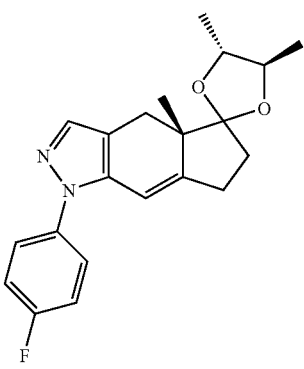
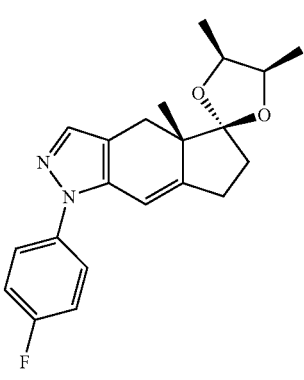
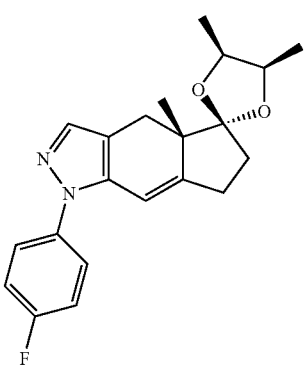

231
-continued
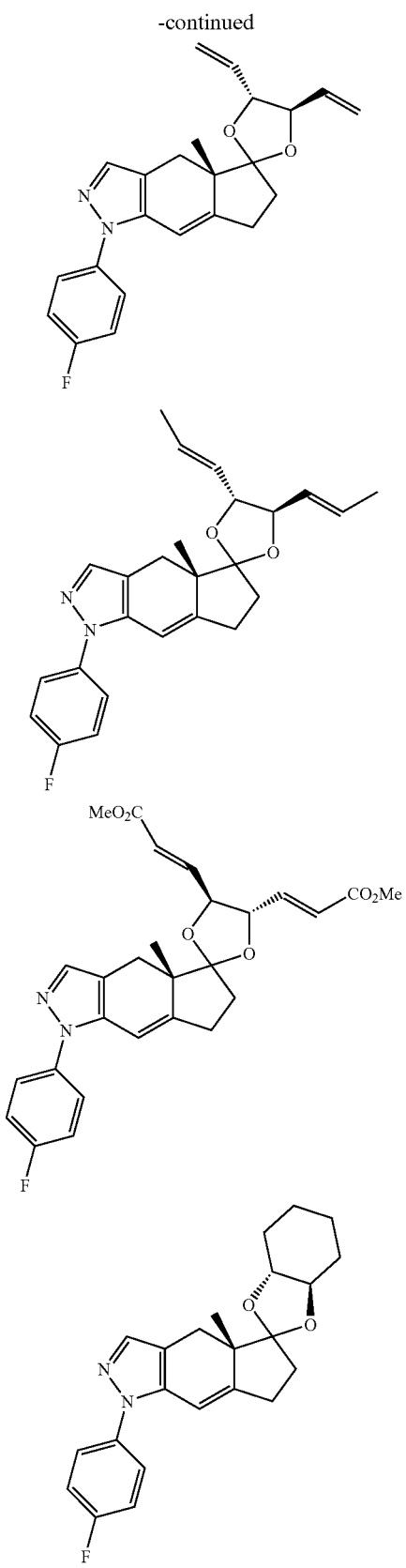
232
-continued
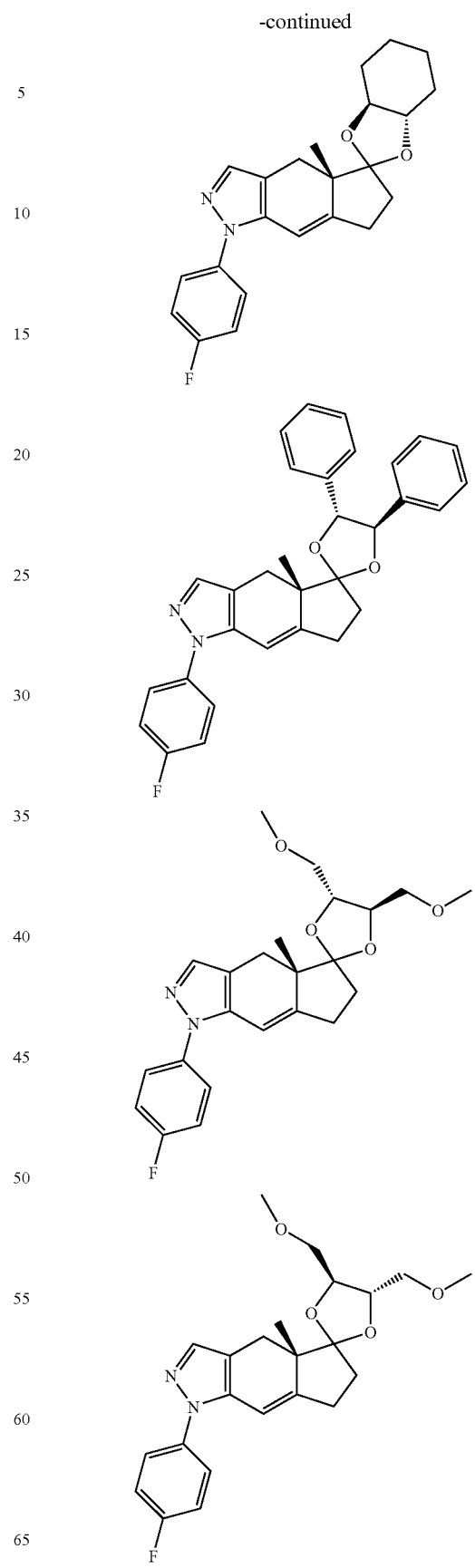

233
-continued
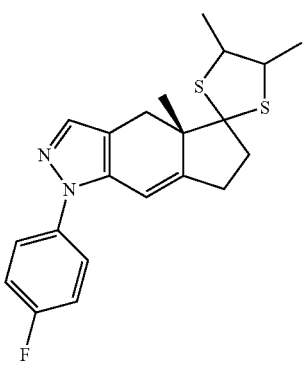
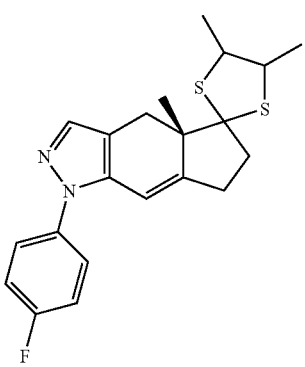
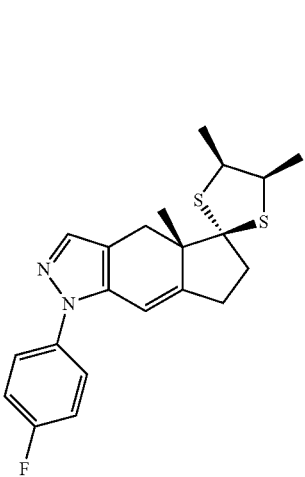
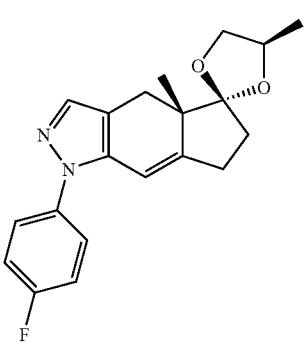
234
-continued
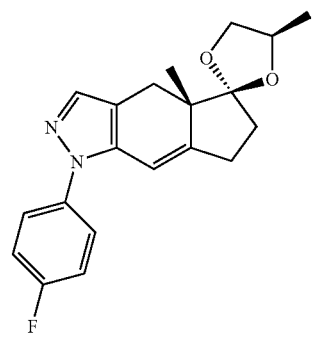
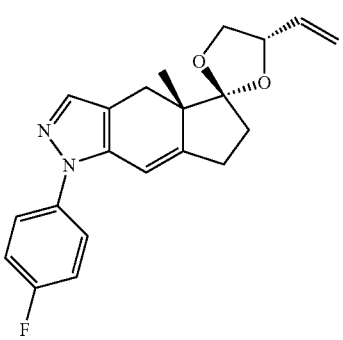
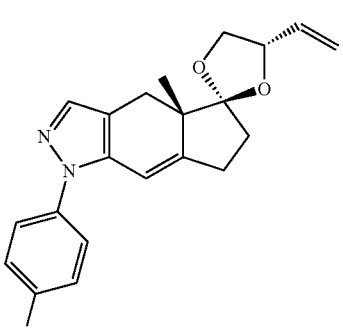
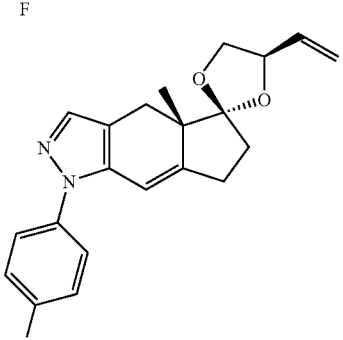
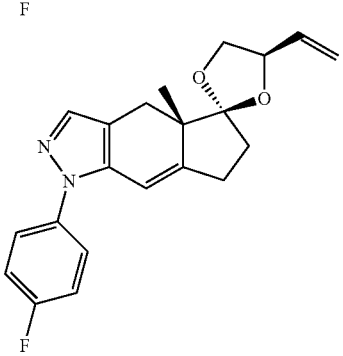

235
-continued
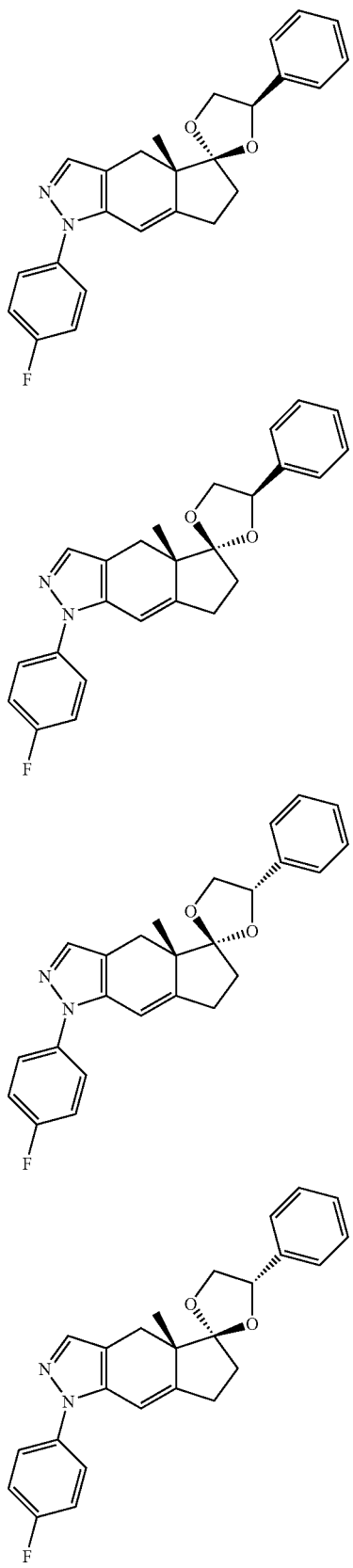
236
-continued
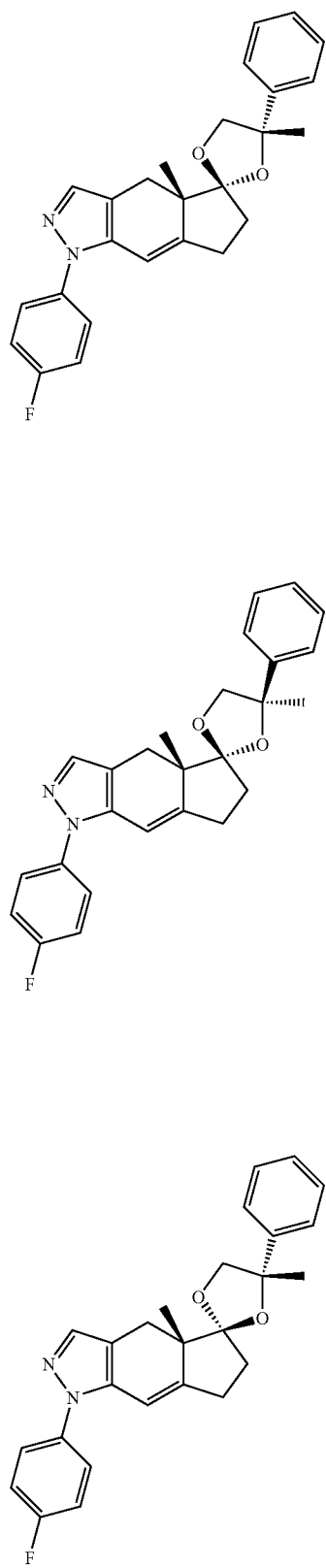

237
-continued
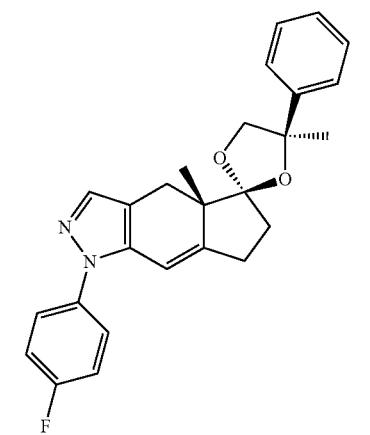
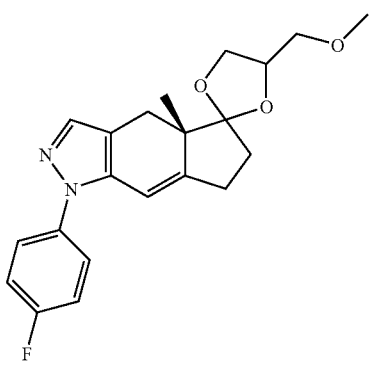
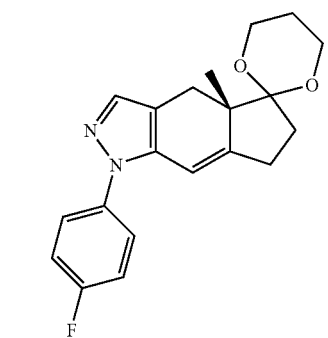
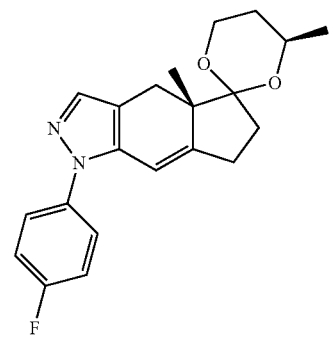
238
-continued
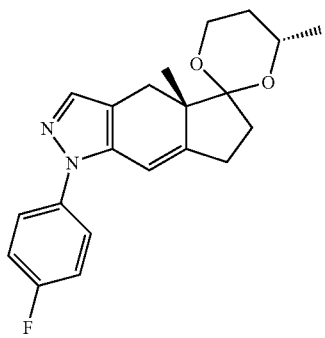
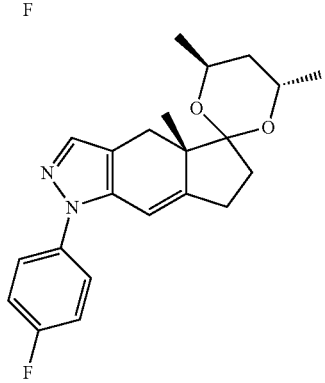
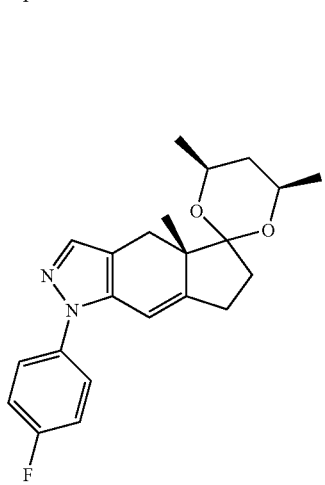
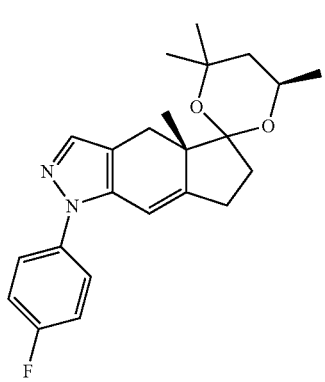

-continued
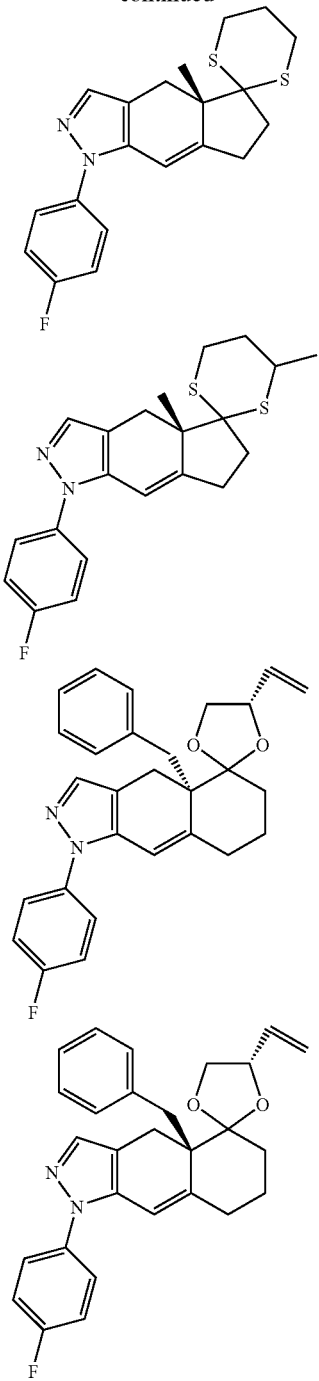
-continued
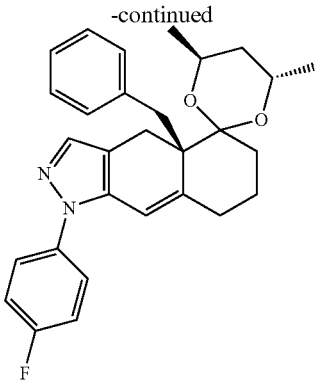
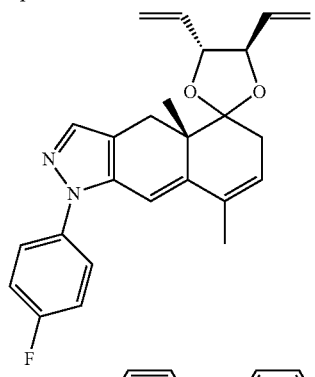
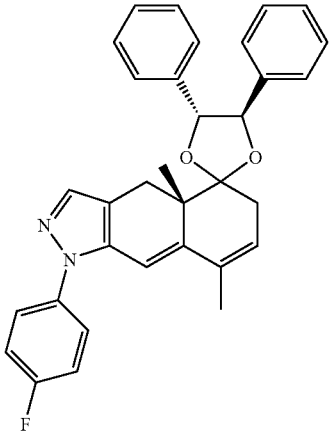
or a pharmaceutically acceptable salt of any of the foregoing compounds.
5. A pharmaceutical composition comprising acompound according to claim 1 in combination with a pharmaceutically acceptable carrier.
* * * * *